(12) United States Patent
Korman

(10) Patent No.: US 12,084,689 B2
(45) Date of Patent: *Sep. 10, 2024

(54) PRENYLTRANSFERASE VARIANTS WITH INCREASED THERMOSTABILITY

(71) Applicant: INVIZYNE TECHNOLOGIES, INC., Monrovia, CA (US)

(72) Inventor: Tyler P. Korman, Sierra Madre, CA (US)

(73) Assignee: INVIZYNE TECHNOLOGIES, INC., Monrovia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/934,560

(22) Filed: Sep. 22, 2022

(65) Prior Publication Data

US 2023/0098978 A1   Mar. 30, 2023

Related U.S. Application Data

(63) Continuation of application No. 17/824,118, filed on May 25, 2022, now Pat. No. 11,518,983.

(60) Provisional application No. 63/193,221, filed on May 26, 2021.

(51) Int. Cl.
| | | |
|---|---|---|
| *C12N 9/10* | (2006.01) | |
| *C12N 15/52* | (2006.01) | |
| *C12N 15/82* | (2006.01) | |
| *C12P 7/42* | (2006.01) | |

(52) U.S. Cl.
CPC ........... *C12N 9/1085* (2013.01); *C12N 15/52* (2013.01); *C12N 15/8243* (2013.01); *C12P 7/42* (2013.01); *C12Y 203/01206* (2015.07)

(58) Field of Classification Search
CPC .. C12N 9/1085; C12N 15/52; C12N 15/8243; C12P 7/42; C12Y 203/01206; C12Y 205/01102
See application file for complete search history.

(56) References Cited

U.S. PATENT DOCUMENTS

| | | | | |
|---|---|---|---|---|
| 11,518,983 | B1 * | 12/2022 | Korman | C12N 15/52 |
| 2022/0306999 | A1 * | 9/2022 | Anderson | C12Y 205/01 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

* cited by examiner

*Primary Examiner* — Ganapathirama Raghu
(74) *Attorney, Agent, or Firm* — FisherBroyles, LLP; Adam K. Whiting

(57) ABSTRACT

The present disclosure relates to recombinant prenyltransferase enzymes with increased thermostability and activity and the use of these enzymes in compositions and methods for biosynthesis involving prenylation reactions, including compositions and methods for the preparation of cannabinoids.

20 Claims, 8 Drawing Sheets

Specification includes a Sequence Listing.

PRENYLTRANSFERASE VARIANTS WITH INCREASED THERMOSTABILITY

CROSS-REFERENCE TO RELATED APPLICATIONS

The present application is a continuing application under 35 U.S.C. § 120 of U.S. patent application Ser. No. 17/824,118, filed May 25, 2022, and claims priority benefit under 35 U.S.C. § 119(e), of U.S. Provisional Patent Appl. No. 63/193,221, filed May 26, 2021, each of which is incorporated herein by reference in its entirety.

STATEMENT REGARDING FEDERALLY SPONSORED RESEARCH

The inventions disclosed herein were made with government support under SBIR Award Number R43GM137635 from the U.S. National Institutes of Health. The government has certain rights in the inventions.

FIELD

The present disclosure relates to recombinant prenyltransferase enzymes with increased thermostability and activity and the use of these enzymes in compositions and methods for biosynthesis involving prenylation reactions, including compositions and methods for the preparation of cannabinoids.

REFERENCE TO SEQUENCE LISTING

The official copy of the Sequence Listing is submitted concurrently with the specification via USPTO Patent Center as an WIPO Standard ST.26 formatted XML file with file name "15041002WO1.xml", a creation date of Sep. 22, 2022, and a size of 108,229 bytes. This Sequence Listing filed via USPTO Patent Center is part of the specification and is incorporated in its entirety by reference herein. The ST.26 formatted XML file "15041002WO1.xml" was created from, and adds no new matter to, the original ST.25 formatted text file "15041-002WO1_SeqList_ST25.txt" that was filed with U.S. patent application Ser. No. 17/824,118 on May 25, 2022.

BACKGROUND

Prenylation of natural compounds adds structural diversity, alters biological activity, and enhances therapeutic potential. Prenylated compounds often have low natural abundance or are difficult to isolate. Some prenylated natural products include a large class of bioactive molecules with demonstrated medicinal properties, including prenyl-flavonoids, prenyl-stilbenoids, and cannabinoids.

Cannabinoids are a large, well-known class of bioactive plant-derived compounds that regulate the cannabinoid receptors (CB1 and CB2) of the human endocannabinoid system. Cannabinoids are promising pharmacological agents with over 100 ongoing clinical trials investigating their therapeutic benefits as antiemetics, anticonvulsants, analgesics and antidepressants. Further, three cannabinoid therapies have been FDA approved to treat chemotherapy induced nausea, MS spasticity and seizures associated with severe epilepsy.

Although the plant, Cannabis sativa, is known to make over 100 different cannabinoid compounds, the best known and most studied cannabinoids include tetrahydrocannabidiolic acid (THCA), tetrahydrocannabidivarinic acid (THCVA), cannabidiolic acid (CBDA), cannabidivarinic acid (CBDVA), and their decarboxylated analogs (e.g., THC, THCV, CBD, CBDV). Of the cannabinoids made by the plant, nearly all are derived from the precursors cannabigerolic acid (CBGA) or cannabigerovarinic acid (CBGVA). In turn, CBGA and CBGVA are derived from the enzymatic prenylation of the polyketides, olivetolic acid (OA) or divarinic acid (DA), respectively, with geranyl pyrophosphate (GPP). The naturally occurring prenyltransferases found in C. sativa (e.g., PT4, UniProt: A0A455ZJC3) are membrane bound proteins.

A soluble prenyltransferase, NphB (UniProt: A0A2Z4JFA9), has been isolated from Streptomyces sp. CL190. See e.g., U.S. Pat. No. 7,361,483B2, which is hereby incorporated by reference herein in its entirety. NphB has been further engineered to provide soluble prenyltransferase variants capable of prenylating the aromatic polyketides, OA or DA with GPP to form the cannabinoid compounds, CBGA or CBGVA, respectively, under a range of biosynthetic conditions. See e.g., WO2019173770A1; WO2019183152A1; WO2020028722A1, WO2021134024A1, each of which is hereby incorporated by reference herein in its entirety. The engineered NphB variants can be used in cell-free biosynthesis systems and methods for the preparation of cannabinoid compounds. See e.g., WO2020028722A1 and WO2021134024A1.

There remains a need for prenyltransferases with improved properties, such as increased thermostability and activity, to provide for the efficient, large-scale biosynthetic production of prenylated compounds, such as cannabinoids.

SUMMARY

The present disclosure relates generally to recombinant prenyltransferase enzymes with increased thermostability and activity and the use of these enzymes in compositions and methods for biosynthesis involving prenylation reactions, including compositions and methods for the preparation of cannabinoids. This summary is intended to introduce the subject matter of the present disclosure, but does not cover each and every embodiment, combination, or variation that is contemplated and described within the present disclosure. Further embodiments are contemplated and described by the disclosure of the detailed description, drawings, and claims.

In at least one embodiment, the present disclosure provides a recombinant polypeptide having prenyltransferase activity and comprising an amino acid sequence of at least 80% identity to SEQ ID NO: 4, and amino acid residue differences as compared to SEQ ID NO: 4 at one or more positions selected from: 163, 91, 24, 48, 120, 144, 181, 200, 275, and 269; optionally, wherein the amino acid residue differences are: T163I, V91I, A24P, V48I, T120I, A144S, A181 P, V200E, T275V, and T269V. In at least one embodiment, the polypeptide comprises the amino acid residue differences: T163I, and V91I. In at least one embodiment, polypeptide comprises the amino acid residue differences: T163I, V91I, A24P, and T126P.

In at least one embodiment of the recombinant polypeptide having prenyltransferase activity, the polypeptide comprises:

(i) an S amino acid residue at position 232, and a V amino acid residue at position 288; and/or (ii) an amino acid residue difference as compared to SEQ ID NO: 4 at position 161; optionally, wherein the amino acid residue difference at position 161 is Q161H.

In at least one embodiment of the recombinant polypeptide having prenyltransferase activity, the polypeptide comprises additional amino acid residue differences as compared to SEQ ID NO: 4 at one or more positions selected from: 14, 31, 33, 69, 77, 78, 80, 93, 98, 112, 114, 126, 129, 131, 136, 222, 224, 225, 230, 236, 277, and 297; optionally, wherein the additional amino acid residue differences are selected from: M14I, Y31W, L33I, T69P, I77I, V78A, E80A, D93S, T98I, E112G, T114V, T126P, M129L, G131Q, S136A, E222D, G224S, K225Q, C230T, N236T, S277T, and G297K.

In at least one embodiment of the recombinant polypeptide having prenyltransferase activity, the polypeptide comprises a set of additional amino residue differences selected from:
(a) M14I, Y31W, T69P, I77I, T98I, S136A, E222D, G224S, N236T, and G297K;
(b) M14I, Y31W, T69P, T77I, E80A, D93S, T98I, T126P, M129L, G131Q, S136A, E222D, G224S, N236T, S277T, and G297K; or
(c) M14I, Y31W, L33I, T69P, T77I, V78A, E80A, D93S, I98I, E112G, T114V, T126P, M129L, G131Q, S136A, E222D, G224S, K225Q, N236T, S277T, and G297K.

In at least one embodiment of the recombinant polypeptide having prenyltransferase activity, the polypeptide comprises an amino acid sequence of at least 80%, at least 90%, at least 95%, at least 97%, at least 98%, or at least 99% identity to a sequence selected from the group consisting of SEQ ID NO: 6, 8, 10, 12, 14, 16, 18, 20, 22, 24, 28, 30, 32, 34, 36, 38, 40, 42, 44, 46, 48, 50, 52, 54, 56, and 58.

In at least one embodiment of the recombinant polypeptide having prenyltransferase activity, the thermostability of the polypeptide as compared to a polypeptide consisting of SEQ ID NO: 4 is increased at least 1.2-fold, at least 1.5-fold, at least 2-fold, at least 5-fold, or more; optionally, wherein the increased thermostability corresponds to the increased prenyltransferase activity measured after exposure of the polypeptides to a temperature of at least 55° C. in solution for at least 30 minutes.

In at least one embodiment of the recombinant polypeptide having prenyltransferase activity, the prenyltransferase activity of the polypeptide as compared to a polypeptide consisting of SEQ ID NO: 4 is increased at least 1.2-fold, at least 1.5-fold, at least 2-fold, at least 5-fold, or more; optionally, wherein the prenyltransferase activity is measured as the rate of conversion of the substrates olivetolic acid (OA) and geranyl pyrophosphate (GPP) to cannabigerolic acid (CBGA) under reaction conditions of 2.5 mM OA, 5 mM GPP, 5 mM MgCl$_2$, 50 mM Tris(hydroxymethyl)aminomethane (hereinafter "Tris") at pH 8.0 and 25° C.

In at least one embodiment, the present disclosure also provides a polynucleotide encoding recombinant polypeptide having prenyltransferase activity of the present disclosure. In at least one embodiment, the polynucleotide comprises a sequence having at least 80% identity to a sequence selected from the group consisting of the odd-numbered SEQ ID NO: 5-49.

In at least one embodiment, the present disclosure also provides an expression vector comprising a polynucleotide encoding recombinant polypeptide having prenyltransferase activity of the present disclosure; optionally, the expression vector comprises a control sequence.

In at least one embodiment, the present disclosure also provides a host cell comprising a polynucleotide or an expression vector comprising a polynucleotide, wherein the polynucleotide encodes recombinant polypeptide having prenyltransferase activity of the present disclosure.

In at least one embodiment, the present disclosure also provides a method for preparing a recombinant polypeptide having prenyltransferase activity of the present disclosure, wherein the method comprises culturing a host cell comprising a polynucleotide or an expression vector encoding the polypeptide, and isolating the polypeptide from the cultured host cell.

In at least one embodiment, the present disclosure provides a method for preparing a recombinant polypeptide having prenyltransferase activity of the present disclosure, the method comprising:
(a) transforming a host cell with an expression vector comprising a polynucleotide encoding the recombinant polypeptide; optionally, wherein said expression vector comprises a secretion signal;
(b) culturing said transformed host cell under conditions whereby said recombinant polypeptide is produced by said host cell; and
(c) recovering said recombinant polypeptide from said host cells, wherein recovering comprises heating a solution comprising the recombinant polypeptide to a temperature of at least about 55° C. for at least 30 minutes In at least one embodiment, the present disclosure also provides a method for preparing a compound of structural formula (I)

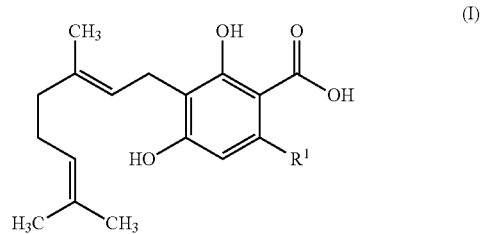

wherein, R$^1$ is C1-C7 alkyl,
the method comprising contacting under suitable reactions conditions a geranyl pyrophosphate (GPP) and a compound of structural formula (II)

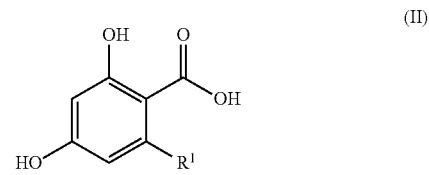

wherein, R$^1$ is C1-C7 alkyl,
and a recombinant polypeptide having prenyltransferase activity of the present disclosure.

In at least one embodiment of the method for preparing a compound of structural formula (I): (a) the compound of structure formula (I) is cannabigerolic acid (CBGA) and the compound of structural formula (II) is olivetolic acid (OA); (b) the compound of structure formula (I) is cannabigerovarinic acid (CBGVA) and the compound of structural formula (II) is divarinic acid (DA); or (c) the compound of structure formula (I) is cannabigerophorolic acid (CBGPA) and the compound of structural formula (II) is sphaerophorolic acid (PA).

In at least one embodiment of the method for preparing a compound of structural formula (I), the suitable reaction conditions comprise:

(a) a temperature of about 20° C. to about 45° C.; optionally, a temperature of about 37° C.;
(b) a substrate loading of at least about 0.6 g/L, at least about 1.2 g/L, at least about 2 g/L, at least about 6 g/L, at least about 12 g/L, at least about 18 g/L, at least about 24 g/L, at least about 30 g/L, or even greater; optionally, wherein the substrate is selected from olivetolic acid (OA), divarinic acid (DA), or sphaerophorolic acid (PA);
(c) a recombinant polypeptide concentration of about 0.1 g/L to about 5 g/L, or even lower concentration;
(d) a pH of about 4.0 to about 11.0, or about 5.0 to about 10.0; and/or
(e) a buffer solution of about 0.05 M Tris-Cl pH 8.0 to about 0.5 M Tris-Cl pH 8.0.

In at least one embodiment of the method for preparing a compound of structural formula (I), the suitable reaction conditions comprise olivetolic acid (OA), geranyl pyrophosphate (GPP), 0.1 M buffer pH 8.0, and the recombinant polypeptide at 37° C. for at least 1 hour.

In at least one embodiment of the method for preparing a compound of structural formula (I), the compound of structural formula (I) is prepared in purity of at least about 97%, at least about 98%, at least 99%, or at least about 99.5%.

In at least one embodiment, the present disclosure provides a composition comprising a recombinant polypeptide having prenyltransferase activity of the present disclosure and one or more enzymes that produce a substrate for the recombinant polypeptide. In at least one embodiment, the one or more enzymes produce a substrate selected from: geranyl pyrophosphate (GPP), olivetolic acid (OA), divarinic acid (DA), sphaerophorolic acid (PA), and a combination thereof. In at least one embodiment, the one or more enzymes comprises a plurality of enzymes that convert isoprenol or prenol to geranylpyrophosphate (GPP).

In at least one embodiment of the composition, the composition further comprises enzymes that convert malonate and acetyl-CoA to malonyl-CoA.

In at least one embodiment of the composition, the composition further comprises enzymes that convert ADP and/or AMP to ATP; optionally, wherein the enzymes that convert ADP and/or AMP to ATP also convert acetyl-phosphate to acetic acid.

In at least one embodiment of the composition, the one or more enzymes comprise at least the enzymes: (i) acyl activating enzyme 3 (AAE3); (ii) olivetol synthase (OLS); and/or (iii) olivetolic acid cyclase (OAC).

In at least one embodiment of the composition, the one or more enzymes comprise at least the enzymes: (i) Acetyl-phosphate transferase (PTA); (ii) Malonate decarboxylase alpha subunit (mdcA); (iii) Acyl activating enzyme 3 (AAE3); (iv) Olivetol synthase (OLS); (v) Olivetolic acid cyclase (OAC); (vi) Hydroxyethylthiazole kinase (ThiM); (vii) Isopentenyl kinase (IPK); (viii) Isopentyl diphosphate isomerase (IDI); (ix) Diphosphomevalonate decarboxylase alpha subunit (MDCa); and/or (x) Geranyl-PP synthase (GPPS) or Farnesyl-PP synthase mutant S82F (FPPS S82F).

BRIEF DESCRIPTION OF THE DRAWINGS

A better understanding of the novel features and advantages of the present disclosure will be obtained by reference to the following detailed description that sets forth illustrative embodiments, in which the principles of the disclosure are utilized, and the accompanying drawings (also "Figure" and "FIG." herein), of which.

DETAILED DESCRIPTION

Figure 1:
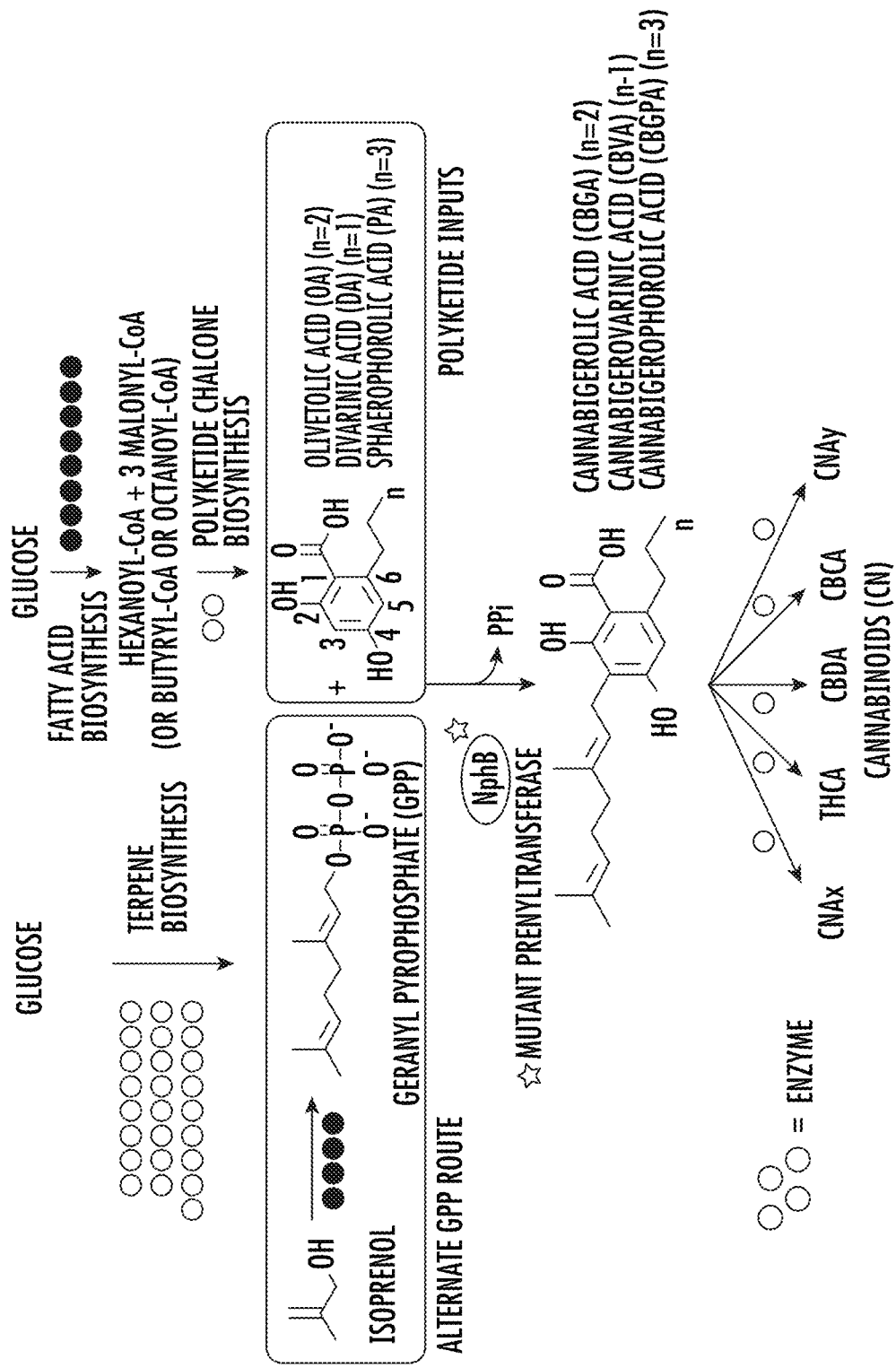
FIG. 1 depicts a schematic overview of steps, molecular inputs/outputs, and enzymes involved in the biosynthesis of various cannabinoid compounds relevant to the engineered NphB prenyltransferase polypeptide compositions and methods for their use in the biocatalytic preparation of cannabinoids of the present disclosure.

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of these limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in e.g., Green and Sambrook, *Molecular Cloning: A Laboratory Manual* (Fourth Edition), Vols. 1-3, Cold Spring Harbor Laboratory, Cold Spring Harbor, N.Y., 2012 (hereinafter "Sambrook"); and *Current Protocols in Molecular Biology*, F. M. Ausubel et al., eds., originally published in 1987 in book form by Greene Publishing Associates, Inc. and John Wiley & Sons, Inc., and regularly supplemented through 2011, and now available in journal format online as *Current Protocols in Molecular Biology*, Vols. 00-130, (1987-2020), published by Wiley & Sons, Inc. in the Wiley Online Library (hereinafter "Ausubel").

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

Definitions

"Cannabinoid" refers to a compound that acts on cannabinoid receptor, and is intended to include the endocannabinoid compounds that are produced naturally in animals, the phytocannabinoid compounds produced naturally in *cannabis* plants, and the synthetic cannabinoids compounds. Cannabinoids as referenced in the present disclosure include, but are not limited to, the exemplary naturally occurring and synthetic cannabinoid product compounds shown below in Table 1.

TABLE 1

Exemplary cannabinoid product compounds

| Compound Name | Abbrev. Name | Chemical Structure |
|---|---|---|
| cannabigerolic acid | CBGA | 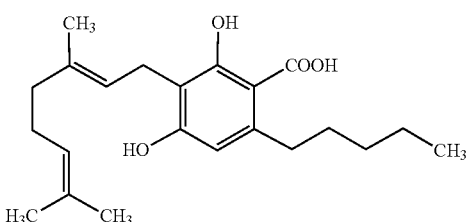 |
| cannabigerol | CBG | 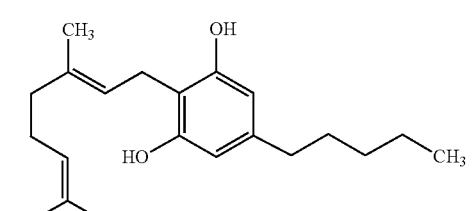 |
| $\Delta^9$-tetrahydrocannabinolic acid | $\Delta^9$-THCA | 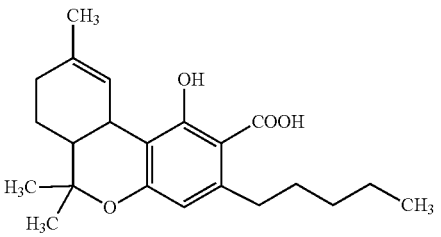 [SMILES: CCCCCc1cc2c(c(O)c1C(=O)O)C1C=C(C)CCC1C(C)(C)O2] |

TABLE 1-continued

Exemplary cannabinoid product compounds

| Compound Name | Abbrev. Name | Chemical Structure |
| --- | --- | --- |
| $\Delta^9$-tetrahydrocannabinol | $\Delta^9$-THC | 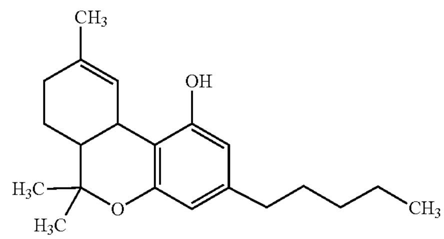 [SMILES: CCCCCc1cc(O)c2c(c1)OC(C)(C)C1CCC(C)=CC21] |
| $\Delta^8$-Metrahydrocannabinolic acid | $\Delta^8$-THCA | 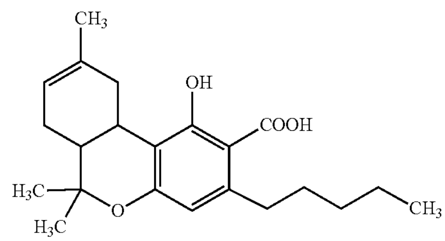 [SMILES: CCCCCc1cc2c(c(O)c1C(=O)O)C1CC(C)=CCC1C(C)(C)O2] |
| $\Delta^8$-tetrahydrocannabinol | $\Delta^8$-THC | 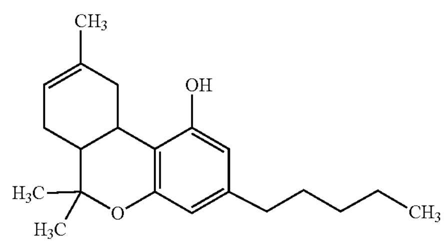 [SMILES: CCCCCc1cc(O)c2c(c1)OC(C)(C)C1CC=C(C)CC21] |
| cannabidiolic acid | CBDA | 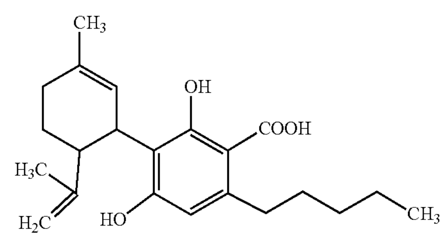 [SMILES: C=C(C)C1CCC(C)=CC1c1c(O)cc(CCCCC)c(C(=O)O)c1O] |
| cannabidiol | CBD | 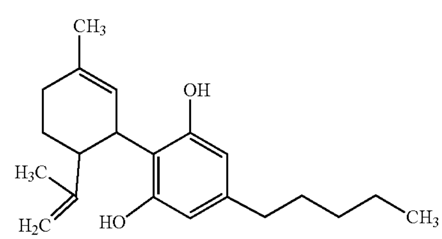 [SMILES: C=C(C)C1CCC(C)=CC1c1c(O)cc(CCCCC)cc1O] |
| cannabichromenic acid | CBCA | 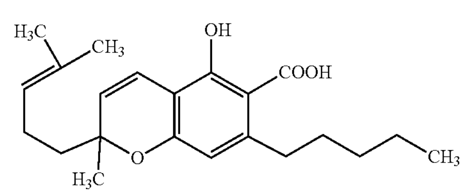 [SMILES: CCCCCc1cc2c(c(O)c1C(=O)O)C=CC(C)(CCC=C(C)C)O2] |

TABLE 1-continued

Exemplary cannabinoid product compounds

| Compound Name | Abbrev. Name | Chemical Structure |
| --- | --- | --- |
| cannabichromene | CBC | 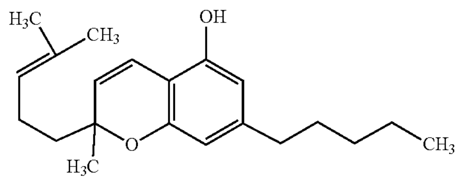 [SMILES: CCCCCc1cc(O)c2c(c1)OC(C)(CCC=C(C)C)C=C2] |
| cannabinolic acid | CBNA | 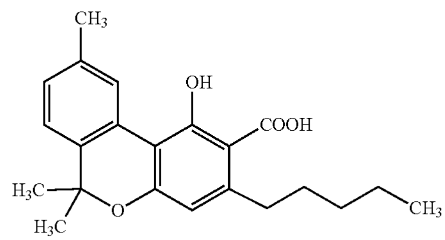 [SMILES: CCCCCc1cc2c(c(O)c1C(=O)O)-c1cc(C)ccc1C(C)(C)O2] |
| cannabinol | CBN | 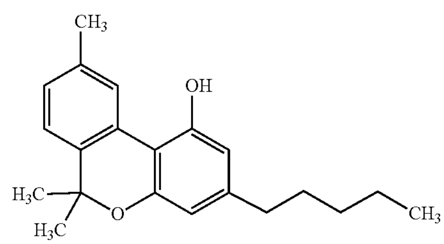 [SMILES: CCCCCc1cc(O)c2c(c1)OC(C)(C)c1ccc(C)cc1-2] |
| cannabidivarinic acid | CBDVA | 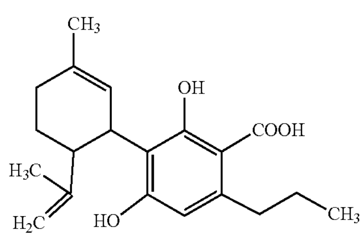 [SMILES: C=C(C)C1CCC(C)=CC1c1c(O)cc(CCC)c(C(=O)O)c1O] |
| cannabidivarin | CBDV | 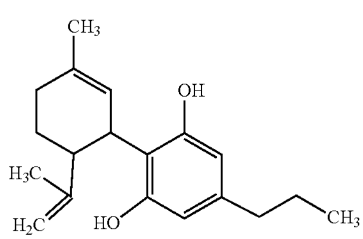 [SMILES: C=C(C)C1CCC(C)=CC1c1c(O)cc(CCC)cc1O] |
| Δ$^9$-tetrahydrocannabivarinic acid | Δ$^9$-THCVA | |

TABLE 1-continued

Exemplary cannabinoid product compounds

| Compound Name | Abbrev. Name | Chemical Structure |
|---|---|---|
| $\Delta^9$-tetrahydrocannabivarin | $\Delta^9$-THCV | 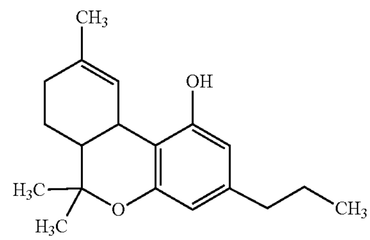 [SMILES: CCCc1cc(O)c2c(c1)OC(C)(C)C1CCC(C)=CC21] |
| cannabidibutolic acid | CBDBA | 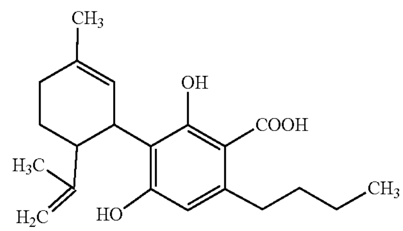 [SMILES: C=C(C)C1CCC(C)=CC1c1c(O)cc(CCCC)c(C(=O)O)c1O] |
| cannabidibutol | CBDB | 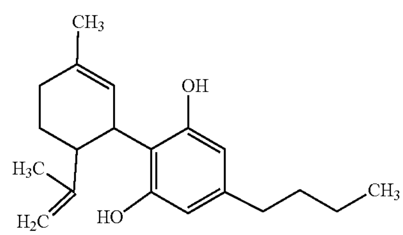 [SMILES: C=C(C)C1CCC(C)=CC1c1c(O)cc(CCCC)cc1O] |
| $\Delta^9$-tetrahydrocannabutolic acid | $\Delta^9$-THCBA | 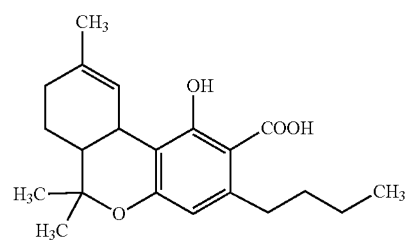 [SMILES: CCCCc1cc2c(c(O)c1C(=O)O)C1C=C(C)CCC1C(C)(C)O2] |
| $\Delta^9$-tetrahydrocannabutol | $\Delta^9$-THCB | 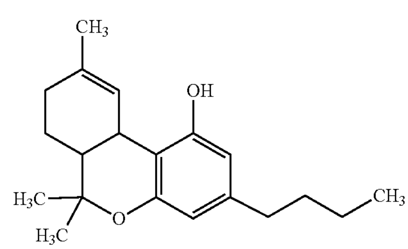 [SMILES: CCCCc1cc(O)c2c(c1)OC(C)(C)C1CCC(C)=CC21] |
| cannabigerosphaerophorolic acid | CBGPA | 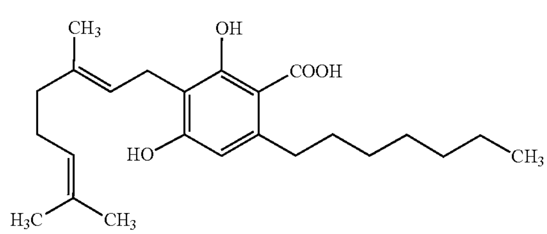 [SMILES: CCCCCCCc1cc(O)c(C/C=C(\C)CCC=C(C)C)c(O)c1C(=O)O] |

TABLE 1-continued

Exemplary cannabinoid product compounds

| Compound Name | Abbrev. Name | Chemical Structure |
|---|---|---|
| cannabigerosphaerophorol | CBGP | 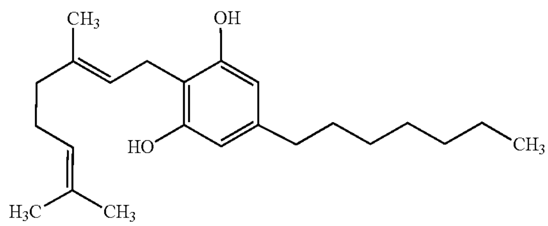 [SMILES: CCCCCCCc1cc(O)c(C/C=C(\C)CCC=C(C)C)c(O)c1] |
| cannabigerol-unsaturated-sphaerophorolic acid | CBGuPA | 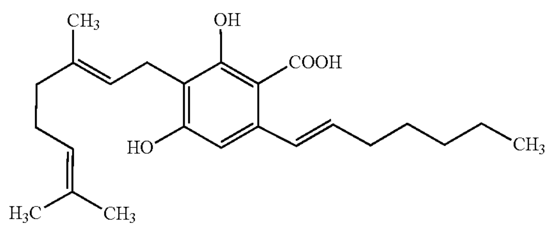 [SMILES: CCCCC/C=C/c1cc(O)c(C/C=C(\C)CCC=C(C)C)c(O)c1C(=O)O] |
| cannabigerol-unsaturated-sphaerophorol | CBGuP | 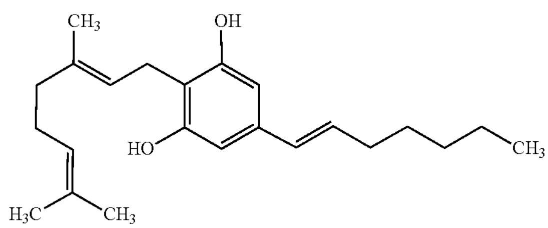 [SMILES: CCCCC/C=C/c1cc(O)c(C/C=C(\C)CCC=C(C)C)c(O)c1] |
| cannabidiphorolic acid | CBDPA | 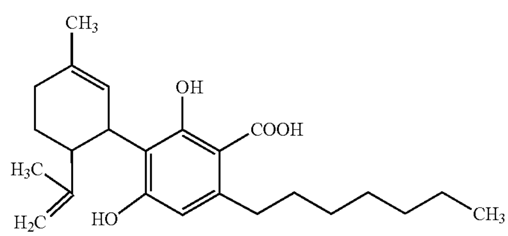 [SMILES: C=C(C)C1CCC(C)=CC1c1c(O)cc(CCCCCCC)c(C(=O)O)c1O] |
| cannabidiphorol | CBDP | 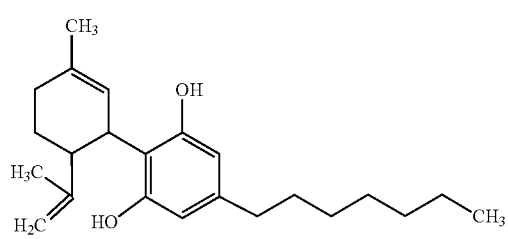 [SMILES: C=C(C)C1CCC(C)=CC1c1c(O)cc(CCCCCCC)cc1O] |
| tetrahydrocannabiphorolic acid | $\Delta^9$-THCPA | 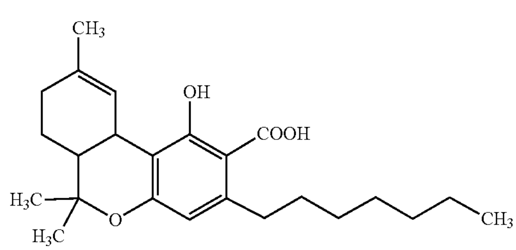 [SMILES: CCCCCCCc1cc2c(c(O)c1C(=O)O)C1C=C(C)CCC1C(C)(C)O2] |

TABLE 1-continued

Exemplary cannabinoid product compounds

| Compound Name | Abbrev. Name | Chemical Structure |
|---|---|---|
| Δ⁹-tetrahydrocannabiphorol | Δ⁹-THCP | |
| cannabichromevarinic acid | CBCVA | 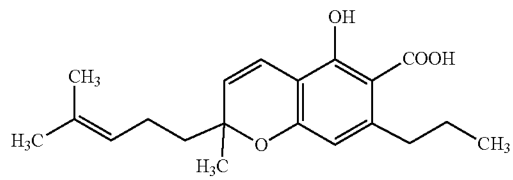 [SMILES: CCCc1cc2c(c(O)c1C(=O)O)C=CC(C)(CCC=C(C)C)O2] |
| cannabichromevarin | CBCV | 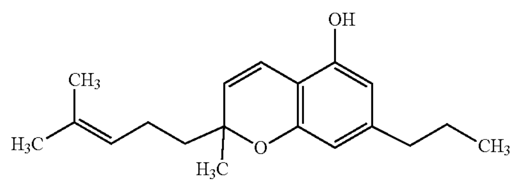 [SMILES: CCCc1cc(O)c2c(c1)OC(C)(CCC=C(C)C)C=C2] |
| cannabigerovarinic acid | CBGVA | 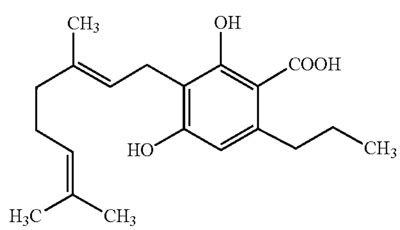 [SMILES: CCCc1cc(O)c(C/C=C(\C)CCC=C(C)C)c(O)c1C(=O)O] |
| cannabigerovarin | CBGV | 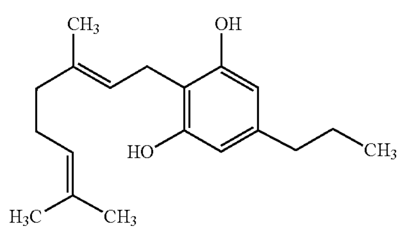 [SMILES: CCCc1cc(O)c(C/C=C(\C)CCC=C(C)C)c(O)c1] |
| cannabicyclolic acid | CBLA | 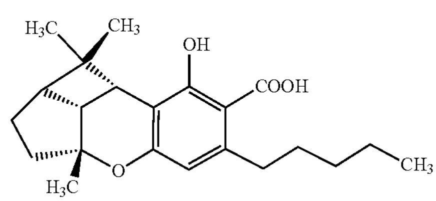 |
| cannabicyclol | CBL | 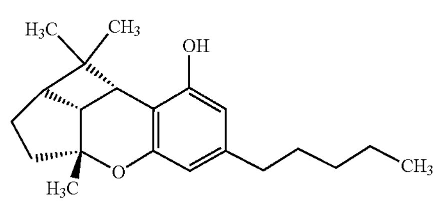 |

TABLE 1-continued

Exemplary cannabinoid product compounds

| Compound Name | Abbrev. Name | Chemical Structure |
|---|---|---|
| cannabielsoinic acid | CBEA | 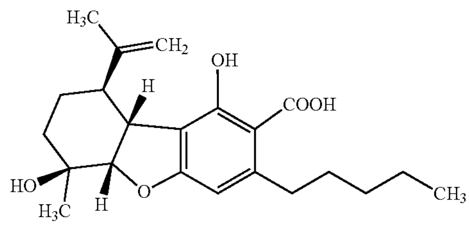 [SMILES: C=C(C)[C@@H]1CC[C@](C)(O)[C@H]2Oc3cc(CCCCC)c(C(=O)O)c(O)c3[C@@H]12] |
| cannabielsoin | CBE | 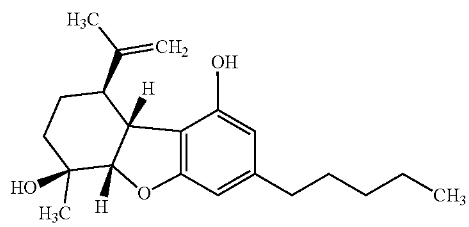 [SMILES: C=C(C)[C@@H]1CC[C@](C)(O)[C@H]2Oc3cc(CCCCC)cc(O)c3[C@@H]12] |
| cannabicitranic acid | CBTA | 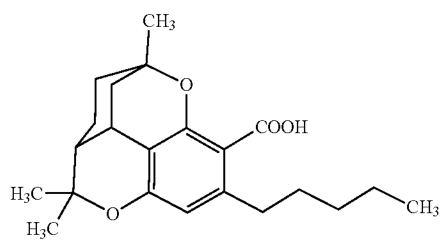 [SMILES: CCCCCc1cc2c3c(c1C(=O)O)OC1(C)CCC(C3C1)C(C)(C)O2] |
| cannabicitran | CBT | 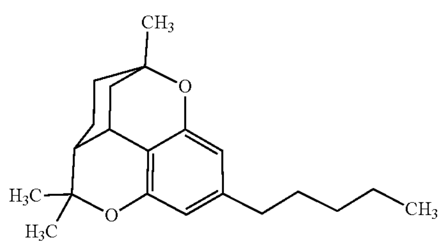 [SMILES: CCCCCc1cc2c3c(c1)OC(C)(C)C1CCC(C)(CC31)O2] |

"Conversion" as used herein refers to the enzymatic conversion of the substrate(s) to the corresponding product(s). "Percent conversion" refers to the percent of the substrate that is converted to the product within a period of time under specified conditions. Thus, the "enzymatic activity" or "activity" of an enzymatic conversion can be expressed as "percent conversion" of the substrate to the product.

"Product" as used herein in the context of an enzyme mediated process refers to the compound or molecule resulting from the activity of the enzyme. In the context of the engineered prenyltransferase polypeptides of the present disclosure, exemplary products include, but are not limited to, the cannabinoid compounds summarized in Table 1.

"Substrate" as used herein in the context of an enzyme mediated process refers to the compound or molecule acted on by the enzyme. In the context of the engineered prenyltransferase polypeptides of the present disclosure, substrates acted on by the polypeptides can include a range of "cannabinoid precursor" compound. "Cannabinoid precursor compound" or "cannabinoid precursor substrate" as used herein refers to a compound or molecule acted on by an enzyme in a biosynthetic step for producing a cannabinoid. Exemplary cannabinoid precursors are provided in Table 2, and include, but are not limited to, the aromatic polyketides, olivetolic acid (OA), or divarinic acid (DA), which are enzymatically prenylated with a geranyl group derived from geranyl pyrophosphate (GPP) to form the cannabinoids, CBGA, and CBGVA, respectively.

TABLE 2

Exemplary cannabinoid precursor substrate compounds

| Compound Name | Abbrev. Name | Chemical Structure |
|---|---|---|
| 2,4-dihydroxy-6-methylbenzoic acid | | 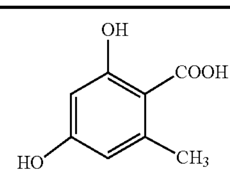 |

TABLE 2-continued

Exemplary cannabinoid precursor substrate compounds

| Compound Name | Abbrev. Name | Chemical Structure |
|---|---|---|
| 2-ethyl-4,6-dihydroxybenzoic acid | | (structure shown) |
| Divarinic acid (2,4-dihydroxy-6-propylbenzoic acid) | DA | (structure shown) |
| Butolic acid (2-butyl-4,6-dihydroxybenzoic acid) | BA | (structure shown) |
| Olivetolic acid (2,4-dihydroxy-6-pentylbenzoic acid) | OA | (structure shown) |
| 2-hexyl-4,6-dihydroxybenzoic acid | | (structure shown) |
| Sphaerophorolic acid (2-heptyl-4,6-dihydroxybenzoic acid) | PA | (structure shown) |
| Unsaturated sphaerophorolic acid | uPA | (structure shown) |

"Host cell" as used herein refers to a cell capable of being functionally modified with recombinant nucleic acids and functioning to express recombinant products, including polypeptides and compounds produced by activity of the polypeptides.

"Nucleic acid," or "polynucleotide" as used herein interchangeably to refer to two or more nucleosides that are covalently linked together. The nucleic acid may be wholly comprised ribonucleosides (e.g., RNA), wholly comprised of 2'-deoxyribonucleotides (e.g., DNA) or mixtures of ribo- and 2'-deoxyribonucleosides. The nucleoside units of the nucleic acid can be linked together via phosphodiester linkages (e.g., as in naturally occurring nucleic acids), or the nucleic acid can include one or more non-natural linkages (e.g., phosphorothioester linkage). Nucleic acid or polynucleotide is intended to include single-stranded or double-stranded molecules, or molecules having both single-stranded regions and double-stranded regions. Nucleic acid or polynucleotide is intended to include molecules composed of the naturally occurring nucleobases (i.e., adenine, guanine, uracil, thymine and cytosine), or molecules comprising that include one or more modified and/or synthetic nucleobases, such as, for example, inosine, xanthine, hypoxanthine, etc.

"Protein," "polypeptide," and "peptide" are used herein interchangeably to denote a polymer of at least two amino acids covalently linked by an amide bond, regardless of length or post-translational modification (e.g., glycosylation, phosphorylation, lipidation, myristilation, ubiquitination, etc.). As used herein "protein" or "polypeptide" or "peptide" polymer can include D- and L-amino acids, and mixtures of D- and L-amino acids.

"Naturally-occurring" or "wild-type" as used herein refers to the form as found in nature. For example, a naturally occurring nucleic acid sequence is the sequence present in an organism that can be isolated from a source in nature and which has not been intentionally modified by human manipulation.

"Recombinant," "engineered," or "non-naturally occurring" when used herein with reference to, e.g., a cell, nucleic acid, or polypeptide, refers to a material, or a material corresponding to the natural or native form of the material, that has been modified in a manner that would not otherwise exist in nature, or is identical thereto but is produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Nucleic acid derived from" as used herein refers to a nucleic acid having a sequence at least substantially identical to a sequence of found in naturally in an organism. For example, cDNA molecules prepared by reverse transcription of mRNA isolated from an organism, or nucleic acid molecules prepared synthetically to have a sequence at least substantially identical to, or which hybridizes to a sequence at least substantially identical to a nucleic sequence found in an organism.

"Coding sequence" refers to that portion of a nucleic acid (e.g., a gene) that encodes an amino acid sequence of a protein.

"Heterologous nucleic acid" as used herein refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the imine reductase enzymes may be codon optimized for optimal production from the host organism selected for expression.

"Preferred, optimal, high codon usage bias codons" refers to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella,*" 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

"Control sequence" as used herein refers to all sequences, which are necessary or advantageous for the expression of a polynucleotide and/or polypeptide as used in the present disclosure. Each control sequence may be native or foreign to the nucleic acid sequence encoding a polypeptide. Such control sequences include, but are not limited to, a leader, a promoter, a polyadenylation sequence, a pro-peptide sequence, a signal peptide sequence, and a transcription terminator. At a minimum, control sequences typically include a promoter, and transcriptional and translational stop signals. The control sequences may be provided with linkers for the purpose of introducing specific restriction sites facilitating ligation of the control sequences with the coding region of the nucleic acid sequence encoding a polypeptide.

"Operably linked" as used herein refers to a configuration in which a control sequence is appropriately placed (e.g., in a functional relationship) at a position relative to a polynucleotide sequence or polypeptide sequence of interest such that the control sequence directs or regulates the expression of the sequence of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Percentage of sequence identity," "percent sequence identity," "percentage homology," or "percent homology" are used interchangeably herein to refer to values quantifying comparisons of the sequences of polynucleotides or polypeptides, and are determined by comparing two optimally aligned sequences over a comparison window, wherein the portion of the polynucleotide or polypeptide sequence in the comparison window may comprise additions or deletions (or gaps) as compared to the reference sequence for optimal alignment of the two sequences. The percentage values may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length nucleic acid or polypeptide sequence. A reference sequence typically is at least 20 nucleotide or amino acid residue units in length, but can also be the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. "Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (or gaps) of 20 percent or less as compared to the reference sequence (which does not comprise additions or deletions) for optimal alignment of the two sequences.

"Substantial identity" or "substantially identical" refers to a polynucleotide or polypeptide sequence that has at least 70% sequence identity, at least 80% sequence identity, at least 85% sequence identity, at least 90% sequence identity, at least 95% sequence identity, or at least 99% sequence identity, as compared to a reference sequence over a comparison window of at least 20 nucleoside or amino acid residue positions, frequently over a window of at least 30-50 positions, wherein the percentage of sequence identity is calculated by comparing the reference sequence to a sequence that includes deletions or additions which total 20 percent or less of the reference sequence over the window of comparison.

"Corresponding to," "reference to," or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered imine reductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Isolated" as used herein in reference to a molecule means that the molecule (e.g., cannabinoid, polynucleotide, polypeptide) is substantially separated from other compounds that naturally accompany it, e.g., protein, lipids, and polynucleotides. The term embraces nucleic acids which have been removed or purified from their naturally-occurring environment or expression system (e.g., host cell or in vitro synthesis).

"Substantially pure" refers to a composition in which a desired molecule is the predominant species present (i.e., on a molar or weight basis it is more abundant than any other individual macromolecular species in the composition), and is generally a substantially purified composition when the object species comprises at least about 50 percent of the macromolecular species present by mole or % weight.

"Recovered" as used herein in relation to an enzyme, protein, or cannabinoid compound, refers to a more or less pure form of the enzyme, protein, or cannabinoid.

Engineered Prenyltransferase Polypeptides with Increased Thermostability

The present disclosure provides recombinant polypeptides having prenyltransferase activity and exhibiting increased thermostability and/or increased activity relative to the naturally occurring NphB enzyme of *Streptomyces* sp. (SEQ ID NO: 2). In particular, the recombinant polypeptides are capable of prenylating cannabinoid precursor substrate compounds, such as DA, OA, or PA, with a geranyl pyrophosphate (GPP) co-substrate compound to form the corresponding cannabinoid product compounds, CBGVA, CBGA, or CBGPA, respectively. In one exemplary embodiment, the recombinant polypeptides are capable of converting the cannabinoid precursor, olivetolic acid (OA) (compound (2)) and GPP to the cannabinoid, cannabigerolic acid (CBGA) (compound (1)), as shown in Scheme 1, and exhibit increased thermostability.

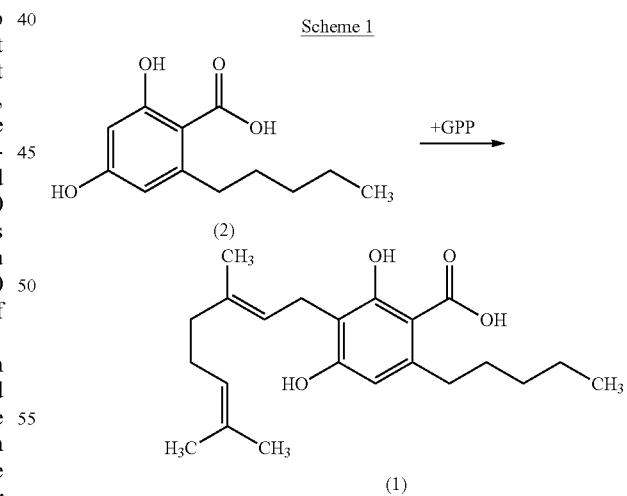

Scheme 1

The recombinant polypeptides of the present disclosure which exhibit increased thermostability and/or activity have one or more amino acid residue differences relative to a parent polypeptide "NphBM31" of SEQ ID NO: 4, which is an engineered variant of the naturally occurring NphB enzyme of *Streptomyces* sp. (SEQ ID NO: 2) with two added amino acid residue differences: A232S and Y288V. These two amino acid changes in NphBM31 result in a prenyltransferase that exhibits greater regiospecificity in the prenylation of OA with geranyl pyrophosphate (GPP) to form CBGA. The engineered NphBM31 parent polypeptide of SEQ ID NO: 4, however, loses activity slowly over time when stored at 4° C. and rapidly over minutes when incubated at elevated temperature (e.g., above 42° C.).

The recombinant polypeptides of the present disclosure are capable of converting the aromatic substrate OA (compound (2)) to the cannabinoid product CBGA (compound (1)) in the presence of the prenyl group donor substrate, GPP, at elevated temperature (e.g. above 42° C.) or for a longer period of time relative to the same conversion carried out by the wild-type polypeptide of SEQ ID NO: 2 or the engineered polypeptide of SEQ ID NO: 4. The recombinant polypeptides are non-naturally occurring prenyltransferases engineered to have one or more residue differences as compared to the wild-type NphB prenyltransferase amino acid sequence of SEQ ID NO:2 or the engineered polypeptide of SEQ ID NO:4. A range of exemplary recombinant engineered polypeptides that have amino acid residue differences relative to SEQ ID NO: 4 and exhibit prenyltransferase activity with the unexpected and surprising technical effect of increased thermostability and/or increased activity are summarized in Table 3 below.

TABLE 3

Recombinant engineered NphB polypeptides

| AA changes relative to NphBM31 (SEQ ID NO: 4) | AA Sequence | NT SEQ ID NO: | AA SEQ ID NO: |
|---|---|---|---|
| n/a (NphB wild-type) | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPT DNMPGVAELSAIPSMPPAVAENAELFARYGLDKVQMTSMDYK KRQVNLYFSELSAQTLEAESVLALVRELGLHVPNELGLKFCK RSFSVYPTLNWETGKIDRLCFAVISNDPTLVPSSDEGDIEKF HNYATKAPYAYVGEKRTLVYGLTLSPKEEYYKLGAYYHITDV QRGLLKAFDSLED | 1 | 2 |
| n/a (NphBM31 parent) | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPT DNMPGVAELSAIPSMPPAVAENAELFARYGLDKVQMTSMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 3 | 4 |
| A24P | MSEAADVERVYAAMEEAAGLLGVPCARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPT DNMPGVAELSAIPSMPPAVAENAELFARYGLDKVQMTSMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 5 | 6 |
| V48I | MSEAADVERVYAAMEEAAGLLGVACARDKIYPLLSTFQDTLV EGGSVIVFSMASGRHSTELDFSISVPTSHGDPYATVVEKGLF PATGHPVDDLLADTQKHLPVSMFAIDGEVTGGFKKTYAFFPT DNMPGVAELSAIPSMPPAVAENAELFARYGLDKVQMTSMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 51 | 52 |
| A86P | MSEAADVERVYAAMEEAAGLLGVACARDKIYPLLSTFQDTLV EGGSVVVFSMASGRHSTELDFSISVPTSHGDPYATVVEKGLF PPTGHPVDDLLADTQKHLPVSMFAIDGEVTGGFKKTYAFFPT DNMPGVAELSAIPSMPPAVAENAELFARYGLDKVQMTSMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 7 | 8 |
| V91I | MSEAADVERVYAAMEEAAGLLGVACARDKIYPLLSTFQDTLV EGGSVVVFSMASGRHSTELDFSISVPTSHGDPYATVVEKGLF PATGHPIDDLLADTQKHLPVSMFAIDGEVTGGFKKTYAFFPT DNMPGVAELSAIPSMPPAVAENAELFARYGLDKVQMTSMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 9 | 10 |
| T120I | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKIYAFFPT | 11 | 12 |

TABLE 3-continued

Recombinant engineered NphB polypeptides

| AA changes relative to NphBM31 (SEQ ID NO: 4) | AA Sequence | NT SEQ ID NO: | AA SEQ ID NO: |
|---|---|---|---|
| | DNMPGVAELSAIPSMPPAVAENAELFARYGLDKVQMTSMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | | |
| T126P | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPP DNMPGVAELSAIPSMPPAVAENAELFARYGLDKVQMTSMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 13 | 14 |
| A144S | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPT DNMPGVAELSATPSMPPSVAENAELFARYGLDKVQMTSMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 53 | 54 |
| T163I | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPT DNMPGVAELSAIPSMPPAVAENAELFARYGLDKVQMISMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 15 | 16 |
| Y167F | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPT DNMPGVAELSAIPSMPPAVAENAELFARYGLDKVQMTSMDFK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 17 | 18 |
| A181P | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPT DNMPGVAELSAIPSMPPAVAENAELFARYGLDKVQMTSMDYK KRQVNLYFSELSPQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 19 | 20 |
| V200E | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPT DNMPGVAELSAIPSMPPAVAENAELFARYGLDKVQMTSMDYK KRQVNLYFSELSAQTLEAESVLALVRELGLHEPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | 55 | 56 |
| T269V | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPT DNMPGVAELSAIPSMPPAVAENAELFARYGLDKVQMTSMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRVLVYGLTLSPKEEYYKLGAVYHITDV QRGLLKAFDSLED | 21 | 22 |
| V91I, T163I | MSEAADVERVYAAMEEAAGLLGVACARDKIYPLLSTFQDTLV EGGSVVVFSMASGRHSTELDFSISVPTSHGDPYATVVEKGLF PATGHPIDDLLADTQKHLPVSMFAIDGEVTGGFKKTYAFFPT DNMPGVAELSAIPSMPPAVAENAELFARYGLDKVQMISMDYK | 23 | 24 |

TABLE 3-continued

Recombinant engineered NphB polypeptides

| AA changes relative to NphBM31 (SEQ ID NO: 4) | AA Sequence | NT SEQ ID NO: | AA SEQ ID NO: |
|---|---|---|---|
| | KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLTLSPKEEYYKLGAVYHITDV QRGLLKAFDSLED | | |
| T275V | MSEAADVERVYAAMEEAAGLLGVACARDKIYPLLSTFQDTLV EGGSVVVFSMASGRHSTELDFSISVPTSHGDPYATVVEKGLF PATGHPVDDLLADTQKHLPVSMFAIDGEVTGGFKKTYAFFPT DNMPGVAELSAIPSMPPAVAENAELFARYGLDKVQMTSMDYK KRQVNLYFSELSAQTLEAESVLALVRELGLHVPNELGLKFCK RSFSVYPTLNWETGKIDRLCFSVISNDPTLVPSSDEGDIEKF HNYATKAPYAYVGEKRTLVYGLVLSPKEEYYKLGAVYHITDV QRGLLKAFDSLED | 57 | 58 |
| M14I, Y31W, T69P, T77I, T98I, S136A, E222D, G224S, N236T, G297K (NphBM31s) | MSEAADVERVYAAIEEAAGLLGVACARDKIWPLLSTFQDTLV EGGSVVVFSMASGRHSTELDFSISVPPSHGDPYAIVVEKGLF PATGHPVDDLLADIQKHLPVSMFAIDGEVTGGFKKTYAFFPT DNMPGVAELAAIPSMPPAVAENAELFARYGLDKVQMTSMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 25 | 26 |
| M14I, Y31W, T69P, T77I, T98I, S136A, E222D, G224S, N236T, G297K A24P | MSEAADVERVYAAIEEAAGLLGVPCARDKIWPLLSTFQDTLV EGGSVVVFSMASGRHSTELDFSISVPPSHGDPYAIVVEKGLF PATGHPVDDLLADIQKHLPVSMFAIDGEVTGGFKKTYAFFPT DNMPGVAELAAIPSMPPAVAENAELFARYGLDKVQMTSMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 27 | 28 |
| M14I, Y31W, T69P, T77I, T98I, S136A, E222D, G224S, N236T, G297K A24P, T126P | MSEAADVERVYAAIEEAAGLLGVPCARDKIWPLLSTFQDTLV EGGSVVVFSMASGRHSTELDFSISVPPSHGDPYAIVVEKGLF PATGHPVDDLLADIQKHLPVSMFAIDGEVTGGFKKTYAFFPP DNMPGVAELAAIPSMPPAVAENAELFARYGLDKVQMTSMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 29 | 30 |
| M14I, Y31W, T69P, T77I, T98I, S136A, E222D, G224S, N236T, G297K A86P | MSEAADVERVYAAIEEAAGLLGVACARDKIWPLLSTFQDTLV EGGSVVVFSMASGRHSTELDFSISVPPSHGDPYAIVVEKGLF PPTGHPVDDLLADIQKHLPVSMFAIDGEVTGGFKKTYAFFPT DNMPGVAELAAIPSMPPAVAENAELFARYGLDKVQMTSMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 31 | 32 |
| M14I, Y31W, T69P, T77I, T98I, S136A, E222D, G224S, N236T, G297K V91I | MSEAADVERVYAAIEEAAGLLGVACARDKIWPLLSTFQDTLV EGGSVVVFSMASGRHSTELDFSISVPPSHGDPYAIVVEKGLF PATGHPIDDLLADIQKHLPVSMFAIDGEVTGGFKKTYAFFPT DNMPGVAELAAIPSMPPAVAENAELFARYGLDKVQMTSMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 33 | 34 |
| M14I, Y31W, T69P, T77I, T98I, S136A, E222D, G224S, N236T, G297K T120I | MSEAADVERVYAAIEEAAGLLGVACARDKIWPLLSTFQDTLV EGGSVVVFSMASGRHSTELDFSISVPPSHGDPYAIVVEKGLF PATGHPVDDLLADIQKHLPVSMFAIDGEVTGGFKKIYAFFPT DNMPGVAELAAIPSMPPAVAENAELFARYGLDKVQMTSMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 35 | 36 |

TABLE 3-continued

Recombinant engineered NphB polypeptides

| AA changes relative to NphBM31 (SEQ ID NO: 4) | AA Sequence | NT SEQ ID NO: | AA SEQ ID NO: |
|---|---|---|---|
| M14I, Y31W, T69P, T77I, T98I, S136A, E222D, G224S, N236T, G297K T126P | MSEAADVERVYAAIEEAAGLLGVACARDKIWPLLSTFQDTLV EGGSVVVFSMASGRHSTELDFSISVPPSHGDPYAIVVEKGLF PATGHPVDDLLADIQKHLPVSMFAIDGEVTGGFKKTYAFFPP DNMPGVAELAAIPSMPPAVAENAELFARYGLDKVQMTSMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 37 | 38 |
| M14I, Y31W, T69P, T77I, T98I, S136A, E222D, G224S, N236T, G297K T163I | MSEAADVERVYAAIEEAAGLLGVACARDKIWPLLSTFQDTLV EGGSVVVFSMASGRHSTELDFSISVPPSHGDPYAIVVEKGLF PATGHPVDDLLADIQKHLPVSMFAIDGEVTGGFKKTYAFFPT DNMPGVAELAAIPSMPPAVAENAELFARYGLDKVQMISMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 39 | 40 |
| M14I, Y31W, T69P, T77I, T98I, S136A, E222D, G224S, N236T, G297K A181P | MSEAADVERVYAAIEEAAGLLGVACARDKIWPLLSTFQDTLV EGGSVVVFSMASGRHSTELDFSISVPPSHGDPYAIVVEKGLF PATGHPVDDLLADIQKHLPVSMFAIDGEVTGGFKKTYAFFPT DNMPGVAELAAIPSMPPAVAENAELFARYGLDKVQMTSMDYK KRQVNLYFSELSPQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 41 | 42 |
| M14I, Y31W, T69P, T77I, T98I, S136A, E222D, G224S, N236T, G297K T269V | MSEAADVERVYAAIEEAAGLLGVACARDKIWPLLSTFQDTLV EGGSVVVFSMASGRHSTELDFSISVPPSHGDPYAIVVEKGLF PATGHPVDDLLADIQKHLPVSMFAIDGEVTGGFKKTYAFFPT DNMPGVAELAAIPSMPPAVAENAELFARYGLDKVQMTSMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRVLVYGLTLSPKEEYYKLGAVYHITDV QRKLLKAFDSLED | 43 | 44 |
| M14I, Y31W, T69P, T77I, T98I, S136A, E222D, G224S, N236T, G297K V91I, T163I | MSEAADVERVYAAIEEAAGLLGVACARDKIWPLLSTFQDTLV EGGSVVVFSMASGRHSTELDFSISVPPSHGDPYAIVVEKGLF PATGHPIDDLLADIQKHLPVSMFAIDGEVTGGFKKTYAFFPT DNMPGVAELAAIPSMPPAVAENAELFARYGLDKVQMISMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 45 | 46 |
| M14I, Y31W, T69P, T77I, T98I, S136A, E222D, G224S, N236T, G297K A24P, V91I, T126P, T163I (NphBM33s) | MSEAADVERVYAAIEEAAGLLGVPCARDKIWPLLSTFQDTLV EGGSVVVFSMASGRHSTELDFSISVPPSHGDPYAIVVEKGLF PATGHPIDDLLADIQKHLPVSMFAIDGEVTGGFKKTYAFFPP DNMPGVAELAAIPSMPPAVAENAELFARYGLDKVQMISMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRTLVYGLTLSPKEEYYKLGAVYHITDV QRKLLKAFDSLED | 47 | 48 |
| M14I, Y31W, T69P, T77I, T98I, S136A, E222D, G224S, N236T, G297K A24P, V91I, T126P, T163I, T269V (NphBM34s) | MSEAADVERVYAAIEEAAGLLGVPCARDKIWPLLSTFQDTLV EGGSVVVFSMASGRHSTELDFSISVPPSHGDPYAIVVEKGLF PATGHPIDDLLADIQKHLPVSMFAIDGEVTGGFKKTYAFFPP DNMPGVAELAAIPSMPPAVAENAELFARYGLDKVQMISMDYK KRQVNLYFSELSAQTLEAESVLALVRELGLHVPNELGLKFCK RSFSVYPTLNWDTSKIDRLCFSVISTDPTLVPSSDEGDIEKF HNYATKAPYAYVGEKRVLVYGLTLSPKEEYYKLGAVYHITDV QRKLLKAFDSLED | 49 | 50 |

In at least one embodiment, the recombinant polypeptides having prenyltransferase activity and increased thermostability have one or more residue differences as compared to the engineered reference polypeptide "NphBM31" of SEQ ID NO:4. In some embodiments, the recombinant polypeptides have one or more residue differences at residue positions selected from 24, 91, 120, 181, 163, and 269. As further described below, the recombinant polypeptides can have in combination with the residue differences at the foregoing residue positions, one or more residue differences at residue positions selected from 14, 31, 33, 69, 77, 78, 80, 93, 98, 112, 114, 126, 129, 131, 136, 222, 224, 225, 230, 236, 277, and 297.

It is to be understood that the residue differences from SEQ ID NO:4 at residue positions associated with increased thermostability enzymes can be used in various combinations to form recombinant prenyltransferase polypeptides having desirable enzymatic characteristics, for example combination of increased thermostability, and increased conversion rate, product yield, and/or utilization of prenyl group donor substrate. Exemplary combinations are described herein. For example, the present disclosure provides a recombinant polypeptide having prenyltransferase activity and increased thermostability, wherein the polypeptide comprises an amino acid sequence of at least 80% identity to SEQ ID NO: 4, and amino acid residue differences as compared to SEQ ID NO: 4 at one or more positions selected from: 24, 48, 91, 120, 144, 163, 181, 200, 275, and 269. In at least one embodiment, the amino acid residue differences are: A24P, V48I, V91I, T120I, A144S, T163I, A181P, V200E, T275V, and T269V.

In at least one embodiment, the present disclosure provides a recombinant polypeptide having prenyltransferase activity and increased thermostability, wherein the polypeptide comprises an amino acid sequence of at least 80%, at least 85%, at least 90%, at least 95%, or greater, sequence identity to SEQ ID NO: 4, and amino acid residue differences as compared to SEQ ID NO: 4 selected from the list consisting of: V91I, and T163I. In at least one embodiment, the recombinant polypeptide comprises both of the amino acid residue differences V91I and T163I. In at least one embodiment, the recombinant polypeptide comprising the amino acid residue differences as compared to SEQ ID NO: 4 selected from the list consisting of V91I, and T163I, comprises an amino acid sequence of at least 80%, at least 85%, at least 90%, at least 95%, or greater, sequence identity an amino acid sequence selected from SEQ ID NO: 10, 16, 24, 34, 40, 46, 48, and 50.

In at least one embodiment, the present disclosure provides a recombinant polypeptide having prenyltransferase activity and increased thermostability, wherein the polypeptide comprises an amino acid sequence of at least 80%, at least 85%, at least 90%, at least 95%, or greater, sequence identity to SEQ ID NO: 4, and amino acid residue differences as compared to SEQ ID NO: 4 selected from the list consisting of: A24P, V91I, T126P, and T163I. In at least one embodiment, the recombinant polypeptide comprising the amino acid residue differences as compared to SEQ ID NO: 4 selected from the list consisting of A24P, V91I, T126P, and T163I, comprises an amino acid sequence of at least 80%, at least 85%, at least 90%, at least 95%, or greater, sequence identity an amino acid sequence selected from SEQ ID NO: 6, 10, 14, 16, 24, 26, 28, 30, 34, 38, 40, 46, 48, and 50.

In at least one embodiment, the present disclosure provides a recombinant polypeptide having prenyltransferase activity and increased thermostability, wherein the polypeptide comprises an amino acid sequence of at least 80%, at least 85%, at least 90%, at least 95%, or greater, sequence identity to SEQ ID NO: 4, and amino acid residue differences as compared to SEQ ID NO: 4 selected from the list consisting of: A24P, V91I, T126P, and T163I, and further comprises the amino acid differences: M14I, Y31W, T69P, I77I, T98I, S136A, E222D, G224S, N236T, and G297K. In at least one embodiment, the recombinant polypeptide comprises an amino acid sequence of at least 80%, at least 85%, at least 90%, at least 95%, or greater, identity to SEQ ID NO: 26, 28, 30, 34, 38, 40, 46, 48, and 50.

In at least one embodiment, the present disclosure provides a recombinant polypeptide having prenyltransferase activity and increased thermostability, wherein the polypeptide comprises an amino acid sequence of at least 80%, at least 85%, at least 90%, at least 95%, or greater, sequence identity to SEQ ID NO: 4, and the following four "PPII" amino acid residue differences as compared to SEQ ID NO: 4: A24P, V91I, T126P, and T163I. In at least one embodiment, the recombinant polypeptide comprising the four "PPII" amino acid residue differences as compared to SEQ ID NO: 4 comprises an amino acid sequence of at least 80%, at least 85%, at least 90%, at least 95%, or greater, sequence identity an amino acid sequence selected from SEQ ID NO: 26, 48, and 50.

In at least one embodiment, the amino acid sequence of a recombinant polypeptide of the present disclosure can also comprise the amino acid differences: (i) an S amino acid residue at position 232, and a V amino acid residue at position 288; and/or (ii) an amino acid residue difference as compared to SEQ ID NO: 4 at position 161; optionally, wherein the amino acid residue difference at position 161 is Q161H.

It is further contemplated, that the recombinant polypeptide having prenyltransferase activity can further comprise further amino acid residue differences as compared to SEQ ID NO: 4 at one or more positions selected from: 14, 31, 33, 69, 77, 78, 80, 93, 98, 112, 114, 126, 129, 131, 136, 222, 224, 225, 230, 236, 277, and 297. In at least one embodiment, the additional amino acid residue differences are selected from: M14I, Y31W, L33I, T69P, T77I, V78A, E80A, D93S, T98I, E112G, T114V, T126P, M129L, G131Q, S136A, E222D, G224S, K225Q, C230T, N236T, S277T, and G297K.

In at least one embodiment of the recombinant polypeptide having prenyltransferase activity and increased thermostability, it is contemplated that the polypeptide comprises an amino acid sequence with a specific set of additional amino residue differences relative to SEQ ID NO: 4. In at least one embodiment the specific set of amino acid residue differences is selected from:

(a) M14I, Y31W, T69P, I77I, T98I, S136A, E222D, G224S, N236T, and G297K;

(b) M14I, Y31W, T69P, T77I, E80A, D93S, T98I, T126P, M129L, G131Q, S136A, E222D, G224S, N236T, S277T, and G297K; or (c) M14I, Y31W, L33I, T69P, T77I, V78A, E80A, D93S, T98I, E112G, T114V, T126P, M129L, G131Q, S136A, E222D, G224S, K225Q, N236T, S277T, and G297K.

Based on the correlation of recombinant polypeptide functional information provided herein with the sequence information provided in Table 3 and the accompanying Sequence Listing, one of ordinary skill can recognize that the present disclosure provides a range of recombinant polypeptides having prenyltransferase activity and increased thermostability, wherein the polypeptide comprises an amino acid sequence comprising one or more of the amino acid differences or sets of amino acid differences (relative to SEQ ID NO: 4) disclosed in any one of SEQ ID NO: 6, 8, 10, 12, 14, 16, 18, 20, 22, 24, 28, 30, 32, 34, 36, 38, 40, 42, 44, 46, 48, 50, 52, 54, 56, and 58, and otherwise have at least 80%, at least 90%, at least 95%, at least 97%, at least 98%, or at least 99% identity to a sequence selected from the group consisting of SEQ ID NO: 2, 4, 6, 8, 10, 12, 14, 16, 18, 20, 22, 24, 28, 30, 32, 34, 36, 38, 40, 42, 44, 46, 48, 50, 52, 54, 56, and 58.

Thus, in at least one embodiment, a recombinant polypeptide of the present disclosure having prenyltransferase activity and increased thermostability can have an amino acid sequence comprising one or more of the amino acid differences or sets of amino acid differences (relative to SEQ ID NO: 4) disclosed in any one of SEQ ID NO: 6, 8, 10, 12, 14, 16, 18, 20, 22, 24, 28, 30, 32, 34, 36, 38, 40, 42, 44, 46, 48, 50, 52, 54, 56, and 58, and additionally have 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, or 1-60 residue differences at other residue positions. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 60 residue differences at the other residue positions.

In addition to the residue positions specified above, any of the engineered prenyltransferase polypeptides disclosed herein can further comprise other residue differences relative to wild-type NphB polypeptide of SEQ ID NO:2 at other residue positions. Residue differences at these other residue positions can provide for additional variations in the amino acid sequence without adversely affecting the ability of the recombinant polypeptide to carry out the desired biocatalytic conversion (e.g., conversion of compound (2) to compound (1)). In some embodiments, the recombinant polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40 residue differences at other amino acid residue positions as compared to SEQ ID NO: 2. In some embodiments, the number of differences can be 1, 2, 3, 4, 5, 6, 7, 8, 9, 10, 11, 12, 14, 15, 16, 18, 20, 22, 24, 26, 30, 35, and 40 residue differences at other residue positions. The residue difference at these other positions can include conservative changes or non-conservative changes. In some embodiments, the residue differences can comprise conservative substitutions and non-conservative substitutions as compared to the wild-type NphB polypeptide of SEQ ID NO: 2.

Amino acid residue differences at other positions relative to the wild-type sequence of SEQ ID NO: 2 and the effect of these differences on enzyme function are provide by other recombinant prenyltransferase polypeptides disclosed in international patent applications with publication nos. WO2019173770A1, WO2019183152A1, WO2020028722A1, and WO2021134024A1, each of which is hereby incorporated by reference herein in its entirety. Accordingly, in some embodiments, one or more of the amino acid differences provided in the recombinant polypeptides of WO2019173770A1, WO2019183152A1, WO2020028722A1, and WO2021134024A1 could also be introduced into a recombinant prenyltransferase polypeptide of the present disclosure.

In some embodiments, the present disclosure provides a recombinant polypeptide capable of converting compound (2) to compound (1) with increased thermostability relative to the activity of the polypeptide of SEQ ID NO: 2, which comprises an amino acid sequence having at least 80%, 85%, 86%, 87%, 88%, 89%, 90%, 91%, 92%, 93%, 94%, 95%, 96%, 97%, 98%, or 99% identity to SEQ ID NO: 2, with the proviso that the amino acid sequence of any one or more of the engineered prenyltransferase polypeptides disclosed in any one or more of international patent applications, WO2019173770A1, WO2019183152A1, WO2020028722A1, or WO2021134024A1.

In some embodiments, the recombinant polypeptides of the disclosure can be in the form of fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the recombinant polypeptides described herein can be used with or without fusions to other polypeptides. It is also contemplated that the recombinant polypeptides described herein are not restricted to the genetically encoded amino acids. In addition to the genetically encoded amino acids, the polypeptides described herein may be comprised, either in whole or in part, of naturally-occurring and/or synthetic non-encoded amino acids.

In another aspect, the present disclosure provides polynucleotides encoding the recombinant polypeptides having prenyltransferase activity and increased thermostability as described herein. In at least one embodiment, the polynucleotide comprises a sequence encoding an exemplary recombinant polypeptide having prenyltransferase activity as disclosed in Table 3 and accompanying Sequence Listing.

In at least one embodiment, the polynucleotide encoding a recombinant polypeptide having prenyltransferase activity and increased thermostability comprises an amino acid sequence that is at least about 80%, 85%, 90%, 91%, 92%, 93%, 94%, 95%, 96%, 97%, 98%, 99%, or more identical to the wild-type sequence of SEQ ID NO:2 or the engineered parent polypeptide of SEQ ID NO: 4. In some embodiments, the polynucleotide encodes a recombinant polypeptide comprising an amino acid sequence that has the percent identity described above and has one or more amino acid residue differences as compared to SEQ ID NO:4 described elsewhere herein, for example at residue positions selected from: 24, 48, 91, 120, 144, 163, 181, 200, 275, and 269.

In at least one embodiment, the polynucleotide comprises a sequence of at least 80%, at least 85%, at least 90%, at least 95%, at least 97%, at least 98%, or at least 99% identity to a sequence selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, and 57. In at least one embodiment, the polynucleotide comprises a codon degenerate sequence of a sequence selected from the group consisting of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, and 57.

The polynucleotides encoding the recombinant polypeptides of the present disclosure may be operatively linked to one or more heterologous regulatory sequences that control gene expression to create a recombinant polynucleotide capable of expressing the polypeptide. Expression constructs containing a heterologous polynucleotide encoding the recombinant polypeptide can be introduced into appropriate host cells to express the corresponding polypeptide. Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved prenyltransferase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 3.

The codons can be selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. It is contemplated that all codons need not be replaced to optimize the codon usage of the recombinant polypeptide since the natural sequence will comprise preferred codons and because use of preferred codons may not be required for all amino acid residues. Consequently, codon optimized polynucleotides encoding the recombinant polypeptide may contain preferred codons at about 40%, 50%, 60%, 70%, 80%, or greater than 90% of codon positions of the full length coding region.

The present disclosure provides an expression vector comprising a polynucleotide encoding a recombinant polypeptide having prenyltransferase activity and increased thermostability, and one or more expression regulating regions such as a promoter, a terminator, a replication origin, or the like, depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the recombinant polypeptide at such sites. Alternatively, a polynucleotide sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression. The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. In at least one embodiment, the expression vector further comprises one or more selectable markers, which permit easy selection of transformed cells.

The present disclosure also provides host cell comprising a polynucleotide or expression vector encoding a recombinant engineered prenyltransferase polypeptide of the present disclosure, wherein the polynucleotide is operatively linked to one or more control sequences for expression of the polypeptide having prenyltransferase activity in the host cell. Host cells for use in expressing the polypeptides encoded by the expression vectors of the present invention are well known in the art and include but are not limited to, bacterial cells, such as *E. coli, Bacillus subtilis*, or fungal cells, such as *Saccharomyces cerevisiae* or *Pichia pastoris*, insect cells, such as *Drosophila* S2 and *Spodoptera* Sf9, animal cells, such as CHO, COS, BHK, 293, and plant cells. Appropriate culture mediums and growth conditions for the above-described host cells are well known in the art.

In at least one embodiment, the present disclosure provides a method for producing a cannabinoid comprising: (a) culturing in a suitable medium a recombinant host cell of the present disclosure; and (b) recovering the produced cannabinoid. As disclosed elsewhere herein, the increased thermostability of the engineered prenyltransferase (PT) polypeptides of the present disclosure provides at least the following benefits for the use of these enzymes: simplified heat purification (allowing more efficient enzyme preparation), increased biosynthetic reaction lifetime (allowing less enzyme to be used in biosynthesis and more complete reactions), higher temperature biosynthetic reaction (allowing increased reaction rate to completion).

The prenyltransferase catalyzed transfer of a prenyl group from a donor substrate, such as geranyl pyrophosphate (GPP) to a polyketide compound is a critical enzymatic step in the biosynthesis of many compounds of interest, including cannabinoids. Accordingly, it is contemplated that the engineered polypeptides and increased thermostability of the present disclosure can be used in a range of in vitro, cell-free systems, or in vivo, recombinant host cell systems for the biosynthesis of compounds requiring a prenyltransferase step. FIG. 1 depicts a schematic overview of the molecular inputs/outputs and enzymes involved in such an exemplary system for the biosynthesis of cannabinoid compounds. In the right side of the scheme of FIG. 1, the input molecule glucose is converted via fatty acid biosynthesis enzymes to the precursor compounds, hexanoyl-CoA and malonyl-CoA. Or alternatively to hexanoyl-CoA, butyryl-CoA or octanoyl-CoA. The precursors, hexanoyl-CoA and malonyl-CoA are converted via polyketide chalcone biosynthesis enzymes to the cannabinoid precursor compounds, olivetolic acid (OA). Or alternatively, butyryl-CoA is converted to divarinic acid (DA), or the precursor octanoyl-CoA is converted to sphaerophorolic acid (PA). Each of the cannabinoid precursors in this scheme, OA, DA, or PA, is capable as acting as a cannabinoid precursor substrate compound, or as the "polyketide input," with the engineered NphB prenyltransferases of the present disclosure. The left side of this scheme of FIG. 1, depicts a terpene biosynthesis route that converts glucose input molecules to geranyl pyrophosphate (GPP), which is the co-substrate used by the engineered NphB to convert the cannabinoid precursor, OA, DA, or PA, to the corresponding cannabinoid product compounds, CBGA, CBGVA, or C2471 BGPA. These exemplary cannabinoid product compounds differ only in the length alkyl carbon chain as shown by the generic structure depicted in FIG. 1. As shown in the scheme, these cannabinoid products are themselves precursor substrate compounds that can be converted by cannabinoid synthase enzyme to the cannabinoids, THCA, CBDA, CBCA, and other structural analogs.

In at least one embodiment, the engineered polypeptides with prenyltransferase activity and increased thermostability and/or activity of the present disclosure can be used in cell-free, in vitro biosynthesis of cannabinoid compounds. Cell free cannabinoid biosynthesis methods utilizing the soluble prenyltransferase, NphB, from which the engineered polypeptides of the present disclosure are derived, are described in Valliere et al. "A bio-inspired cell-free system for cannabinoid production from inexpensive inputs," Nature Chemical Biology Vol. 16, December 2020, 1427-1433; and WO2020/028722A1, which is hereby incorporated by reference herein in its entirety. Indeed, the increased thermostability of the engineered NphB polypeptides of the present disclosure, including the exemplary polypeptides of Table 3, allows them to be incorporated directly into known cell-free cannabinoid biosynthesis methods. Moreover, using the engineered polypeptides of the present disclosure, the known cell-free cannabinoid biosynthesis methods can be carried out at higher temperatures resulting higher rates of conversion. Such uses of the engineered NphB polypeptides of the present disclosure for cell-free cannabinoid biosynthesis are described elsewhere herein and exemplified in the Examples.

As described herein, the engineered NphB polypeptides with increased thermostability of the present disclosure can be incorporated in any biosynthesis method requiring a prenyltransferase catalyzed biocatalytic step. Thus, in at least one embodiment, the engineered NphB polypeptides (e.g., exemplary polypeptides of Table 3) can be used in a method for preparing a cannabinoid compound of structural formula (I)

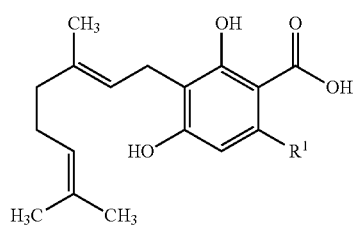
(I)

wherein, $R^1$ is C1-C7 alkyl. This biosynthetic method comprises contacting an engineered polypeptide of the present disclosure (e.g., polypeptide of any one of even-numbered SEQ ID NO: 6-50) under suitable reactions conditions, with a geranyl pyrophosphate (GPP) compound and a cannabinoid precursor compound of structural formula (II)

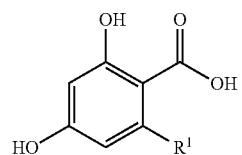
(II)

wherein, $R^1$ is C1-C7 alkyl.

Figure 2:
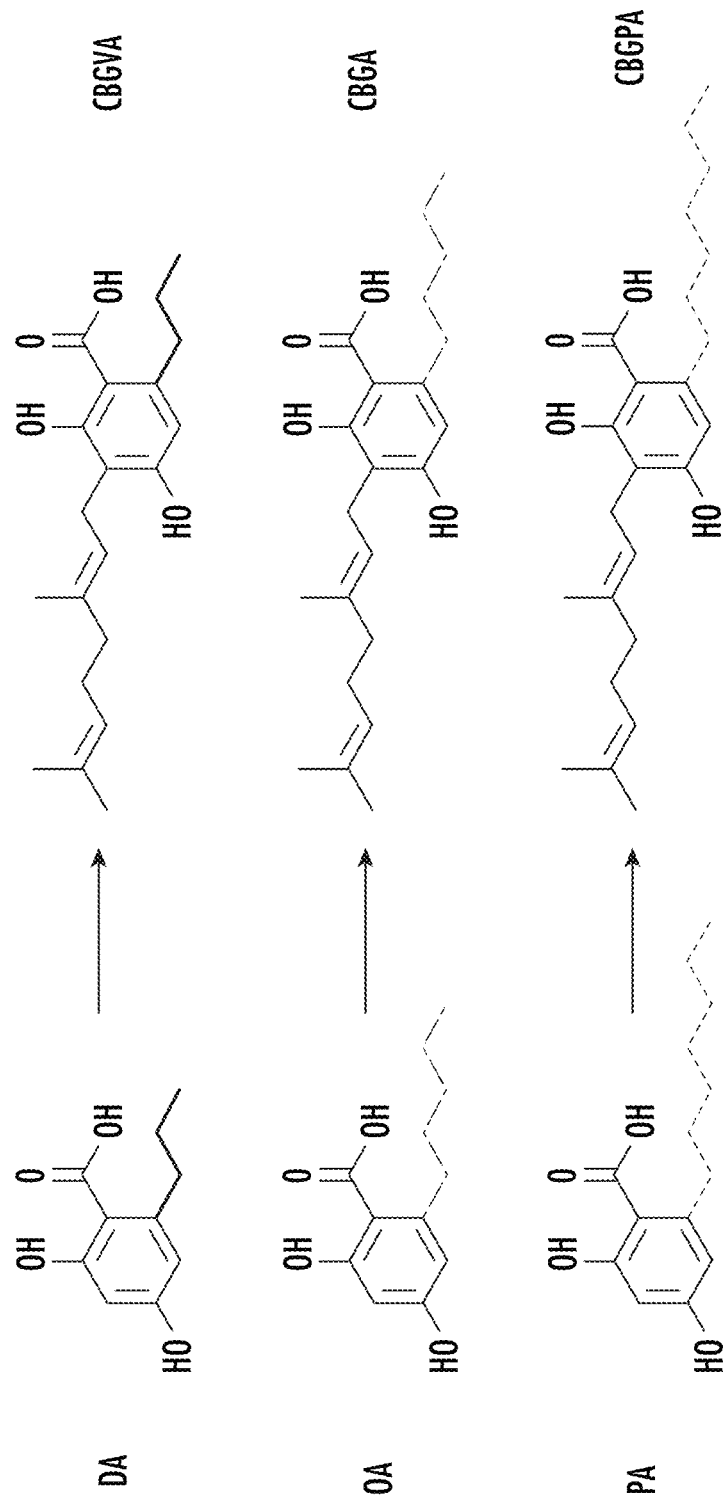
FIG. 2 depicts exemplary prenylation reactions producing the cannabinoids, CBGA, CBGVA, and CBGPA that are catalyzed by the engineered NphB prenyltransferases.

Three exemplary conversions of cannabinoid precursor compounds of structural formula (II) to cannabinoid compounds of structural formula (I) that are catalyzed by the engineered NphB polypeptides of the present disclosure are depicted in FIG. 2. The precursor compound substrate, divarinic acid (DA) can be converted to the cannabinoid compound product, cannabigerovarinic acid (CBGVA). The precursor compound substrate, olivetolic acid (OA) is converted to the cannabinoid compound product, cannabigerolic acid (CBGA). The precursor compound substrate, sphaerophorolic acid (PA) is converted to the cannabinoid compound product, cannabigerophorolic acid (CBGPA). It is contemplated that the engineered NphB polypeptides of the present disclosure will exhibit prenyltransferase activity with other cannabinoid precursor compounds that are structural analogs of PA, OA, and PA, including but not limited to the exemplary cannabinoid precursor compounds listed in Table 2.

Accordingly, in at least one embodiment of the method, the compound of structure formula (I) is cannabigerolic acid (CBGA) and the compound of structural formula (II) is olivetolic acid (OA). In at least one embodiment, the compound of structure formula (I) is cannabigerovarinic acid (CBGVA) and the compound of structural formula (II) is divarinic acid (DA). In at least one embodiment, the compound of structure formula (I) is cannabigerophorolic acid (CBGPA) and the compound of structural formula (II) is sphaerophorolic acid (PA).

The present disclosure contemplates ranges of suitable reaction conditions that can be used in the methods, including but not limited to ranges of pH, temperature, buffer, solvent system, substrate loading, polypeptide loading, co-substrate or co-factor loading, atmosphere, and reaction time. The present disclosure also contemplates that the methods comprising the biocatalytic conversion of a substrate compound of structural formula (II) to a product compound of structural formula (I) using an engineered prenyltransferase polypeptide of the disclosure can further comprise additional chemical or biocatalytic steps carried out on the product compound, product compound work-up, extraction, isolation, purification, and/or crystallization, each of which can be carried out under a range of conditions.

Further suitable reaction conditions for carrying out the biocatalytic conversion of a substrate compound of structural formula (II) to a product compound of structural formula (I) using an engineered prenyltransferase polypeptide described herein can be readily optimized by routine experimentation that includes, but is not limited to, contacting the engineered polypeptide and substrate under experimental reaction conditions of concentration, pH, temperature, solvent conditions, and detecting the production of the desired compound of structural formula (I), for example, using the methods described in the Examples provided herein.

The increased thermostability of the engineered prenyltransferase (PT) polypeptides of the present disclosure can also provide increased biosynthetic reaction lifetimes, which allows for the use of less enzyme, and/or allows for more complete enzymatic reactions resulting in higher product purity. Thus, it is contemplated that the use of the engineered prenyltransferase enzymes in a method for the conversion of a compound of structural formula (II) to a compound of structural formula (I) can result in the preparation of the compound of structural formula (I) in very high purity. Accordingly, in at least one embodiment, the engineered NphB polypeptides (e.g., exemplary polypeptides of Table 3) can be used in a biosynthetic process for preparing a cannabinoid compound of structural formula (I) with a purity of at least about 97%, at least about 98%, at least about 99%, at least about 99.5%, or even higher.

Generally, a biosynthetic reaction involving the prenyltransferase catalyzed conversion of a cannabinoid precursor compound of formula (II) to a cannabinoid product of formula (I) can be carried out in accordance with reaction conditions for cell-free biosynthesis of cannabinoids known in the art (see e.g., Valliere et al. 2020; or WO2020028722A1) or as described herein. However, in view of their increased thermostability of the engineered polypeptides of the present disclosure, it is contemplated that the suitable reaction conditions can include temperature of the reaction solution up to about 45° C. Thus, in some embodiments of the method, the suitable reaction conditions can include a temperature range of about 20° C. to about 45° C. In one embodiment, the suitable reaction conditions comprise a temperature of about 37° C.

It is also contemplated that the increased thermostability of the engineered polypeptides of the present disclosure can allow a range of substrate loading in the reaction. Thus, in some embodiments of the method of preparing a cannabinoid compound of structural formula (I), the suitable reaction conditions can comprise a cannabinoid precursor substrate loading of at least about 0.6 g/L, at least about 1.2 g/L, at least about 2 g/L, at least about 6 g/L, at least about 12 g/L, at least about 18 g/L, at least about 24 g/L, at least about 30 g/L or even greater. Specifically, where the cannabinoid precursor substrate is selected from OA, DA, and PA, the substrate loading can be at least about 0.6 g/L, at least about 1.2 g/L, at least about 2 g/L, at least about 6 g/L, at least about 12 g/L, at least about 18 g/L, at least about 24 g/L, at least about 30 g/L, or even greater.

The increased thermostability of the engineered polypeptides of the present disclosure can allow reactions to be carried out at higher temperatures, resulting in higher rates of biocatalytic conversion. Thus, it is contemplated that in some embodiments the prenyltransferase catalyzed conversion of a cannabinoid precursor compound of formula (II) to a cannabinoid product of formula (I) can be carried out with lower concentrations of the engineered NphB polypeptide. Accordingly, in at least one embodiment of the method, the suitable reaction conditions comprise a recombinant polypeptide concentration of about 0.1 g/L to about 5 g/L, or even lower concentration.

As noted elsewhere herein, suitable pH and buffer conditions for the biosynthesis of cannabinoids are known in the art, and can also be used with the engineered NphB polypeptides of the present disclosure. Accordingly, in at least one embodiment a method of producing a cannabinoid compound of structural formula (I) using the engineered polypeptides of the present disclosure, the suitable reaction conditions can comprise: (a) a pH of about 5.0 to about 11.0, or about 4.0 to 10.0; and/or a buffer solution of about 0.05 M Tris-Cl pH 8.0 to about 0.5 M Tris-Cl pH 8.0. In at least one embodiment, the suitable reaction conditions for preparing the cannabinoid compound, CBGA, comprise: olivetolic acid (OA), geranyl pyrophosphate (GPP), 0.1 M buffer (e.g., Tris), pH 8.0, and the recombinant polypeptide at 37° C. for at least 1 hour. It is contemplated that identical or very similar conditions for the biosynthetic production of CBGVA or CBGPA. Suitable reaction conditions for the various engineered polypeptides of the present disclosure can be easily determined using routine techniques for optimizing biocatalytic reaction conditions well-known to one of ordinary skill.

In at least one embodiment, the recombinant engineered NphB polypeptides of the present disclosure can be used in a biosynthetic reaction for the production of a cannabinoid compound, or a composition comprising a cannabinoid compound. It is contemplated that the produced cannabinoid compound can include, but is not limited to, the cannabinoid compounds of Table 2. Accordingly, in at least one embodiment, the biosynthetic reaction can be used for production of a cannabinoid compound selected from cannabigerolic acid (CBGA), cannabigerol (CBG), cannabidiolic acid (CBDA), cannabidiol (CBD), $\Delta^9$-tetrahydrocannabinolic acid ($\Delta^9$-THCA), $\Delta^9$-tetrahydrocannabinol ($\Delta^9$-THC), $\Delta^8$-tetrahydrocannabinolic acid ($\Delta^8$-THCA), $\Delta^8$-tetrahydrocannabinol ($\Delta^8$-THC), cannabichromenic acid (CBCA), cannabichromene (CBC), cannabinolic acid (CBNA), cannabinol (CBN), cannabidivarinic acid (CBDVA), cannabidivarin (CBDV), $\Delta^9$-tetrahydrocannabivarinic acid ($\Delta^9$-THCVA), $\Delta^9$-tetrahydrocannabivarin ($\Delta^9$-THCV), cannabidibutolic acid (CBDBA), cannabidibutol (CBDB), $\Delta^9$-tetrahydrocannabutolic acid ($\Delta^9$-THCBA), $\Delta^9$-tetrahydrocannabutol ($\Delta^9$-THCB), cannabidiphorolic acid (CBDPA), cannabidiphorol (CBDP), $\Delta^9$-tetrahydrocannabiphorolic acid ($\Delta^9$-THCPA), $\Delta^9$-tetrahydrocannabiphorol ($\Delta^9$-THCP), can nabichromevarinic acid (CBCVA), cannabichromevarin (CBCV), cannabigerovarinic acid (CBGVA), cannabigerovarin (CBGV), cannabicyclolic acid (CBLA), cannabicyclol (CBL), cannabielsoinic acid (CBEA), cannabielsoin (CBE), cannabicitranic acid (CBTA), cannabicitran (CBT), and any combination thereof. In at least one embodiment, a recombinant host cell of the present disclosure can be used to produce a cannabinoid selected from cannabigerolic acid (CBGA), cannabidiolic acid (CBDA), cannabichromenic acid (CBCA), and any combination thereof.

In at least one embodiment, the present disclosure provides a cell-free biosynthetic reaction scheme for the production of a range of cannabinoids and other prenylated products using the recombinant polypeptides of the present disclosure having prenyltransferase activity and increased thermostability (e.g., recombinant polypeptides of Table 3). In at least one embodiment, this biosynthetic reaction scheme provides a pathway for production of the prenyl donor substrate, GPP, and a pathway for the production of the prenyl acceptor substrate, e.g., a cannabinoid precursor such as OA, DA, or PA. Such a cell-free biosynthetic reaction scheme using the highly soluble, thermostable engineered prenyltransferase polypeptides of the present disclosure has the benefit of providing biocatalytic conversions without the complexities required by the use of in vivo systems (e.g., problems of toxicity of GPP at high levels or low uptake of OA by yeast). Further, the use of a cell-free biosynthetic system can simplify further optimization of the biosynthesis system, such as modification or addition pathway enzymes and modification of reagents or co-factors.

As illustrated by the exemplary biosynthetic reaction scheme of FIG. 1, the input compounds hexanoyl-CoA and malonyl-CoA can be used as substrates in a cell-free biosynthesis pathway for production of the cannabinoid precursor compound, olivetolic acid (OA). This biosynthesis begins with the condensation of hexanoyl-CoA and malonyl-CoA catalyzed by olivetol synthase (OLS) (BAG14339.1 from C. sativa) to generate 3,5,7-trioxododecanoyl-CoA. The enzyme olivetolic acid cyclase (OAC) (AFN42527.1 from C. sativa) cyclizes 3,5,7-trioxododecanoyl-CoA to OA. Similar biosynthesis pathways can lead to the OA analogs, DA, and PA. The prenyl donor substrate, GPP, is produced via terpene biosynthesis enzyme pathways. In some instances, the enzymatic pathway steps may utilize co-factors (e.g., NAD(P)H, ATP/ADP etc.). Table 4 provides a list of exemplary enzymes that can be used in a cell-free biosynthesis system incorporating the recombinant prenyltransferase polypeptides of the present disclosure.

TABLE 4

Enzymes used in the enzymatic platform

| Enzyme Abbreviation | Enzyme | Source Organism | Accession # |
|---|---|---|---|
| AAE3 | Acyl Activating Enzyme 3 | C. sativa | AFD33347.1 |
| MatB | Malonyl-CoA Synthetase | R. plaustris | CAE25665.1 |
| mdcA | Malonate Decarboxylase α subunit | Geobacillus sp. 44B | OQO99201.1 |
| PTA | Phosphotransacetylase | G. stearothermophilus | WP_053532564 |
| OLS | Olivetol Synthase | C. sativa | BAG14339.1 |
| OAC | Olivetolic Acid Cyclase | C. sativa | AFN42527.1 |
| ADK | Adenylate Kinase | G. thermodenitrificans | ABO65513 |
| Ppase | Pyrophosphatase | G. stearothermophilus | O05724 |
| CPK | Creatine Kinase | Rabbit Muscle | Sigma Aldrich |
| ThiM | Hydroxyethylthiazole kinase | E. coli | NP_416607 |
| IPK | Isopentenyl Kinase | M. jannaschii | WP_01069535 |
| IDI | Isopentyl diphosphate isomerase | E. coli | NP_417365 |
| FPPS S82F | Farnesyl Pyrophosphate Synthase | G. stearothermophilus | KOR95521 |

The cell-free biosynthetic reactions using the recombinant polypeptides of the present disclosure can be carried out using a range of biocatalytic reaction methods. For example, the pathway enzymes can be purchased commercially, mixed in a suitable buffer with the recombinant prenyltransferase polypeptides of the present disclosure, and then the solution is exposed to the suitable substrate, and incubated under conditions suitable for production of the desired cannabinoid compound. In some embodiments, it is contemplated that one or more of the pathway enzymes can be bound to a solid support. It is also contemplated that one or more of the pathway enzymes can be expressed using phage display or other surface expression system and, for example, fixed in a fluid pathway corresponding to points in the metabolic pathway's cycle.

It is also contemplated that one or more polynucleotides encoding the one or more pathway enzymes can be cloned into one or more host cells under conditions providing expression of the enzymes. The host cells can then be lysed and the lysate comprising the one or more enzymes (including the recombinant prenyltransferase polypeptides) can be combined with a suitable buffer and substrate (and one or more additional enzymes of the pathway, if necessary) to produce the desired cannabinoid. Alternatively, the enzymes can be isolated from the lysed preparations with or without heat treatment and then recombined in an appropriate buffer.

In one embodiment, the pathway enzymes, other than the thermostable prenyltransferase polypeptides of the present disclosure are derived from thermophilic microorganisms. The microorganisms are cultured to express the thermostable enzymes, then lysed, and the culture lysate heated to a temperature wherein the thermostable enzymes of the pathway remain active while other enzymes become inactive. Such a heat purified lysate preparation can then be used together with the thermostable prenyltransferase polypeptides of the present disclosure in a cell-free biosynthesis reaction to produce a desired cannabinoid compound.

In addition to the cell-free processes described herein, it is also contemplated that the engineered prenyltransferases of the present disclosure can be introduced into a recombinant host cell for in vivo production of compounds that require prenyltransferase activity in their biosynthesis (e.g., cannabinoids). Accordingly, in at least one embodiment of a method for producing a cannabinoid, a heterologous nucleic acid encoding a recombinant polypeptide having prenyltransferase activity and increased thermostability, (e.g., an exemplary engineered polypeptide of Table 3) can be functionally incorporated into a recombinant host cell (e.g., a yeast cell) via transformation or stable genomic integration (e.g., using CRISP-Cas9 type integration). The recombinant host cell can then be used in a biocatalytic process that utilizes the prenyltransferase activity of the recombinant polypeptide expressed by the host cell for the catalytic prenylation of a substrate, e.g., the prenylation of OA with GPP to produce CBGA. In at least one embodiment, the recombinant host cell can further comprise a full pathway of enzymes capable of producing precursors substrates (e.g., GPP, olivetolic acid), and/or downstream products (e.g., CBDA) in addition to the recombinant polypeptide with prenyltransferase activity of the present disclosure. It is contemplated that a recombinant host cell comprising a heterologous nucleic acid encoding a recombinant polypeptide of the present disclosure can provide improved biosynthesis of a cannabinoid (e.g., CBGA) in terms of titer, yield, and production rate, due to the improved thermostability of the expressed prenyltransferase activity.

Accordingly, in at least one embodiment, the present disclosure provides a method of producing a cannabinoid, wherein the method comprises: (a) culturing in a suitable medium a recombinant host cell that comprises a functionally incorporated heterologous polynucleotide that encodes an engineered prenyltransferase polypeptide of the present disclosure; and (b) recovering the product (e.g., cannabinoid) produced by the prenyltransferase activity expressed by the cell. In at least one embodiment; the method of producing the compound (e.g., cannabinoid) can further comprise contacting a cell-free extract of the culture containing the produced cannabinoid with a biocatalytic reagent or chemical reagent capable of converting the cannabinoid to a cannabinoid derivative. In at least one embodiment, the biocatalytic reagent is an enzyme capable of converting the produced cannabinoid to a different cannabinoid or a cannabinoid derivative compound. In at least one embodiment, the chemical reagent is capable of chemically modifying the produced cannabinoid to produce a different cannabinoid or a cannabinoid derivative compound. In at least one embodiment of the method for producing a cannabinoid, the method can further comprise contacting a cell-free extract of the culture containing the produced cannabinoid with a biocatalytic reagent or chemical reagent.

It is contemplated that the cannabinoid, or cannabinoid derivative produced using the methods of the present disclosure can be produced and/or recovered from the reaction in the form of a salt. In at least one embodiment, the recovered salt of the cannabinoid, cannabinoid precursor, cannabinoid precursor derivative, or cannabinoid derivative is a pharmaceutically acceptable salt. Such pharmaceutically acceptable salts retain the biological effectiveness and properties of the free base compound.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Preparation of Engineered NphB Prenyltransferase Variants with Increased Thermostability This example illustrates the preparation of recombinant polypeptide variants with prenyltransferase activity and increased thermostability by site-directed mutagenesis of a parent polypeptide, NphBM31, which has the amino acid sequence of SEQ ID NO: 4. NphBM31 has the amino acid sequence "backbone" of the wild-type NphB enzyme (SEQ ID NO: 2) with two amino acid substitutions: Y288V and A232S. A further engineered version of NphBM31, referred to as NphBM31s, has the following 10 amino acid substitutions relative to NphBM31 (SEQ ID NO: 4): M14I, Y31W, T69P, T77I, T98I, S136A, E222D, G224S, N236T, and G297K. This NphBM31s (SEQ ID NO: 26) variant exhibits increased thermostability relative to the NphBM31, exhibiting a Tm increased by about 8° C. (Tm about 51° C. and a $T_{1/2}$ of about 20 min at 51° C.). (See e.g., Valliere et al. "A bio-inspired cell-free system for cannabinoid production from inexpensive inputs," Nature Chemical Biology Vol. 16, December 2020, 1427-1433). In this example, the variants have been screened for thermostability relative to the recombinant polypeptide, NphBM31s of SEQ ID NO: 26.

Materials and Methods

A. Thermostable Variant Design

To further increase thermostability of NphB beyond the thermostable variant NphBM31s (SEQ ID NO: 26), chain A of the crystal structure of the wild-type NphB (Orf2) from *Streptomyces* sp. CL190 (RCSB Protein Data Bank 1ZB6) was reanalyzed to identify potentially thermostabilizing amino acid substitutions. The 1ZB6 crystal structure was analyzed for the following two types of motifs: (1) unstructured loops 5 amino acids long or greater that contain amino acids A, S, or T; and (2) buried T or Y residues that had an unsatisfied H-bond between the OH group and another amino acid side-chain or water. For motifs of type (1), the A, S, or T amino acid residues in the loops were mutated to P. For the motifs of type (2), the T residue was mutated to V or I, and the Y residue was mutated to F. A total of 8 positions in motifs were identified for thermostabilizing amino acid substitutions. Additionally, one mutation, V91I, appeared spontaneously during cloning and was also included in the analysis. The specific amino acid substitutions introduced for screening are summarized in Table 5.

TABLE 5

| Motif type | Amino Acid Position | Amino Acid Substitution |
| --- | --- | --- |
| Loop (1) | A24 | A24P |
| Buried (2) | V48 | V48I |
| Loop (1) | A86 | A86P |
| Spontaneous | V91 | V91I |
| Buried (2) | T120 | T120I |
| Loop (1) | T126 | T126P |
| Loop (1) | A144 | A144S |
| Buried (2) | T163 | T163I |
| Buried (2) | Y167 | Y167F |
| Loop (1) | A181 | A181P |
| Loop (1) | V200 | V200E |
| Buried (2) | T269 | T269V |
| Buried (2) | T275 | T275V |

The amino acid substitutions were introduced individually by site-directed mutagenesis as described below. Increased thermostability was confirmed due to the presence of single point mutations in the NphBM31 background (SEQ ID NO: 4) and the NphBM31s background (SEQ ID NO: 26). Stabilizing single point mutations were then combined and further screened for stability and activity.

B. Gene Synthesis and Expression

Mutant genes encoding the NphBM31 variants were obtained through site directed mutagenesis using a mutagenic primer containing the desired mutation. The NphBM31 gene was used as the template to introduce mutations via polymerase chain reaction (PCR) using the mutagenic primer. Mutations were confirmed by Sanger sequencing. Following confirmation, expression of the recombinant NphBM31 variants was carried out in *E. coli*.

The clonal gene in the pET28a expression vector was transformed into BL21-Gold (DE3) competent cells using standard chemical transformation methods. A single colony was used to inoculate 4 mL LB+kanamycin (50 mg/mL), which was grown at 37° C. and 250 rpm. After 12 hours, the overnight was used to inoculate 1 L LB+kanamycin (50 mg/mL). At an $OD_{600}$ of ~0.6, the culture was induced with the addition of 0.4 mM isopropyl β-d-1-thiogalactopyranoside (IPTG) and grown at 18° C. and 250 rpm. After 12 hours, protein purification was carried out using standard Ni-NTA methods.

C. Prenyltransferase Activity Assay

To assay for prenyltransferase activity, 10 μL of the NphB variant polypeptide samples at 1 mg/mL concentration were added to 40 μL reaction mix containing 2.5 mM olivetolic acid (OA), 3.75 mM GPP, 3 mM $MgCl_2$, in 100 mM Tris at pH 8.0. The prenyltransferase reactions (50 μL final) were allowed to proceed for 1 hour at 25° C. and then quenched at by adding 950 μL methanol. Protein precipitate was removed by centrifugation (3 min at 16,000 g), and CBGA production analyzed by HPLC.

D. Thermostability Assay

Thermostability relative to the parent NphBM31 (SEQ ID NO: 4) or NphBM31s (SEQ ID NO: 26) was determined by first measuring the thermal inactivation profile of the parent polypeptide by incubating 50 μL of 1 mg/mL protein in 50 mM Tris pH 8.0 at different temperatures for 30 min using the temperature gradient setting on an Eppendorf Mastercycler ProS PCR cycler. The temperature incubation was performed for 30 min at the following temperatures: 30.0° C., 33.6° C., 38.4° C., 41.0° C., 43.8° C., 46.2° C., 50.2° C., 52.4° C., 55.2° C., and 60.0° C. Following temperature incubation, samples were spun down and residual prenyltransferase activity measured for the conversion of OA and GPP to CBGA as described above. Once the Tm of the parent NphBM31 was established (~43° C.), the parent NphBM31 and mutant variants were then incubated at 42.8° C. for 0 min, 30 min, 60 min, and 180 min. Following temperature incubation, samples were spun down and residual prenyltransferase activity at each time point was measured for the conversion of OA and GPP to CBGA by assaying 10 µL of sample as described above.

To determine the effect of incorporating additional stabilizing mutations in the NphBM31s (SEQ ID NO: 26) variant, a similar temperature profile from 30.0° C. to 60.0° C. was performed to establish the Tm of NphBM31s. Once this Tm was established (~51° C.), NphBM31s and the variants derived from it were then incubated at 53.9° C. for 0 min, 30 min, 60 min, and 180 min. Following temperature incubation, samples were spun down and residual prenyltransferase activity at each time point was measured for the conversion of OA and GPP to CBGA was measured by assaying 10 µL of sample as described above.

Results

Figure 3A:
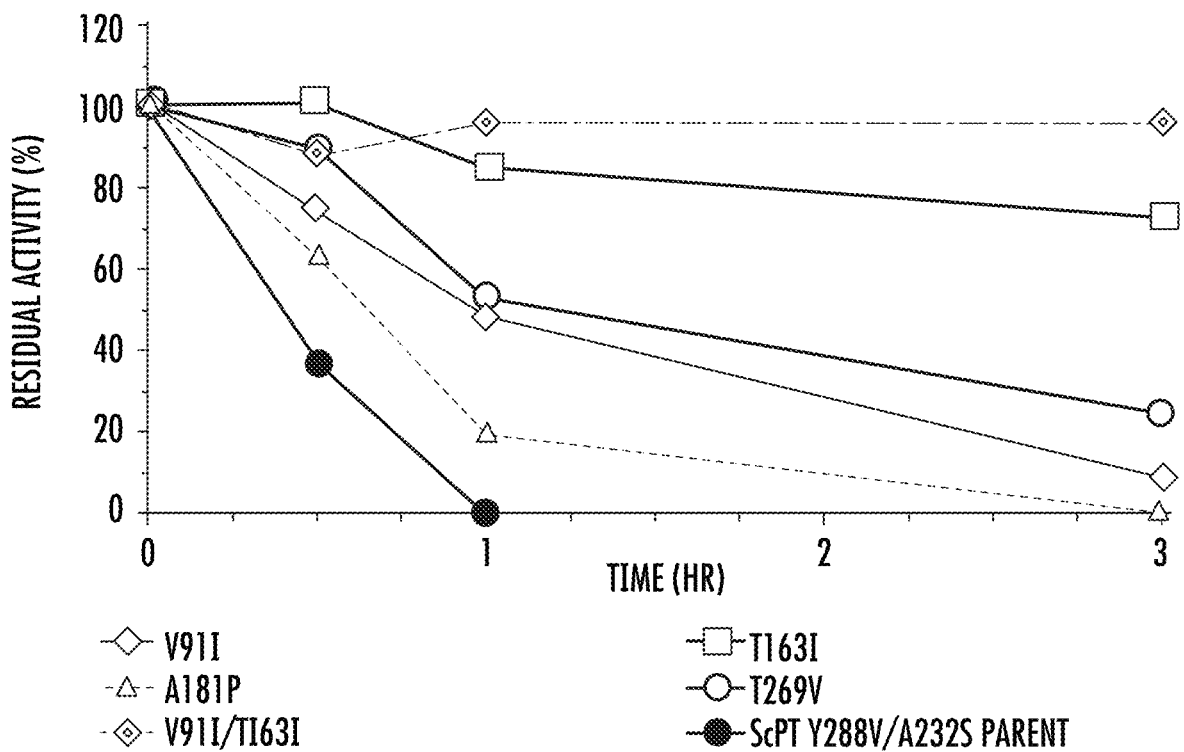
FIG. 3A and FIG. 3B depict plots of thermostability results for exemplary single amino acid substitution engineered variants of the NphBM31 (SEQ ID NO: 4) parent polypeptide as described in Example 1.
Figure 3B:
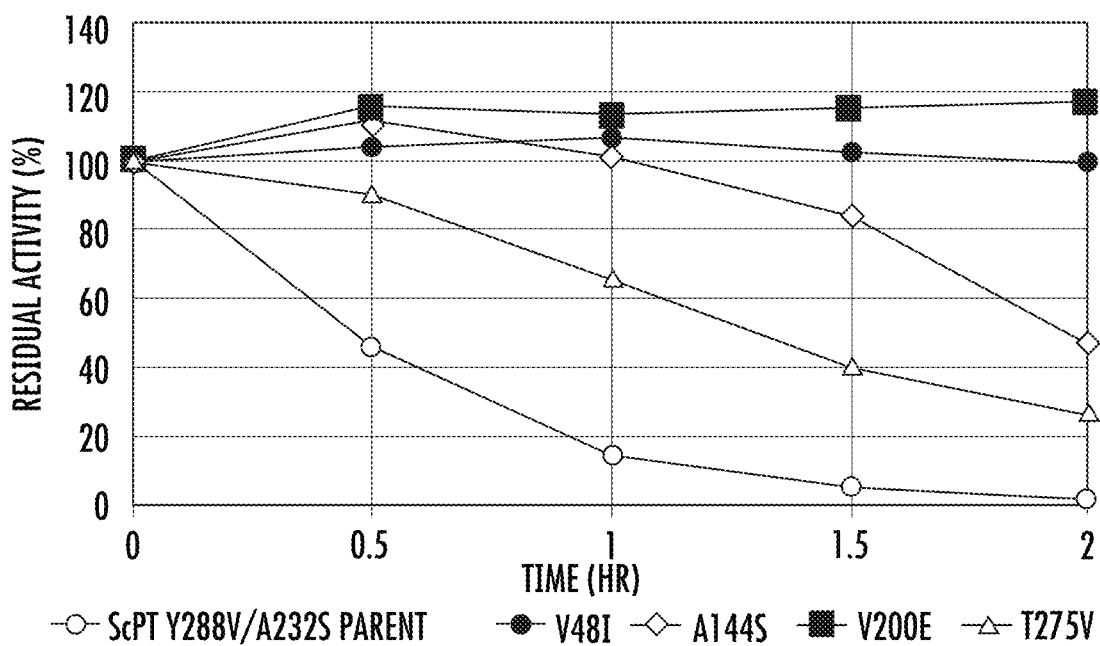

The $T_{1/2}$ of the parent, NphBM31 (SEQ ID NO: 4) at 42.9° C. is 20 minutes. As shown by the results depicted in FIG. 3A and FIG. 3B, introduction of the following single point mutations in the NphBM31 polypeptide resulted in a significant increase of $T_{1/2}$: V91I, T163I, A181 P, or T269V. In the case of T163I and the double substitution, V91I/T163I, the $T_{1/2}$ is significantly increased from 20 minutes to 4.6 hours and 21.6 hours, respectively.

Figure 4A:
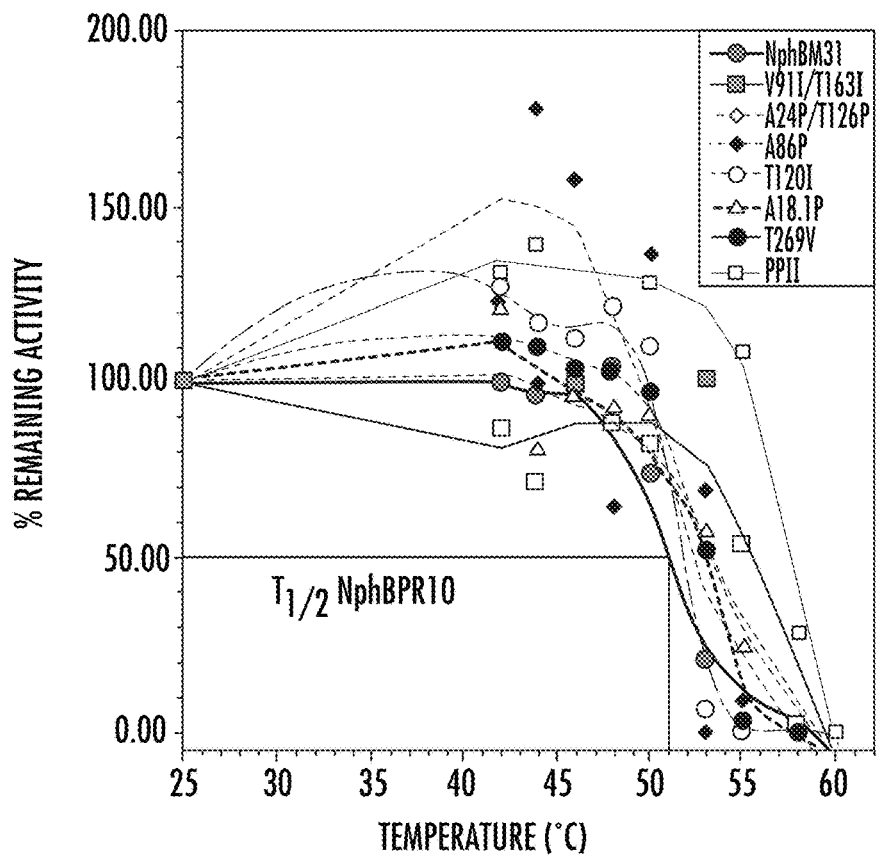
FIG. 4A and FIG. 4B depict plots of thermostability results for exemplary engineered variants of the NphBM31s (SEQ ID NO: 16) parent polypeptide as described in Example 1.
Figure 4B:
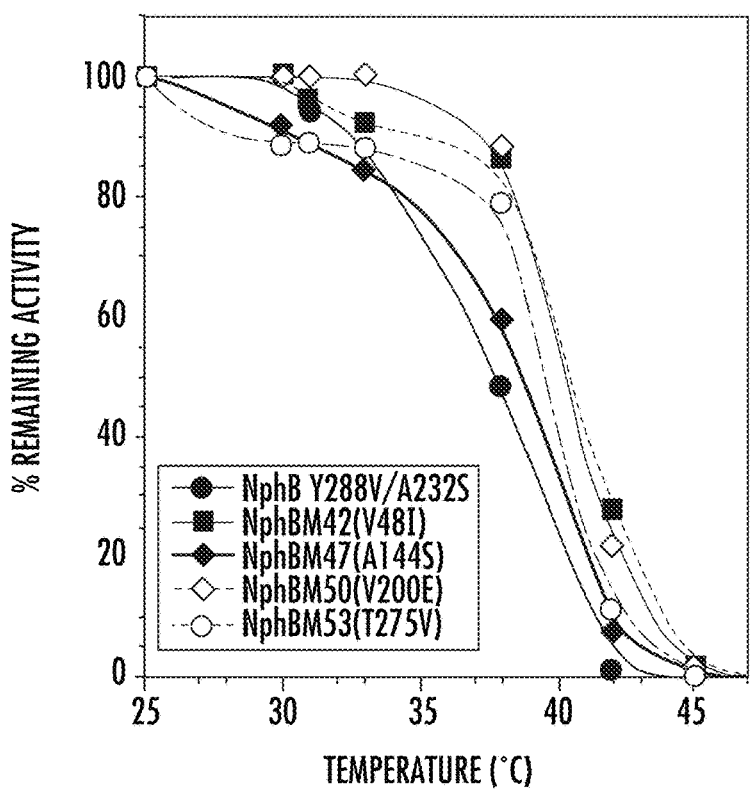
Figure 5:
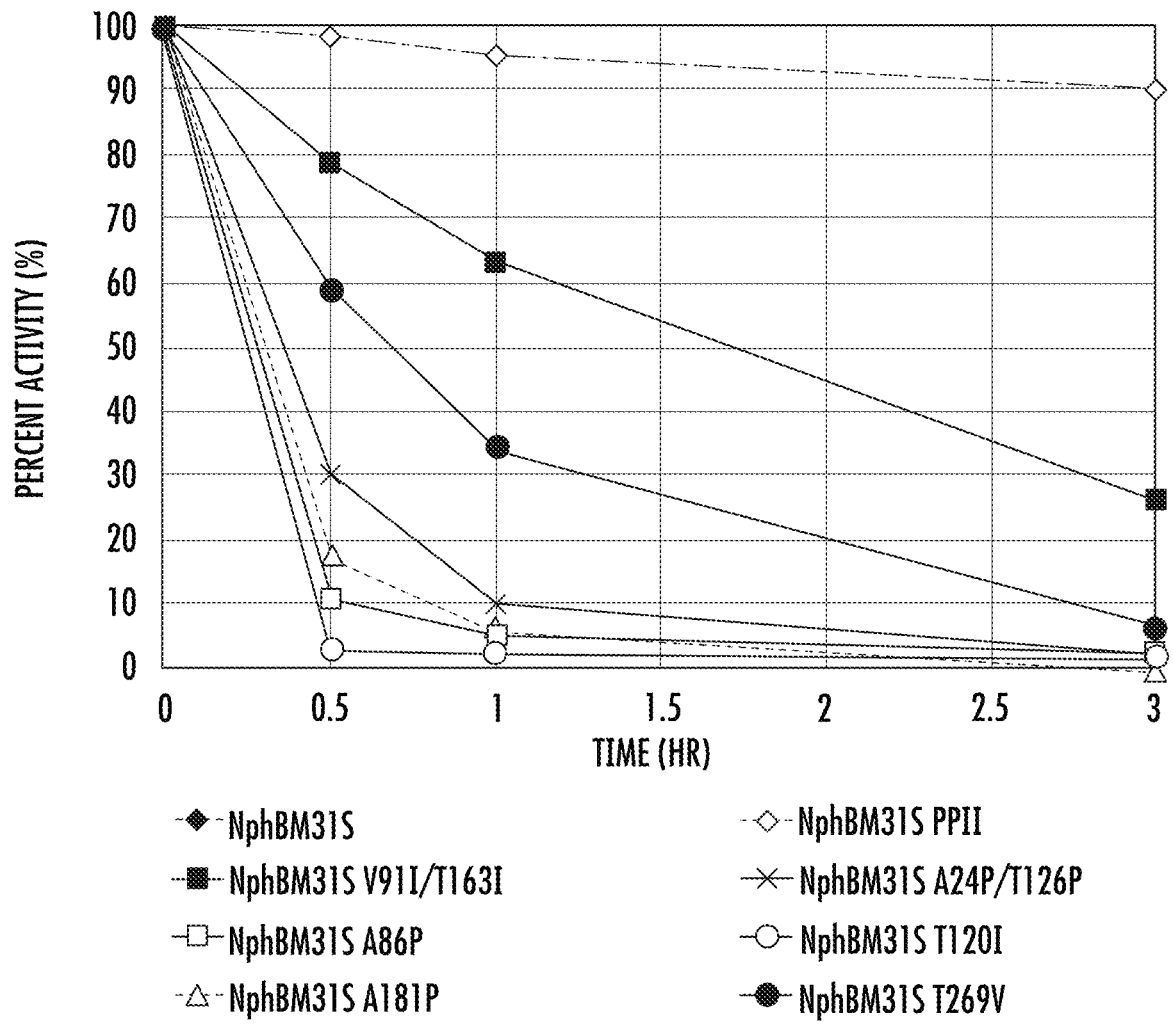
FIG. 5 depicts plot of thermostability results for exemplary engineered variants of the NphBM31s (SEQ ID NO: 16) parent polypeptide as described in Example 1.

Furthermore, as shown by the results depicted in FIG. 4A and FIG. 4B when the corresponding single and combined point mutations were introduced into the NphBM31s variant polypeptide (SEQ ID NO: 26). A significant increase in $T_{1/2}$ was observed from 51° C. to 58° C. was seen when comparing NphBM31s (SEQ ID NO: 26) with NphBM33 (SEQ ID NO: 48), which has the four amino acid "PPII" substitution: A24P, V91I, T126P, T163I. FIG. 5 depicts results showing the improved heat stability of the variant polypeptides of NphBM31s at a temperature of 53.8° C. over a time course of 3 h.

Example 2: Heat Purification of Thermostable NphB Prenyltransferase Variant

This example illustrates the purification of the NphB polypeptide variants of Example 1 using a step of heating at 65° C. for 30 min.

Materials and Methods

Expression of the recombinant thermostable variants of NphBM31s (SEQ ID NO: 26) in *E. coli* was carried out as follows. The clonal gene in the pET28a expression vector was transformed into BL21-Gold (DE3) competent cells using standard chemical transformation methods. A single colony was used to inoculate 4 mL LB+kanamycin (50 mg/mL), which was grown at 37° C. and 250 rpm. After 12 hours, the overnight was used to inoculate 1 L LB+kanamycin (50 mg/mL). At an $OD_{600}$ of ~0.6, the culture was induced with the addition of 0.4 mM isopropyl β-d-1-thiogalactopyranoside (IPTG) and grown at 37° C. and 250 rpm. After 12 hours, cells were harvested by centrifugation at 4000×g and resuspended in 3% of the initial culture volume with 25 mM Tris-Cl pH 8.0, 200 mM NaCl. Resuspended cells were sonicated at room temperature followed by centrifugation at 15000×g to pellet cell debris. The supernatant containing soluble protein was then subjected to various heat treatments at 25° C., 55° C., or 65° C. for 45 minutes. Heat denatured protein was removed by centrifugation at 15000×g for 5 minutes. The remaining folded, soluble protein was then analyzed by SDS-PAGE to assess the ability to use heat treatment as a purification strategy.

Results

Figure 6:
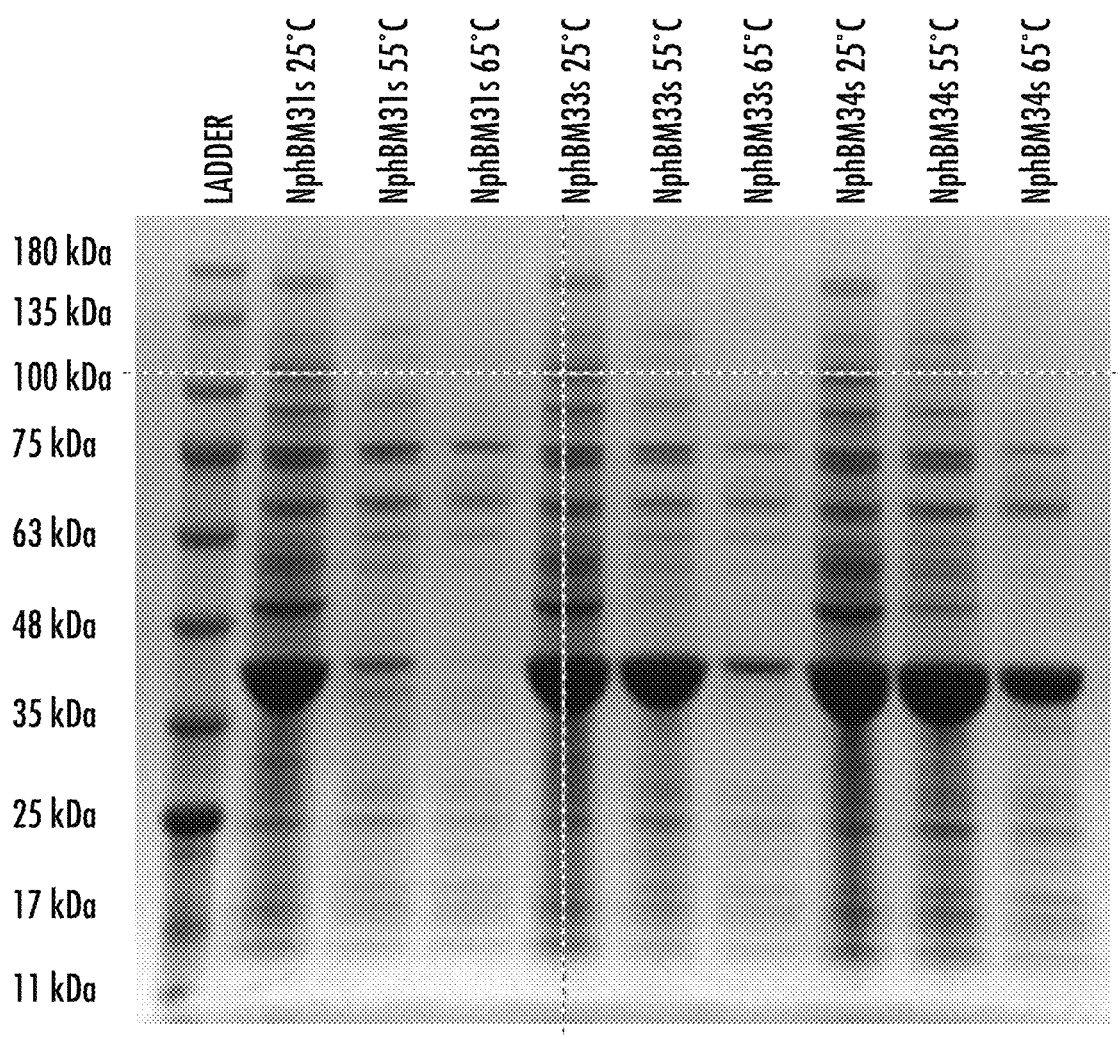
FIG. 6 depicts SDS-PAGE images showing that increased thermostability of exemplary engineered variants of NphBM31 allow for facile heat purification as described in Example 2.

As shown by the gel images depicted in FIG. 6, the original parent, NphBM31s (SEQ ID NO: 26) is mostly denatured following heat treatment for 45 minutes at 55° C. By comparison, very little denaturation can be seen when treating NphBM33s (SEQ ID NO: 48) or NphBM34s SEQ ID NO: 50) for 45 minutes at 55° C. In the case of NphBM34s (SEQ ID NO: 50), at least 50% of the soluble protein remains folded and soluble at 55° C. while nearly all the background *E. coli* proteins are denatured. This shows that heat treatment can be a viable method of isolation for NphBM33s or NphBM34s but not NphBM31s.

Figure 7:
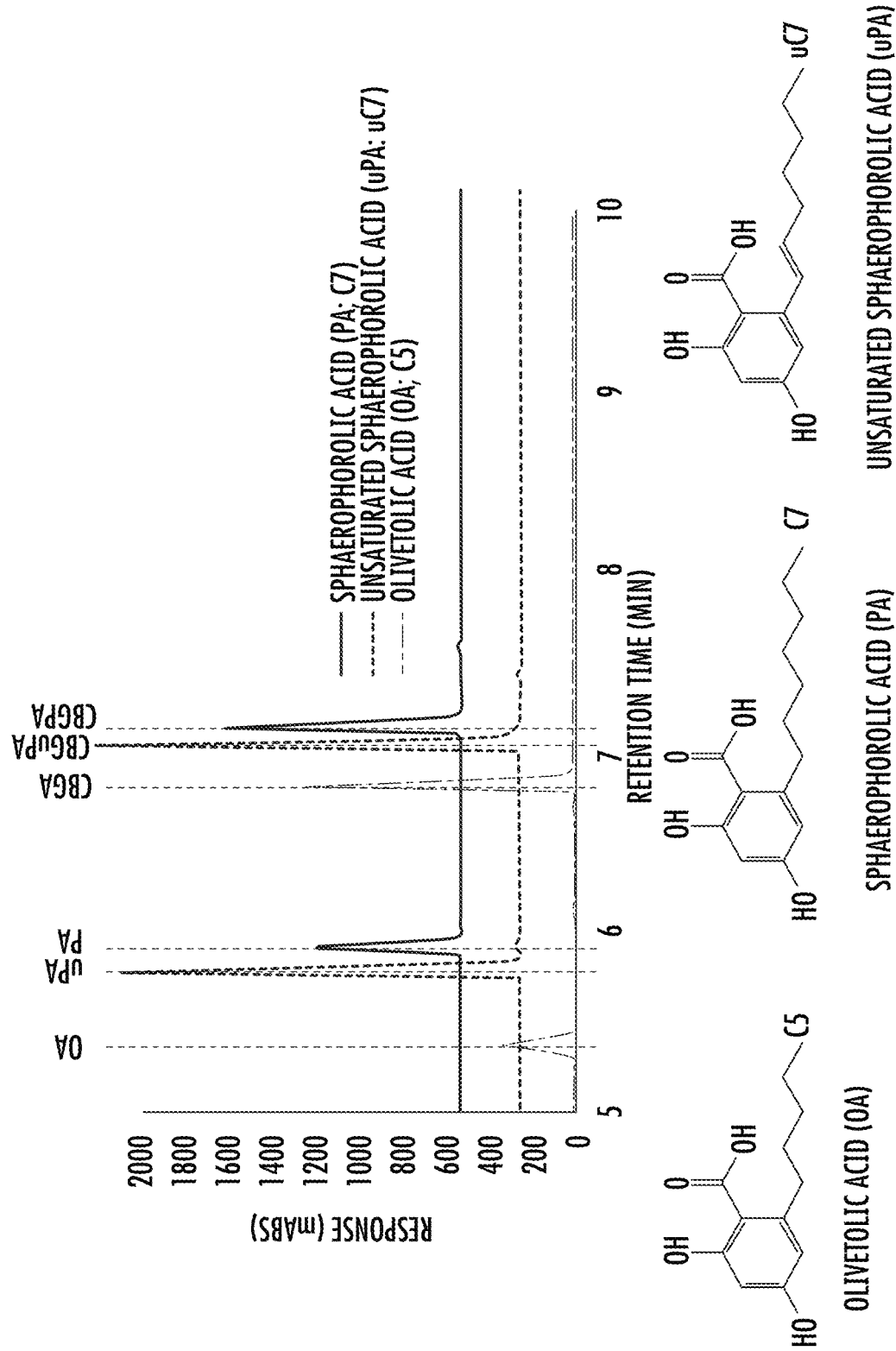
FIG. 7 depicts chromatographic plots showing that exemplary engineered variants of NphBM31 exhibit the ability to use the cannabinoid precursor compounds, olivetolic acid (OA), sphaerophorolic acid (PA), and unsaturated sphaerophorolic acid (uPA), to produce the corresponding cannabinoid products, CBGA, CBGPA, and CBGuPA, in a cell-free biosynthesis system, as described in Example 3.

Example 3: Use of Thermostable NphB Prenyltransferase Variant in a Cell-Free Biosynthesis System for Production of CBGA Derivatives This example illustrates the use of the thermostable NphB polypeptide variants of Example 1 in a cell-free biosynthesis of the cannabinoid, CBGA, or the C7 cannabinoids, CBGPA or CBGuPA, the structures of which are depicted in FIG. 7.

Materials and Methods

To assay for enzyme activity, 10 µL of NphB variant polypeptide samples at 10 mg/mL concentration were added to 100 µL reaction mix containing 2.5 mM olivetolic acid (OA) or the derivative substrates, sphaerophorolic acid (PA), unsaturated sphaerophorolic acid (uPA), 3.75 mM GPP, 3 mM $MgCl_2$, in 100 mM Tris at pH 8.0. The prenyltransferase reactions (150 µL final) were allowed to proceed for 16 hours at 25° C. and then quenched at by adding 950 µL methanol. Protein precipitate was removed by centrifugation (3 min at 16,000 g), and CBGA or derivative production analyzed by HPLC.

Results

As shown by the exemplary traces depicted in FIG. 7, when alternative substrates with increasing alkyl chain length and/or degree of unsaturation are fed to the engineered NphB variant polypeptide, the three different cannabinoid precursor substrates, OA, PA and uPA are able to be prenylated using GPP.

Example 4: Use of Thermostable NphB Prenyltransferase Variant in a Cell-Free Biosynthesis System at Increased Temperature This example illustrates the use of the thermostable NphB polypeptide variants of Example 1 in a cell-free biosynthesis for the cannabinoids, CBGA, CBGPA, and derivatives. The increased thermostability of the engineered NphB variants allows for cell-free biosynthesis at a higher temperature with longer prenyltransferase activity lifetime resulting in higher overall product yield and efficiency. Specifically, we show that use of engineered NphB variants allows higher conversion of OA and GPP to CBGA at increased temperature.

Materials and Methods

To assay for enzyme activity, 10 mL of NphB variant polypeptide samples at 10 mg/mL concentration were added to a 100 µL of reaction mix containing (final) 25 mM Olivetolic acid (OA), 25 mM GPP, 10 mM MgCl₂, and 40 mg/mL BSA in 100 mM Tris at pH 8.0. The prenyltransferase reactions were allowed to proceed for 24 hours at 42° C. After 24 hours, 50 mL aliquots of each sample were quenched by adding 950 mL methanol. Protein precipitate was removed by centrifugation (3 min at 16,000 g), and CBGA or derivative production analyzed by HPLC.

Results

Figure 8:
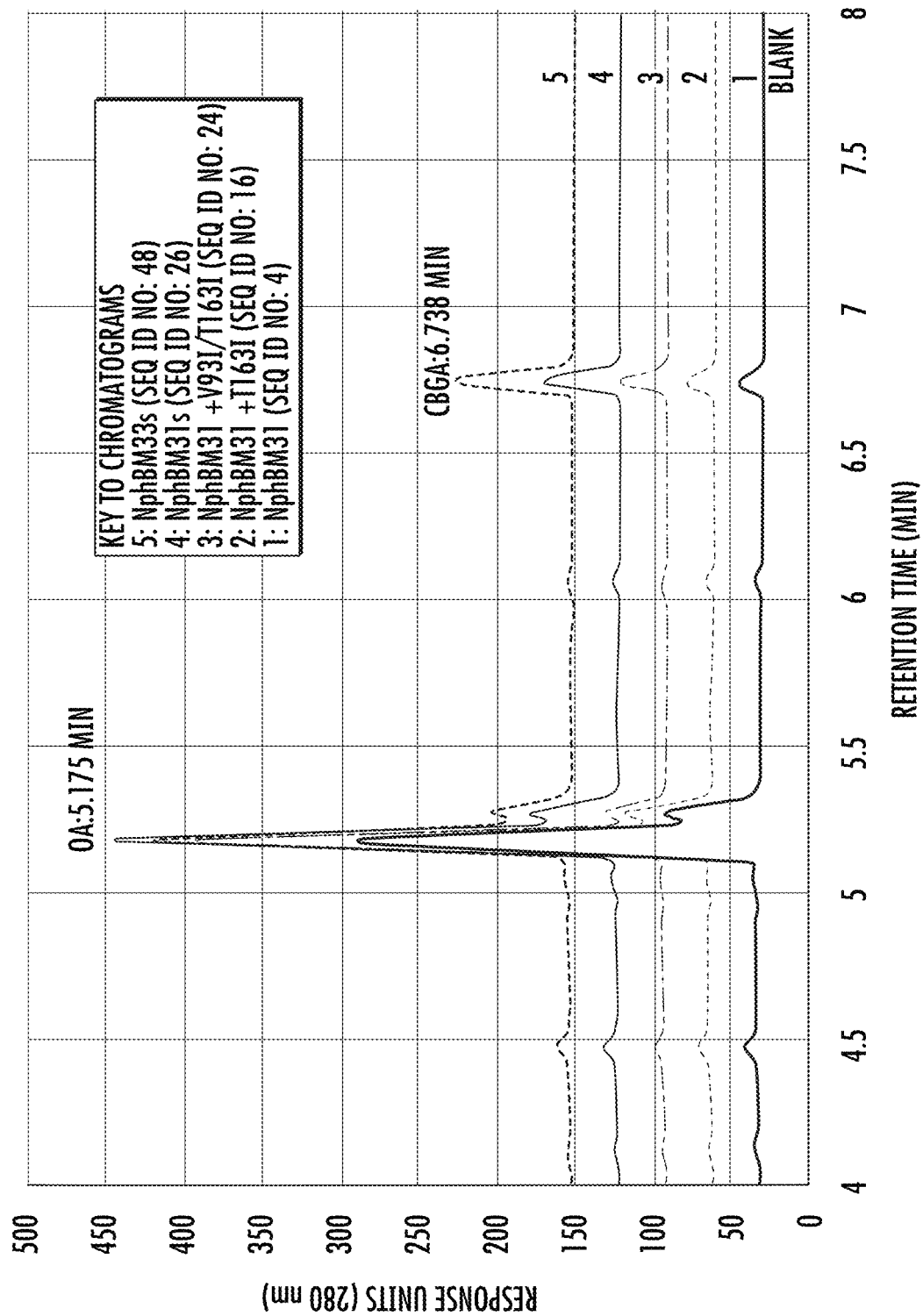
FIG. 8 depicts chromatographic plots showing that exemplary engineered variants of NphBM31 exhibit the ability to convert OA and GPP to the cannabinoid product, CBGA, at an elevated temperature of 42° C. in a cell-free biosynthesis system, as described in Example 4.

As shown by the traces depicted in FIG. 8, when cell-free reactions containing NphB Y228V/A232S or its thermostable variants are incubated at an elevated temperature of 42° C., OA and GPP are converted to CBGA. When the NphBM31 (SEQ ID NO: 4) variants containing thermostabilizing mutations T163I (SEQ ID NO: 16), V91I/T163I (SEQ ID NO: 24), or the NphBM31s variant, "NphBM33s" which includes the thermostabilizing mutations V91I/T163I/A24P/T126P (SEQ ID NO: 48) are used, increased conversion of OA and GPP to CBGA is seen. Alternative substrates with increasing alkyl chain length and/or degree of unsaturation are fed to the NphB variant, the substrates are able to be prenylated using GPP.

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

SEQUENCE LISTING

```
Sequence total quantity: 58
SEQ ID NO: 1             moltype = DNA  length = 924
FEATURE                  Location/Qualifiers
source                   1..924
                         mol_type = genomic DNA
                         organism = Streptomyces sp.
SEQUENCE: 1
atgtccgagg ccgcagatgt agaacgcgtt tacgcagcta tggaggaagc cgcagggctg   60
ctgggggtgg cgtgtgctcg cgacaaaatc tatcccttc tttcgacgtt tcaggacaca  120
ctggtagaag gaggctccgt tgttgtgttt agcatggctt ccggtcgtca cagtacagag  180
cttgatttct caatttccgt acccacgtcg catgggacc cctatgccac tgttgtggag  240
aagggttgt ttccagcgac agggcaccct gtcgatgacc tgcttgctga tactcaaaaa  300
catttacccg tcagcatgtt tgctatcgat ggcgaagtca ccggcggctt caagaagaca  360
tatgcttttt tcccaacaga taatatgcct ggcgtagcag agttgtcggc tatcccgagt  420
atgccgcccg cagtggccga gaacgctgag ctgttcgctc gttatggcct tgataaggtt  480
caaatgacaa gtatggatta caagaagcgt caggtaaacc tgtacttcag cgagctttca  540
gctcaaaccc tggaagccga gtccgtatta gcccttgtac gtgagttggg cttacacgta  600
ccaaacgagc ttggactgaa attctgtaaa cgctcgttta gtgtttaccc tacattaaat  660
tgggagactg gcaagattga tcgtttatgc ttcgcagtga tctccaacga tccgactctg  720
gtgccgagct ctgatgaagg agatattgaa aaatttcata attatgctac aaaggccccg  780
tatgcatatg ttggcgaaaa gcgcactctt gtctatggcc tgactttaag tcccaaggag  840
gagtactata aactgggagc atattaccat atcaccgacg ttcaacgcgg acttttgaaa  900
gcgtttgact cattggagga ttaa                                          924

SEQ ID NO: 2             moltype = AA  length = 307
FEATURE                  Location/Qualifiers
source                   1..307
                         mol_type = protein
                         organism = Streptomyces sp.
SEQUENCE: 2
MSEAADVERV YAAMEEAAGL LGVACARDKI YPLLSTFQDT LVEGGSVVVF SMASGRHSTE   60
LDFSISVPTS HGDPYATVVE KGLFPATGHP VDDLLADTQK HLPVSMFAID GEVTGGFKKT  120
YAFFPTDNMP GVAELSAIPS MPPAVAENAE LFARYGLDKV QMTSMDYKKR QVNLYFSELS  180
AQTLEAESVL ALVRELGLHV PNELGLKFCK RSFSVYPTLN WETGKIDRLC FAVISNDPTL  240
VPSSDEGDIE KFHNYATKAP YAYVGEKRTL VYGLTLSPKE EYYKLGAYYH ITDVQRGLLK  300
AFDSLED                                                             307

SEQ ID NO: 3             moltype = DNA  length = 924
FEATURE                  Location/Qualifiers
misc_feature             1..924
                         note = Synthetic polynucleotide
source                   1..924
                         mol_type = other DNA
                         organism = synthetic construct
SEQUENCE: 3
atgtccgagg ccgcagatgt agaacgcgtt tacgcagcta tggaggaagc cgcagggctg   60
ctggggtgg cgtgtgctcg cgacaaaatc tatcccttc tttcgacgtt tcaggacaca   120
```

```
ctggtagaag gaggctccgt tgttgtgttt agcatggctt ccggtcgtca cagtacagag    180
cttgatttct caatttccgt acccacgtcg catggggacc cctatgccac tgttgtggag    240
aagggggttgt ttccagcgac agggcaccct gtcgatgacc tgcttgctga tactcaaaaa    300
catttacccg tcagcatgtt tgctatcgat ggcgaagtca ccggcggctt caagaagaca    360
tatgcttttt tcccaacaga taatatgcct ggcgtagcag agttgtcggc tatcccgagt    420
atgccgcccg cagtggccga gaacgctgag ctgttcgctc gttatggcct tgataaggtt    480
caaatgacaa gtatggatta caagaagcgt caggtaaacc tgtacttcag cgagctttca    540
gctcaaaccc tggaagccga gtccgtatta gcccttgtac gtgagttggg cttacacgta    600
ccaaacgagc ttggactgaa attctgtaaa cgctcgttta gtgtttaccc tacattaaat    660
tgggagactg gcaagattga tcgtttatgc ttcagcgtga tctccaacga tccgactctg    720
gtgccgagct ctgatgaagg agatattgaa aaatttcata attatgctac aaaggccccg    780
tatgcatatg ttggcgaaaa gcgcactctt gtctatggcc tgactttaag tcccaaggag    840
gagtactata aactgggagc agtgtaccat atcaccgacg ttcaacgcgg acttttgaaa    900
gcgtttgact cattggagga ttaa                                            924

SEQ ID NO: 4              moltype = AA   length = 307
FEATURE                   Location/Qualifiers
REGION                    1..307
                          note = Synthetic polypeptide
source                    1..307
                          mol_type = protein
                          organism = synthetic construct
SEQUENCE: 4
MSEAADVERV YAAMEEAAGL LGVACARDKI YPLLSTFQDT LVEGGSVVVF SMASGRHSTE     60
LDFSISVPTS HGDPYATVVE KGLFPATGHP VDDLLADTQK HLPVSMFAID GEVTGGFKKT    120
YAFFPTDNMP GVAELSAIPS MPPAVAENAE LFARYGLDKV QMTSMDYKKR QVNLYFSELS    180
AQTLEAESVL ALVRELGLHV PNELGLKFCK RSFSVYPTLN WETGKIDRLC FSVISNDPTL    240
VPSSDEGDIE KFHNYATKAP YAYVGEKRTL VYGLTLSPKE EYYKLGAVYH ITDVQRGLLK    300
AFDSLED                                                              307

SEQ ID NO: 5              moltype = DNA   length = 924
FEATURE                   Location/Qualifiers
misc_feature              1..924
                          note = Synthetic polynucleotide
source                    1..924
                          mol_type = other DNA
                          organism = synthetic construct
SEQUENCE: 5
atgtccgagg ccgcagatgt agaacgcgtt tacgcagcta tggaggaagc cgcagggctg     60
ctggggggtgc cgtgtgctcg cgacaaaatc tatccccttc tttcgacgtt tcaggacaca    120
ctggtagaag gaggctccgt tgttgtgttt agcatggctt ccggtcgtca cagtacagag    180
cttgatttct caatttccgt acccacgtcg catggggacc cctatgccac tgttgtggag    240
aagggggttgt ttccagcgac agggcaccct gtcgatgacc tgcttgctga tactcaaaaa    300
catttacccg tcagcatgtt tgctatcgat ggcgaagtca ccggcggctt caagaagaca    360
tatgcttttt tcccaacaga taatatgcct ggcgtagcag agttgtcggc tatcccgagt    420
atgccgcccg cagtggccga gaacgctgag ctgttcgctc gttatggcct tgataaggtt    480
caaatgacaa gtatggatta caagaagcgt caggtaaacc tgtacttcag cgagctttca    540
gctcaaaccc tggaagccga gtccgtatta gcccttgtac gtgagttggg cttacacgta    600
ccaaacgagc ttggactgaa attctgtaaa cgctcgttta gtgtttaccc tacattaaat    660
tgggagactg gcaagattga tcgtttatgc ttcagcgtga tctccaacga tccgactctg    720
gtgccgagct ctgatgaagg agatattgaa aaatttcata attatgctac aaaggccccg    780
tatgcatatg ttggcgaaaa gcgcactctt gtctatggcc tgactttaag tcccaaggag    840
gagtactata aactgggagc agtgtaccat atcaccgacg ttcaacgcgg acttttgaaa    900
gcgtttgact cattggagga ttaa                                            924

SEQ ID NO: 6              moltype = AA   length = 307
FEATURE                   Location/Qualifiers
REGION                    1..307
                          note = Synthetic polypeptide
source                    1..307
                          mol_type = protein
                          organism = synthetic construct
SEQUENCE: 6
MSEAADVERV YAAMEEAAGL LGVPCARDKI YPLLSTFQDT LVEGGSVVVF SMASGRHSTE     60
LDFSISVPTS HGDPYATVVE KGLFPATGHP VDDLLADTQK HLPVSMFAID GEVTGGFKKT    120
YAFFPTDNMP GVAELSAIPS MPPAVAENAE LFARYGLDKV QMTSMDYKKR QVNLYFSELS    180
AQTLEAESVL ALVRELGLHV PNELGLKFCK RSFSVYPTLN WETGKIDRLC FSVISNDPTL    240
VPSSDEGDIE KFHNYATKAP YAYVGEKRTL VYGLTLSPKE EYYKLGAVYH ITDVQRGLLK    300
AFDSLED                                                              307

SEQ ID NO: 7              moltype = DNA   length = 924
FEATURE                   Location/Qualifiers
misc_feature              1..924
                          note = Synthetic polynucleotide
source                    1..924
                          mol_type = other DNA
                          organism = synthetic construct
SEQUENCE: 7
atgtccgagg ccgcagatgt agaacgcgtt tacgcagcta tggaggaagc cgcagggctg     60
```

```
ctggggtgg  cgtgtgctcg  cgacaaaatc  tatcccttc   tttcgacgtt  tcaggacaca   120
ctggtagaag  gaggctccgt  tgttgtgttt  agcatggctt  ccggtcgtca  cagtacagag   180
cttgatttct  caatttccgt  acccacgtcg  catgggacc   cctatgccac  tgttgtggag   240
aagggggttgt  ttccaccgac  agggcaccct  gtcgatgacc  tgcttgctga  tactcaaaaa   300
catttacccg  tcagcatgtt  tgctatcgat  ggcgaagtca  ccggcggctt  caagaagaca   360
tatgctttt   tcccaacaga  taatatgcct  ggcgtagcag  agttgtcggc  tatcccgagt   420
atgccgcccg  cagtggccga  gaacgctgag  ctgttcgctc  gttatggcct  tgataaggtt   480
caaatgacaa  gtatggatta  caagaagcgt  caggtaaacc  tgtacttcag  cgagctttca   540
gctcaaaccc  tggaagccga  gtccgtatta  gcccttgtac  gtgagttggg  cttacacgta   600
ccaaacgagc  ttggactgaa  attctgtaaa  cgctcgttta  gtgtttaccc  tacattaaat   660
tgggagactg  gcaagattga  tcgtttatgc  ttcagcgtga  tctccaacga  tccgactctg   720
gtgccgagct  ctgatgaagg  agatattgaa  aaatttcata  attatgctac  aaaggccccg   780
tatgcatatg  ttggcgaaaa  gcgcactctt  gtctatggcc  tgactttaag  tcccaaggag   840
gagtactata  aactgggagc  agtgtaccat  atcaccgacg  ttcaacgcgg  acttttgaaa   900
gcgtttgact  cattggagga  ttaa                                            924
```

```
SEQ ID NO: 8           moltype = AA   length = 307
FEATURE                Location/Qualifiers
REGION                 1..307
                       note = Synthetic polypeptide
source                 1..307
                       mol_type = protein
                       organism = synthetic construct
SEQUENCE: 8
MSEAADVERV YAAMEEAAGL LGVACARDKI YPLLSTFQDT LVEGGSVVVF SMASGRHSTE    60
LDFSISVPTS HGDPYATVVE KGLFPPTGHP VDDLLADTQK HLPVSMFAID GEVTGGFKKT   120
YAFFPTDNMP GVAELSAIPS MPPAVAENAE LFARYGLDKV QMTSMDYKKR QVNLYFSELS   180
AQTLEAESVL ALVRELGLHV PNELGLKFCK RSFSVYPTLN WETGKIDRLC FSVISNDPTL   240
VPSSDEGDIE KFHNYATKAP YAYVGEKRTL VYGLTLSPKE EYYKLGAVYH ITDVQRGLLK   300
AFDSLED                                                             307
```

```
SEQ ID NO: 9           moltype = DNA   length = 924
FEATURE                Location/Qualifiers
misc_feature           1..924
                       note = Synthetic polynucleotide
source                 1..924
                       mol_type = other DNA
                       organism = synthetic construct
SEQUENCE: 9
atgtccgagg  ccgcagatgt  agaacgcgtt  tacgcagcta  tggaggaagc  cgcagggctg    60
ctggggtgg   cgtgtgctcg  cgacaaaatc  tatcccttc   tttcgacgtt  tcaggacaca   120
ctggtagaag  gaggctccgt  tgttgtgttt  agcatggctt  ccggtcgtca  cagtacagag   180
cttgatttct  caatttccgt  acccacgtcg  catgggacc   cctatgccac  tgttgtggag   240
aagggggttgt  ttccagcgac  agggcaccct  attgatgacc  tgcttgctga  tactcaaaaa   300
catttacccg  tcagcatgtt  tgctatcgat  ggcgaagtca  ccggcggctt  caagaagaca   360
tatgctttt   tcccaacaga  taatatgcct  ggcgtagcag  agttgtcggc  tatcccgagt   420
atgccgcccg  cagtggccga  gaacgctgag  ctgttcgctc  gttatggcct  tgataaggtt   480
caaatgacaa  gtatggatta  caagaagcgt  caggtaaacc  tgtacttcag  cgagctttca   540
gctcaaaccc  tggaagccga  gtccgtatta  gcccttgtac  gtgagttggg  cttacacgta   600
ccaaacgagc  ttggactgaa  attctgtaaa  cgctcgttta  gtgtttaccc  tacattaaat   660
tgggagactg  gcaagattga  tcgtttatgc  ttcagcgtga  tctccaacga  tccgactctg   720
gtgccgagct  ctgatgaagg  agatattgaa  aaatttcata  attatgctac  aaaggccccg   780
tatgcatatg  ttggcgaaaa  gcgcactctt  gtctatggcc  tgactttaag  tcccaaggag   840
gagtactata  aactgggagc  agtgtaccat  atcaccgacg  ttcaacgcgg  acttttgaaa   900
gcgtttgact  cattggagga  ttaa                                            924
```

```
SEQ ID NO: 10          moltype = AA   length = 307
FEATURE                Location/Qualifiers
REGION                 1..307
                       note = Synthetic polypeptide
source                 1..307
                       mol_type = protein
                       organism = synthetic construct
SEQUENCE: 10
MSEAADVERV YAAMEEAAGL LGVACARDKI YPLLSTFQDT LVEGGSVVVF SMASGRHSTE    60
LDFSISVPTS HGDPYATVVE KGLFPATGHP IDDLLADTQK HLPVSMFAID GEVTGGFKKT   120
YAFFPTDNMP GVAELSAIPS MPPAVAENAE LFARYGLDKV QMTSMDYKKR QVNLYFSELS   180
AQTLEAESVL ALVRELGLHV PNELGLKFCK RSFSVYPTLN WETGKIDRLC FSVISNDPTL   240
VPSSDEGDIE KFHNYATKAP YAYVGEKRTL VYGLTLSPKE EYYKLGAVYH ITDVQRGLLK   300
AFDSLED                                                             307
```

```
SEQ ID NO: 11          moltype = DNA   length = 924
FEATURE                Location/Qualifiers
misc_feature           1..924
                       note = Synthetic polynucleotide
source                 1..924
                       mol_type = other DNA
                       organism = synthetic construct
SEQUENCE: 11
```

```
atgtccgagg ccgcagatgt agaacgcgtt tacgcagcta tggaggaagc cgcagggctg    60
ctgggggtgg cgtgtgctcg cgacaaaatc tatccccttc tttcgacgtt tcaggacaca   120
ctggtagaag gaggctccgt tgttgtgttt agcatggctt ccggtcgtca cagtacagag   180
cttgatttct caatttccgt acccacgtcg catgggacc  cctatgccac tgttgtggag   240
aaggggttgt ttccagcgac agggcaccct gtcgatgacc tgcttgctga tactcaaaaa   300
catttacccg tcagcatgtt tgctatcgat ggcgaagtca ccggcggctt caagaagatt   360
tatgcttttt tcccaacaga taatatgcct ggcgtagcag agttgtcggc tatcccgagt   420
atgccgcccg cagtggccga gaacgctgag ctgttcgctc gttatggcct tgataaggtt   480
caaatgacaa gtatggatta caagaagcgt caggtaaacc tgtacttcag cgagctttca   540
gctcaaaccc tggaagccga gtccgtatta gcccttgtac gtgagttggg cttacacgta   600
ccaaacgagc ttggactgaa attcgtaaa  cgctcgttta gtgtttaccc tacattaaat   660
tgggagactg gcaagattga tcgtttatgc ttcagcgtga tctccaacga tccgactctg   720
gtgccgagct ctgatgaagg agatattgaa aaatttcata ttatgctac  aaaggccccg   780
tatgcatatg ttggcgaaaa cgcactctt  gtctatggcc tgactttaag tcccaaggag   840
gagtactata aactgggagc agtgtaccat atcaccgacg ttcaacgcgg acttttgaaa   900
gcgtttgact cattggagga ttaa                                          924

SEQ ID NO: 12            moltype = AA  length = 307
FEATURE                  Location/Qualifiers
REGION                   1..307
                         note = Synthetic polypeptide
source                   1..307
                         mol_type = protein
                         organism = synthetic construct
SEQUENCE: 12
MSEAADVERV YAAMEEAAGL LGVACARDKI YPLLSTFQDT LVEGGSVVVF SMASGRHSTE    60
LDFSISVPTS HGDPYATVVE KGLFPATGHP VDDLLADTQK HLPVSMFAID GEVTGGFKKI   120
YAFFPTDNMP GVAELSAIPS MPPAVAENAE LFARYGLDKV QMTSMDYKKR QVNLYFSELS   180
AQTLEAESVL ALVRELGLHV PNELGLKFCK RSFSVYPTLN WETGKIDRLC FSVISNDPTL   240
VPSSDEGDIE KFHNYATKAP YAYVGEKRTL VYGLTLSPKE EYYKLGAVYH ITDVQRGLLK   300
AFDSLED                                                             307

SEQ ID NO: 13            moltype = DNA  length = 924
FEATURE                  Location/Qualifiers
misc_feature             1..924
                         note = Synthetic polynucleotide
source                   1..924
                         mol_type = other DNA
                         organism = synthetic construct
SEQUENCE: 13
atgtccgagg ccgcagatgt agaacgcgtt tacgcagcta tggaggaagc cgcagggctg    60
ctgggggtgg cgtgtgctcg cgacaaaatc tatccccttc tttcgacgtt tcaggacaca   120
ctggtagaag gaggctccgt tgttgtgttt agcatggctt ccggtcgtca cagtacagag   180
cttgatttct caatttccgt acccacgtcg catgggacc  cctatgccac tgttgtggag   240
aaggggttgt ttccagcgac agggcaccct gtcgatgacc tgcttgctga tactcaaaaa   300
catttacccg tcagcatgtt tgctatcgat ggcgaagtca ccggcggctt caagaagaca   360
tatgcttttt tcccaccgga taatatgcct ggcgtagcag agttgtcggc tatcccgagt   420
atgccgcccg cagtggccga gaacgctgag ctgttcgctc gttatggcct tgataaggtt   480
caaatgacaa gtatggatta caagaagcgt caggtaaacc tgtacttcag cgagctttca   540
gctcaaaccc tggaagccga gtccgtatta gcccttgtac gtgagttggg cttacacgta   600
ccaaacgagc ttggactgaa attcgtaaa  cgctcgttta gtgtttaccc tacattaaat   660
tgggagactg gcaagattga tcgtttatgc ttcagcgtga tctccaacga tccgactctg   720
gtgccgagct ctgatgaagg agatattgaa aaatttcata ttatgctac  aaaggccccg   780
tatgcatatg ttggcgaaaa cgcactctt  gtctatggcc tgactttaag tcccaaggag   840
gagtactata aactgggagc agtgtaccat atcaccgacg ttcaacgcgg acttttgaaa   900
gcgtttgact cattggagga ttaa                                          924

SEQ ID NO: 14            moltype = AA  length = 307
FEATURE                  Location/Qualifiers
REGION                   1..307
                         note = Synthetic polypeptide
source                   1..307
                         mol_type = protein
                         organism = synthetic construct
SEQUENCE: 14
MSEAADVERV YAAMEEAAGL LGVACARDKI YPLLSTFQDT LVEGGSVVVF SMASGRHSTE    60
LDFSISVPTS HGDPYATVVE KGLFPATGHP VDDLLADTQK HLPVSMFAID GEVTGGFKKT   120
YAFFPPDNMP GVAELSAIPS MPPAVAENAE LFARYGLDKV QMTSMDYKKR QVNLYFSELS   180
AQTLEAESVL ALVRELGLHV PNELGLKFCK RSFSVYPTLN WETGKIDRLC FSVISNDPTL   240
VPSSDEGDIE KFHNYATKAP YAYVGEKRTL VYGLTLSPKE EYYKLGAVYH ITDVQRGLLK   300
AFDSLED                                                             307

SEQ ID NO: 15            moltype = DNA  length = 924
FEATURE                  Location/Qualifiers
misc_feature             1..924
                         note = Synthetic polynucleotide
source                   1..924
                         mol_type = other DNA
                         organism = synthetic construct
```

```
SEQUENCE: 15
atgtccgagg ccgcagatgt agaacgcgtt tacgcagcta tggaggaagc cgcagggctg    60
ctgggggtgg cgtgtgctcg cgacaaaatc tatccccttc tttcgacgtt tcaggacaca   120
ctggtagaag gaggctccgt tgttgtgttt agcatggctt ccggtcgtca cagtacagag   180
cttgatttct caatttccgt acccacgtcg catggggacc cctatgccac tgttgtggag   240
aagggggttgt ttccagcgac agggcaccct gtcgatgacc tgcttgctga tactcaaaaa   300
catttacccg tcagcatgtt tgctatcgat ggcgaagtca ccggcggctt caagaagaca   360
tatgcttttt tcccaacaga taatatgcct ggcgtagcag agttgtcggc tatcccgagt   420
atgccgcccg cagtggccga gaacgctgag ctgttcgctc gttatggcct tgataaggtt   480
caaatgatta gtatggatta caagaagcgt caggtaaacc tgtacttcag cgagctttca   540
gctcaaaccc tggaagccga gtccgtatta gcccttgtac gtgagttggg cttacacgta   600
ccaaacgagc ttggactgaa attctgtaaa cgctcgttta gtgtttaccc tacattaaat   660
tgggagactg caagattga tcgtttatgc ttcagcgtga tctccaacga tccgactctg   720
gtgccgagct ctgatgaagg agatattgaa aaatttcata attatgctac aaaggccccg   780
tatgcatatg ttggcgaaaa gcgcactctt gtctatggcc tgactttaag tcccaaggag   840
gagtactata aactgggagc agtgtaccat atcaccgacg ttcaacgcgg acttttgaaa   900
gcgtttgact cattggagga ttaa                                            924

SEQ ID NO: 16          moltype = AA   length = 307
FEATURE                Location/Qualifiers
REGION                 1..307
                       note = Synthetic polypeptide
source                 1..307
                       mol_type = protein
                       organism = synthetic construct
SEQUENCE: 16
MSEAADVERV YAAMEEAAGL LGVACARDKI YPLLSTFQDT LVEGGSVVVF SMASGRHSTE    60
LDFSISVPTS HGDPYATVVE KGLFPATGHP VDDLLADTQK HLPVSMFAID GEVTGGFKKT   120
YAFFPTDNMP GVAELSAIPS MPPAVAENAE LFARYGLDKV QMISMDYKKR QVNLYFSELS   180
AQTLEAESVL ALVRELGLHV PNELGLKFCK RSFSVYPTLN WETGKIDRLC FSVISNDPTL   240
VPSSDEGDIE KFHNYATKAP YAYVGEKRTL VYGLTLSPKE EYYKLGAVYH ITDVQRGLLK   300
AFDSLED                                                              307

SEQ ID NO: 17          moltype = DNA  length = 924
FEATURE                Location/Qualifiers
misc_feature           1..924
                       note = Synthetic polynucleotide
source                 1..924
                       mol_type = other DNA
                       organism = synthetic construct
SEQUENCE: 17
atgtccgagg ccgcagatgt agaacgcgtt tacgcagcta tggaggaagc cgcagggctg    60
ctgggggtgg cgtgtgctcg cgacaaaatc tatccccttc tttcgacgtt tcaggacaca   120
ctggtagaag gaggctccgt tgttgtgttt agcatggctt ccggtcgtca cagtacagag   180
cttgatttct caatttccgt acccacgtcg catggggacc cctatgccac tgttgtggag   240
aagggggttgt ttccagcgac agggcaccct gtcgatgacc tgcttgctga tactcaaaaa   300
catttacccg tcagcatgtt tgctatcgat ggcgaagtca ccggcggctt caagaagaca   360
tatgcttttt tcccaacaga taatatgcct ggcgtagcag agttgtcggc tatcccgagt   420
atgccgcccg cagtggccga gaacgctgag ctgttcgctc gttatggcct tgataaggtt   480
caaatgacaa gtatggattt aagaagcgt caggtaaacc tgtacttcag cgagctttca   540
gctcaaaccc tggaagccga gtccgtatta gcccttgtac gtgagttggg cttacacgta   600
ccaaacgagc ttggactgaa attctgtaaa cgctcgttta gtgtttaccc tacattaaat   660
tgggagactg caagattga tcgtttatgc ttcagcgtga tctccaacga tccgactctg   720
gtgccgagct ctgatgaagg agatattgaa aaatttcata attatgctac aaaggccccg   780
tatgcatatg ttggcgaaaa gcgcactctt gtctatggcc tgactttaag tcccaaggag   840
gagtactata aactgggagc agtgtaccat atcaccgacg ttcaacgcgg acttttgaaa   900
gcgtttgact cattggagga ttaa                                            924

SEQ ID NO: 18          moltype = AA   length = 307
FEATURE                Location/Qualifiers
REGION                 1..307
                       note = Synthetic polypeptide
source                 1..307
                       mol_type = protein
                       organism = synthetic construct
SEQUENCE: 18
MSEAADVERV YAAMEEAAGL LGVACARDKI YPLLSTFQDT LVEGGSVVVF SMASGRHSTE    60
LDFSISVPTS HGDPYATVVE KGLFPATGHP VDDLLADTQK HLPVSMFAID GEVTGGFKKT   120
YAFFPTDNMP GVAELSAIPS MPPAVAENAE LFARYGLDKV QMTSMDFKKR QVNLYFSELS   180
AQTLEAESVL ALVRELGLHV PNELGLKFCK RSFSVYPTLN WETGKIDRLC FSVISNDPTL   240
VPSSDEGDIE KFHNYATKAP YAYVGEKRTL VYGLTLSPKE EYYKLGAVYH ITDVQRGLLK   300
AFDSLED                                                              307

SEQ ID NO: 19          moltype = DNA  length = 924
FEATURE                Location/Qualifiers
misc_feature           1..924
                       note = Synthetic polynucleotide
source                 1..924
                       mol_type = other DNA
```

```
                          organism = synthetic construct
SEQUENCE: 19
atgtccgagg ccgcagatgt agaacgcgtt tacgcagcta tggaggaagc cgcagggctg    60
ctgggggtgg cgtgtgctcg cgacaaaatc tatcccttc tttcgacgtt tcaggacaca    120
ctggtagaag gaggctccgt tgttgtgttt agcatggctt ccggtcgtca cagtacagag   180
cttgatttct caatttccgt acccacgtcg catgggacc cctatgccac tgttgtggag    240
aaggggttgt ttccagcgac agggcaccct gtcgatgacc tgcttgctga tactcaaaaa   300
catttacccg tcagcatgtt tgctatcgat ggcgaagtca ccggcggctt caagaagaca   360
tatgcttttt tcccaacaga taatatgcct ggcgtagcag agttgtcggc tatcccgagt   420
atgccgcccg cagtggccga gaacgctgag ctgttcgctc gttatggcct tgataaggtt   480
caaatgacaa gtatggatta caagaagcgt caggtaaacc tgtacttcag cgagctttca   540
ccgcaaaccc tggaagccga gtccgtatta gcccttgtac gtgagttggg cttacacgta   600
ccaaacgagc ttggactgaa attctgtaaa cgctcgttta gtgtttaccc tacattaaat   660
tgggagactg gcaagattga tcgtttatgc ttcagcgtga tctccaacga tccgactctg   720
gtgccgagct ctgatgaagg agatattgaa aaatttcata attatgctac aaaggccccg   780
tatgcatatg ttggcgaaaa gcgcactctt gtctatggcc tgactttaag tcccaaggag   840
gagtactata aactgggagc agtgtaccat atcaccgacg ttcaacgcgg acttttgaaa   900
gcgtttgact cattggagga ttaa                                            924

SEQ ID NO: 20              moltype = AA   length = 307
FEATURE                    Location/Qualifiers
REGION                     1..307
                           note = Synthetic polypeptide
source                     1..307
                           mol_type = protein
                           organism = synthetic construct
SEQUENCE: 20
MSEAADVERV YAAMEEAAGL LGVACARDKI YPLLSTFQDT LVEGGSVVVF SMASGRHSTE    60
LDFSISVPTS HGDPYATVVE KGLFPATGHP VDDLLADTQK HLPVSMFAID GEVTGGFKKT   120
YAFFPTDNMP GVAELSAIPS MPPAVAENAE LFARYGLDKV QMTSMDYKKR QVNLYFSELS   180
PQTLEAESVL ALVRELGLHV PNELGLKFCK RSFSVYPTLN WETGKIDRLC FSVISNDPTL   240
VPSSDEGDIE KFHNYATKAP YAYVGEKRTL VYGLTLSPKE EYYKLGAVYH ITDVQRGLLK   300
AFDSLED                                                             307

SEQ ID NO: 21              moltype = DNA   length = 924
FEATURE                    Location/Qualifiers
misc_feature               1..924
                           note = Synthetic polynucleotide
source                     1..924
                           mol_type = other DNA
                           organism = synthetic construct
SEQUENCE: 21
atgtccgagg ccgcagatgt agaacgcgtt tacgcagcta tggaggaagc cgcagggctg    60
ctgggggtgg cgtgtgctcg cgacaaaatc tatcccttc tttcgacgtt tcaggacaca   120
ctggtagaag gaggctccgt tgttgtgttt agcatggctt ccggtcgtca cagtacagag   180
cttgatttct caatttccgt acccacgtcg catgggacc cctatgccac tgttgtggag    240
aaggggttgt ttccagcgac agggcaccct gtcgatgacc tgcttgctga tactcaaaaa   300
catttacccg tcagcatgtt tgctatcgat ggcgaagtca ccggcggctt caagaagaca   360
tatgcttttt tcccaacaga taatatgcct ggcgtagcag agttgtcggc tatcccgagt   420
atgccgcccg cagtggccga gaacgctgag ctgttcgctc gttatggcct tgataaggtt   480
caaatgacaa gtatggatta caagaagcgt caggtaaacc tgtacttcag cgagctttca   540
gctcaaaccc tggaagccga gtccgtatta gcccttgtac gtgagttggg cttacacgta   600
ccaaacgagc ttggactgaa attctgtaaa cgctcgttta gtgtttaccc tacattaaat   660
tgggagactg gcaagattga tcgtttatgc ttcagcgtga tctccaacga tccgactctg   720
gtgccgagct ctgatgaagg agatattgaa aaatttcata attatgctac aaaggccccg   780
tatgcatatg ttggcgaaaa gcgcgtgctt gtctatggcc tgactttaag tcccaaggag   840
gagtactata aactgggagc agtgtaccat atcaccgacg ttcaacgcgg acttttgaaa   900
gcgtttgact cattggagga ttaa                                            924

SEQ ID NO: 22              moltype = AA   length = 307
FEATURE                    Location/Qualifiers
REGION                     1..307
                           note = Synthetic polypeptide
source                     1..307
                           mol_type = protein
                           organism = synthetic construct
SEQUENCE: 22
MSEAADVERV YAAMEEAAGL LGVACARDKI YPLLSTFQDT LVEGGSVVVF SMASGRHSTE    60
LDFSISVPTS HGDPYATVVE KGLFPATGHP VDDLLADTQK HLPVSMFAID GEVTGGFKKT   120
YAFFPTDNMP GVAELSAIPS MPPAVAENAE LFARYGLDKV QMTSMDYKKR QVNLYFSELS   180
AQTLEAESVL ALVRELGLHV PNELGLKFCK RSFSVYPTLN WETGKIDRLC FSVISNDPTL   240
VPSSDEGDIE KFHNYATKAP YAYVGEKRVL VYGLTLSPKE EYYKLGAVYH ITDVQRGLLK   300
AFDSLED                                                             307

SEQ ID NO: 23              moltype = DNA   length = 924
FEATURE                    Location/Qualifiers
misc_feature               1..924
                           note = Synthetic polynucleotide
source                     1..924
```

```
                        mol_type = other DNA
                        organism = synthetic construct
SEQUENCE: 23
atgtccgagg ccgcagatgt agaacgcgtt tacgcagcta tggaggaagc cgcagggctg    60
ctgggggtgg cgtgtgctcg cgacaaaatc tatccccttc tttcgacgtt tcaggacaca   120
ctggtagaag gaggctccgt tgttgtgttt agcatggcct ccggtcgtca cagtacagag   180
cttgatttct caatttccgt acccacgtcg catgggacc cctatgccac tgttgtggag    240
aagggggttg ttccagcgac agggcaccct attgatgacc tgcttgctga tactcaaaaa   300
catttacccg tcagcatgtt tgctatcgat ggcgaagtca cgggcggctt caagaagaca   360
tatgcttttt tcccaacaga taatatgcct ggcgtagcag agttgtcggc tatcccgagt   420
atgccgcccg cagtggccga gaacgctgag ctgttcgctc gttatggcct tgataaggtt   480
caaatgatta gtatggatta caagaagcgt caggtaaacc tgtacttcag cgagctttca   540
gctcaaaccc tggaagccga gtccgtatta gcccttgtac gtgagtttgg cttacacgta   600
ccaaacgagc ttggactgaa attctgtaaa cgctcgttta cgtgttaccc tacattaaat   660
tgggagactg gcaagattga tcgtttatgc ttcagcgtga tctccaacga tccgactctg   720
gtgccgagct ctgatgaagg agatattgaa aaatttcata attatgctac aaaggccccg   780
tatgcatatg ttggcgaaaa agcgcactct tgtctatggc ctgactttaag tcccaaggag   840
gagtactata aactgggagc agtgtaccat atcaccgacg ttcaacgcgg acttttgaaa   900
gcgtttgact cattggagga ttaa                                           924

SEQ ID NO: 24           moltype = AA   length = 307
FEATURE                 Location/Qualifiers
REGION                  1..307
                        note = Synthetic polypeptide
source                  1..307
                        mol_type = protein
                        organism = synthetic construct
SEQUENCE: 24
MSEAADVERV YAAMEEAAGL LGVACARDKI YPLLSTFQDT LVEGGSVVVF SMASGRHSTE    60
LDFSISVPTS HGDPYATVVE KGLFPATGHP IDDLLADTQK HLPVSMFAID GEVTGGFKKT   120
YAFFPTDNMP GVAELSAIPS MPPAVAENAE LFARYGLDKV QMISMDYKKR QVNLYFSELS   180
AQTLEAESVL ALVRELGLHV PNELGLKFCK RSFSVYPTLN WETGKIDRLC FSVISNDPTL   240
VPSSDEGDIE KFHNYATKAP YAYVGEKRTL VYGLTLSPKE EYYKLGAVYH ITDVQRGLLK   300
AFDSLED                                                             307

SEQ ID NO: 25           moltype = DNA   length = 924
FEATURE                 Location/Qualifiers
misc_feature            1..924
                        note = Synthetic polynucleotide
source                  1..924
                        mol_type = other DNA
                        organism = synthetic construct
SEQUENCE: 25
atgtcggaag ctgccgatgt agaacgtgtc tacgccgcca tcgaagaagc cgcaggtttg    60
ttgggggtcg catgcgcacg cgataagatt tggcccttgc tgtcaacatt ccaggatacc   120
ttggttgagg gtggaagcgt agttgttttt agcatggcct cggggcgtca ctcaacggag   180
ctggacttct caatttccgt cccgccuagt catggcgatc gtacgcgat tgtggtggaa    240
aagggcttgt tcccggcaac tggacatcca gttgatgacc ttctggcgga cattcagaag   300
catcttcccg tatctatgtt tgcgattgac ggggaagtta ccgggggggtt caaaaaaact   360
tatgcgttct tcccgaccga taacatgccc ggtgtcgcgg aactggcggc catcccatcg   420
atgcctcctg cagtcgctga aaatgctgaa ctgttcgcgc gttatggcct ggacaaggta   480
caaatgacct cgatggatta taaaaaacgt caagtgaacc tgtatttctc gaactgtcg    540
gctcagacgc tggaggctga atcagtactt gctttagtgc gtgaactggg tcttcatgtc   600
ccaaacgagc tgggtctgaa attttgcaaa cgctccttct cagtataccc aacattaaac   660
tgggcacct cgaagattga ccgcctttgc ttctctgtaa tcagtacgaa tccgacactt   720
gtacctagct cagacgaggg agacattgaa aaatttcaca attacgctac aaaggccccc   780
tatgcatatg ttggagaaaa agcgtacactt gtttacggct tgactttatc tcccaaagag   840
gagtattata aattgggtgc cgtttaccac attactgacg tacaacgcaa acttttgaag   900
gcgttcgaca gccttgagga ttaa                                           924

SEQ ID NO: 26           moltype = AA   length = 307
FEATURE                 Location/Qualifiers
REGION                  1..307
                        note = Synthetic polypeptide
source                  1..307
                        mol_type = protein
                        organism = synthetic construct
SEQUENCE: 26
MSEAADVERV YAAIEEAAGL LGVACARDKI WPLLSTFQDT LVEGGSVVVF SMASGRHSTE    60
LDFSISVPPS HGDPYAIVVE KGLFPATGHP VDDLLADIQK HLPVSMFAID GEVTGGFKKT   120
YAFFPTDNMP GVAELAAIPS MPPAVAENAE LFARYGLDKV QMTSMDYKKR QVNLYFSELS   180
AQTLEAESVL ALVRELGLHV PNELGLKFCK RSFSVYPTLN WDTSKIDRLC FSVISTDPTL   240
VPSSDEGDIE KFHNYATKAP YAYVGEKRTL VYGLTLSPKE EYYKLGAVYH ITDVQRKLLK   300
AFDSLED                                                             307

SEQ ID NO: 27           moltype = DNA   length = 924
FEATURE                 Location/Qualifiers
misc_feature            1..924
                        note = Synthetic polynucleotide
```

```
source                       1..924
                             mol_type = other DNA
                             organism = synthetic construct
SEQUENCE: 27
atgtcggaag ctgccgatgt agaacgtgtc tacgccgcca tcgaagaagc cgcaggtttg   60
ttgggggtcc cgtgcgcacg cgataagatt tggcccttgc tgtcaacatt ccaggatacc  120
ttggttgagg gtgaagcgt agttgttttt agcatggcct cggggcgtca ctcaacggag  180
ctggacttct caatttccgt cccgcctagt catggcgatc cgtacgcgat gtggtggaa   240
aagggcttgt tcccggcaac tggacatcca gttgatgacc ttctggcgga cattcagaag  300
catcttcccg tatctatgtt tgcgattgac ggggaagtta ccgggggtt caaaaaaact   360
tatgcgttct tcccgaccga taacatgccc ggtgtcgcgg aactggcggc catcccatcg  420
atgcctcctg cagtcgctga aaatgctgaa ctgttcgcgc gttatggcct ggacaaggta  480
caaatgacct cgatggatta taaaaaacgt caagtgaacc tgtatttctc cgaactgtcg  540
gctcagacgc tggaggctga atcagtactt gctttagtgc gtgaactggg tcttcatgtc  600
ccaaacgagc tgggtctgaa attttgcaaa cgctccttct cagtataccc aacattaaac  660
tgggacacct cgaagattga ccgcctttgc ttctctgtaa tcagtacaga tccgacactt  720
gtacctagct cagacgaggg agacattgaa aaatttcaca attcgctac aaaggccccc   780
tatgcatatg ttggagaaaa gcgtacactt gtttacggct tgactttatc tcccaaagag  840
gagtattata aattgggtgc cgtttaccac attactgacg tacaacgcaa acttttgaag  900
gcgttcgaca gccttgagga ttaa                                          924

SEQ ID NO: 28                moltype = AA  length = 307
FEATURE                      Location/Qualifiers
REGION                       1..307
                             note = Synthetic polypeptide
source                       1..307
                             mol_type = protein
                             organism = synthetic construct
SEQUENCE: 28
MSEAADVERV YAAIEEAAGL LGVPCARDKI WPLLSTFQDT LVEGGSVVVF SMASGRHSTE   60
LDFSISVPPS HGDPYAIVVE KGLFPATGHP VDDLLADIQK HLPVSMFAID GEVTGGFKKT  120
YAFFPTDNMP GVAELAAIPS MPPAVAENAE LFARYGLDKV QMTSMDYKKR QVNLYFSELS  180
AQTLEAESVL ALVRELGLHV PNELGLKFCK RSFSVYPTLN WDTSKIDRLC FSVISTDPTL  240
VPSSDEGDIE KFHNYATKAP YAYVGEKRTL VYGLTLSPKE EYYKLGAVYH ITDVQRKLLK  300
AFDSLED                                                             307

SEQ ID NO: 29                moltype = DNA  length = 924
FEATURE                      Location/Qualifiers
misc_feature                 1..924
                             note = Synthetic polynucleotide
source                       1..924
                             mol_type = other DNA
                             organism = synthetic construct
SEQUENCE: 29
atgtcggaag ctgccgatgt agaacgtgtc tacgccgcca tcgaagaagc cgcaggtttg   60
ttgggggtcc cgtgcgcacg cgataagatt tggcccttgc tgtcaacatt ccaggatacc  120
ttggttgagg gtgaagcgt agttgttttt agcatggcct cggggcgtca ctcaacggag  180
ctggacttct caatttccgt cccgcctagt catggcgatc cgtacgcgat gtggtggaa   240
aagggcttgt tcccggcaac tggacatcca gttgatgacc ttctggcgga cattcagaag  300
catcttcccg tatctatgtt tgcgattgac ggggaagtta ccgggggtt caaaaaaact   360
tatgcgttct tcccgaccgga taacatgccc ggtgtcgcgg aactgccgcc catcccatcg  420
atgcctcctg cagtcgctga aaatgctgaa ctgttcgcgc gttatggcct ggacaaggta  480
caaatgacct cgatggatta taaaaaacgt caagtgaacc tgtatttctc cgaactgtcg  540
gctcagacgc tggaggctga atcagtactt gctttagtgc gtgaactggg tcttcatgtc  600
ccaaacgagc tgggtctgaa attttgcaaa cgctccttct cagtataccc aacattaaac  660
tgggacacct cgaagattga ccgcctttgc ttctctgtaa tcagtacaga tccgacactt  720
gtacctagct cagacgaggg agacattgaa aaatttcaca attcgctac aaaggccccc   780
tatgcatatg ttggagaaaa gcgtacactt gtttacggct tgactttatc tcccaaagag  840
gagtattata aattgggtgc cgtttaccac attactgacg tacaacgcaa acttttgaag  900
gcgttcgaca gccttgagga ttaa                                          924

SEQ ID NO: 30                moltype = AA  length = 307
FEATURE                      Location/Qualifiers
REGION                       1..307
                             note = Synthetic polypeptide
source                       1..307
                             mol_type = protein
                             organism = synthetic construct
SEQUENCE: 30
MSEAADVERV YAAIEEAAGL LGVPCARDKI WPLLSTFQDT LVEGGSVVVF SMASGRHSTE   60
LDFSISVPPS HGDPYAIVVE KGLFPATGHP VDDLLADIQK HLPVSMFAID GEVTGGFKKT  120
YAFFPPDNMP GVAELAAIPS MPPAVAENAE LFARYGLDKV QMTSMDYKKR QVNLYFSELS  180
AQTLEAESVL ALVRELGLHV PNELGLKFCK RSFSVYPTLN WDTSKIDRLC FSVISTDPTL  240
VPSSDEGDIE KFHNYATKAP YAYVGEKRTL VYGLTLSPKE EYYKLGAVYH ITDVQRKLLK  300
AFDSLED                                                             307

SEQ ID NO: 31                moltype = DNA  length = 924
FEATURE                      Location/Qualifiers
misc_feature                 1..924
```

|  |  |  |  |
|---|---|---|---|
| source | 1..924 | | |
|  | note = Synthetic polynucleotide | | |
|  | mol_type = other DNA | | |
|  | organism = synthetic construct | | |

SEQUENCE: 31

```
atgtcggaag ctgccgatgt agaacgtgtc tacgccgcca tcgaagaagc cgcaggtttg   60
ttgggggtcg catgcgcacg cgataagatt tggcccttgc tgtcaacatt ccaggatacc  120
ttggttgagg gtgtgaagcgt agttgttttt agcatggcct cggggcgtca ctcaacggag  180
ctggacttct caatttccgt cccgcctagt catggcgatc cgtacgcgat tgtggtggaa  240
aagggcttgt tcccgccgac tggacatcca gttgatgacc ttctggcgca cattcagaag  300
catcttcccg tatctatgtt tgcgattgac ggggaagtta ccgggggggtt caaaaaaact  360
tatgcgttct tcccgaccga taacatgccc ggtgtcgcgg aactgccggc catcccatcg  420
atgcctcctg cagtcgctga aaatgctgaa ctgttcgcgc gttatggcct ggacaaggta  480
caaatgacct cgatggatta taaaaaacgt caagtgaacc tgtatttctc cgaactgtcg  540
gctcagacgc tggaggctga atcagtactt gctttagtgc gtgaactggg tcttcatgtc  600
ccaaacgagc tgggtctgaa attttgcaaa cgctccttct cagtataccc aacattaaac  660
tgggacacct cgaagattga ccgcctttgc ttctctgtaa tcagtacaga tccgacactt  720
gtacctagtc cagacgaggg agacattgaa aaatttcaca attcgctac aaaggccccc  780
tatgcatatg ttggagaaaa gcgtacactt gtttacggct tgactttatc tcccaaagag  840
gagtattata aattgggtgc cgtttaccac attactgacg tacaacgcaa acttttgaag  900
gcgttcgaca gccttgagga ttaa                                         924
```

| SEQ ID NO: 32 | moltype = AA length = 307 |
|---|---|
| FEATURE | Location/Qualifiers |
| REGION | 1..307 |
|  | note = Synthetic polypeptide |
| source | 1..307 |
|  | mol_type = protein |
|  | organism = synthetic construct |

SEQUENCE: 32

```
MSEAADVERV YAAIEEAAGL LGVACARDKI WPLLSTFQDT LVEGGSVVVF SMASGRHSTE   60
LDFSISVPPS HGDPYAIVVE KGLFPPTGHP VDDLLADIQK HLPVSMFAID GEVTGGFKKT  120
YAFFPTDNMP GVAELAAIPS MPPAVAENAE LFARYGLDKV QMTSMDYKKR QVNLYFSELS  180
AQTLEAESVL ALVRELGLHV PNELGLKFCK RSFSVYPTLN WDTSKIDRLC FSVISTDPTL  240
VPSSDEGDIE KFHNYATKAP YAYVGEKRTL VYGLTLSPKE EYYKLGAVYH ITDVQRKLLK  300
AFDSLED                                                            307
```

| SEQ ID NO: 33 | moltype = DNA length = 924 |
|---|---|
| FEATURE | Location/Qualifiers |
| misc_feature | 1..924 |
|  | note = Synthetic polynucleotide |
| source | 1..924 |
|  | mol_type = other DNA |
|  | organism = synthetic construct |

SEQUENCE: 33

```
atgtcggaag ctgccgatgt agaacgtgtc tacgccgcca tcgaagaagc cgcaggtttg   60
ttgggggtcg catgcgcacg cgataagatt tggcccttgc tgtcaacatt ccaggatacc  120
ttggttgagg gtgtgaagcgt agttgttttt agcatggcct cggggcgtca ctcaacggag  180
ctggacttct caatttccgt cccgcctagt catggcgatc cgtacgcgat tgtggtggaa  240
aagggcttgt tcccggcaac tggacatcca attgatgacc ttctggcgga cattcagaag  300
catcttcccg tatctatgtt tgcgattgac ggggaagtta ccgggggggtt caaaaaaact  360
tatgcgttct tcccgaccga taacatgccc ggtgtcgcgg aactgccggc catcccatcg  420
atgcctcctg cagtcgctga aaatgctgaa ctgttcgcgc gttatggcct ggacaaggta  480
caaatgacct cgatggatta taaaaaacgt caagtgaacc tgtatttctc cgaactgtcg  540
gctcagacgc tggaggctga atcagtactt gctttagtgc gtgaactggg tcttcatgtc  600
ccaaacgagc tgggtctgaa attttgcaaa cgctccttct cagtataccc aacattaaac  660
tgggacacct cgaagattga ccgcctttgc ttctctgtaa tcagtacaga tccgacactt  720
gtacctagtc cagacgaggg agacattgaa aaatttcaca attcgctac aaaggccccc  780
tatgcatatg ttggagaaaa gcgtacactt gtttacggct tgactttatc tcccaaagag  840
gagtattata aattgggtgc cgtttaccac attactgacg tacaacgcaa acttttgaag  900
gcgttcgaca gccttgagga ttaa                                         924
```

| SEQ ID NO: 34 | moltype = AA length = 307 |
|---|---|
| FEATURE | Location/Qualifiers |
| REGION | 1..307 |
|  | note = Synthetic polypeptide |
| source | 1..307 |
|  | mol_type = protein |
|  | organism = synthetic construct |

SEQUENCE: 34

```
MSEAADVERV YAAIEEAAGL LGVACARDKI WPLLSTFQDT LVEGGSVVVF SMASGRHSTE   60
LDFSISVPPS HGDPYAIVVE KGLFPATGHP IDDLLADIQK HLPVSMFAID GEVTGGFKKT  120
YAFFPTDNMP GVAELAAIPS MPPAVAENAE LFARYGLDKV QMTSMDYKKR QVNLYFSELS  180
AQTLEAESVL ALVRELGLHV PNELGLKFCK RSFSVYPTLN WDTSKIDRLC FSVISTDPTL  240
VPSSDEGDIE KFHNYATKAP YAYVGEKRTL VYGLTLSPKE EYYKLGAVYH ITDVQRKLLK  300
AFDSLED                                                            307
```

| SEQ ID NO: 35 | moltype = DNA length = 924 |
|---|---|
| FEATURE | Location/Qualifiers |

```
misc_feature            1..924
                        note = Synthetic polynucleotide
source                  1..924
                        mol_type = other DNA
                        organism = synthetic construct
SEQUENCE: 35
atgtcggaag ctgccgatgt agaacgtgtc tacgccgcca tcgaagaagc cgcaggtttg    60
ttgggggtcg catgcgcacg cgataagatt tggcccttgc tgtcaacatt ccaggatacc   120
ttggttgagg gtggaagcgt agttgttttt agcatggcct cggggcgtca ctcaacggag   180
ctggacttct caatttccgt cccgcctagt catggcgatc cgtacgcgat tgtggtggaa   240
aagggcttgt tcccggcaac tggacatcca gttgatgacc ttctggcgga cattcagaag   300
catcttcccg tatctatgtt tgcgattgac ggggaagtta ccgggggggtt caaaaaaatt   360
tatgcgttct cccgaccga taacatgccc ggtgtcgcgg aactggcggc catcccatcg   420
atgcctcctg cagtcgctga aaatgctgaa ctgttcgcgc gttatggcct ggacaaggta   480
caaatgacct cgatggatta taaaaaacgt caagtgaacc tgtatttctc cgaactgtcg   540
gctcagacgc tggaggctga atcagtactt gctttagtgc gtgaactggg tcttcatgtc   600
ccaaacgagc tgggtctgaa attttgcaaa cgctccttct cagtataccc aacattaaac   660
tgggacacct cgaagattga ccgcctttgc ttctctgtaa tcagtacaga tccgacactt   720
gtacctagct cagacgaggg agacattgaa aaatttcaca attacgctac aaaggccccc   780
tatgcatatg ttgagaaaaa gcgtacactt gtttacggct tgactttatc tcccaaagag   840
gagtattata aattgggtgc cgtttaccac attactgacg tacaacgcaa acttttgaag   900
gcgttcgaca gccttgagga ttaa                                          924

SEQ ID NO: 36           moltype = AA  length = 307
FEATURE                 Location/Qualifiers
REGION                  1..307
                        note = Synthetic polypeptide
source                  1..307
                        mol_type = protein
                        organism = synthetic construct
SEQUENCE: 36
MSEAADVERV YAAIEEAAGL LGVACARDKI WPLLSTFQDT LVEGGSVVVF SMASGRHSTE    60
LDFSISVPPS HGDPYAIVVE KGLFPATGHP VDDLLADIQK HLPVSMFAID GEVTGGFKKI   120
YAFFPTDNMP GVAELAAIPS MPPAVAENAE LFARYGLDKV QMTSMDYKKR QVNLYFSELS   180
AQTLEAESVL ALVRELGLHV PNELGLKFCK RSFSVYPTLN WDTSKIDRLC FSVISTDPTL   240
VPSSDEGDIE KFHNYATKAP YAYVGEKRTL VYGLTLSPKE EYYKLGAVYH ITDVQRKLLK   300
AFDSLED                                                             307

SEQ ID NO: 37           moltype = DNA  length = 924
FEATURE                 Location/Qualifiers
misc_feature            1..924
                        note = Synthetic polynucleotide
source                  1..924
                        mol_type = other DNA
                        organism = synthetic construct
SEQUENCE: 37
atgtcggaag ctgccgatgt agaacgtgtc tacgccgcca tcgaagaagc cgcaggtttg    60
ttgggggtcg catgcgcacg cgataagatt tggcccttgc tgtcaacatt ccaggatacc   120
ttggttgagg gtggaagcgt agttgttttt agcatggcct cggggcgtca ctcaacggag   180
ctggacttct caatttccgt cccgcctagt catggcgatc cgtacgcgat tgtggtggaa   240
aagggcttgt tcccggcaac tggacatcca gttgatgacc ttctggcgga cattcagaag   300
catcttcccg tatctatgtt tgcgattgac ggggaagtta ccgggggggtt caaaaaaact   360
tatgcgttct cccgccgga taacatgccc ggtgtcgcgg aactggcggc catcccatcg   420
atgcctcctg cagtcgctga aaatgctgaa ctgttcgcgc gttatggcct ggacaaggta   480
caaatgacct cgatggatta taaaaaacgt caagtgaacc tgtatttctc cgaactgtcg   540
gctcagacgc tggaggctga atcagtactt gctttagtgc gtgaactggg tcttcatgtc   600
ccaaacgagc tgggtctgaa attttgcaaa cgctccttct cagtataccc aacattaaac   660
tgggacacct cgaagattga ccgcctttgc ttctctgtaa tcagtacaga tccgacactt   720
gtacctagct cagacgaggg agacattgaa aaatttcaca attacgctac aaaggccccc   780
tatgcatatg ttgagaaaaa gcgtacactt gtttacggct tgactttatc tcccaaagag   840
gagtattata aattgggtgc cgtttaccac attactgacg tacaacgcaa acttttgaag   900
gcgttcgaca gccttgagga ttaa                                          924

SEQ ID NO: 38           moltype = AA  length = 307
FEATURE                 Location/Qualifiers
REGION                  1..307
                        note = Synthetic polypeptide
source                  1..307
                        mol_type = protein
                        organism = synthetic construct
SEQUENCE: 38
MSEAADVERV YAAIEEAAGL LGVACARDKI WPLLSTFQDT LVEGGSVVVF SMASGRHSTE    60
LDFSISVPPS HGDPYAIVVE KGLFPATGHP VDDLLADIQK HLPVSMFAID GEVTGGFKKI   120
YAFFPPDNMP GVAELAAIPS MPPAVAENAE LFARYGLDKV QMTSMDYKKR QVNLYFSELS   180
AQTLEAESVL ALVRELGLHV PNELGLKFCK RSFSVYPTLN WDTSKIDRLC FSVISTDPTL   240
VPSSDEGDIE KFHNYATKAP YAYVGEKRTL VYGLTLSPKE EYYKLGAVYH ITDVQRKLLK   300
AFDSLED                                                             307

SEQ ID NO: 39           moltype = DNA  length = 924
```

| FEATURE | Location/Qualifiers |
|---|---|
| misc_feature | 1..924 |
| | note = Synthetic polynucleotide |
| source | 1..924 |
| | mol_type = other DNA |
| | organism = synthetic construct |

SEQUENCE: 39

```
atgtcggaag ctgccgatgt agaacgtgtc tacgccgcca tcgaagaagc cgcaggtttg    60
ttgggggtcg catgcgcacg cgataagatt tggcccttgc tgtcaacatt ccaggatacc   120
ttggttgagg gtgaagcgt  agttgttttt agcatggcgc cggggcgtca ctcaacggag   180
ctggacttct caatttccgt cccgcctagt catggcgatc cgtacgcgat tgtggtggaa   240
aagggcttgt cccggcaac  tggacatcca gttgatgacc ttctggcgga cattcagaag   300
catcttcccg tatctatgtt tgcgattgac ggggaagtta ccgggggggtt caaaaaaact   360
tatgcgttct tcccgaccga taacatgccc ggtgtcgcgg aactggcggc catcccatcg   420
atgcctcctg cagtcgctga aaatgctgaa ctgttcgcgc gttatggcct ggacaaggta   480
caaatgattt cgatggatta taaaaaacgt caagtgaacc tgtatttctc cgaactgtcg   540
gctcagacgc tggaggctga atcagtactt gctttagtgc gtgaactggg tcttcatgtc   600
ccaaacgagc tgggtctgaa attttgcaaa cgctccttct cagtataccc aacattaaac   660
tgggacacct cgaagattga ccgcctttgc ttctctgtaa tcagtacaga tccgacactt   720
gtacctagct cagacgaggg agacattgaa aaatttcaca attacgctac aaaggccccc   780
tatgcatatg ttggagaaaa gcgtacactt gtttacgggct tgactttatc tcccaaagag   840
gagtattata aattgggtgc cgtttaccac attactgacg tacaacgcaa acttttgaag   900
gcgttcgaca gccttgagga ttaa                                           924
```

| SEQ ID NO: 40 | moltype = AA length = 307 |
|---|---|
| FEATURE | Location/Qualifiers |
| REGION | 1..307 |
| | note = Synthetic polypeptide |
| source | 1..307 |
| | mol_type = protein |
| | organism = synthetic construct |

SEQUENCE: 40

```
MSEAADVERV YAAIEEAAGL LGVACARDKI WPLLSTFQDT LVEGGSVVVF SMASGRHSTE    60
LDFSISVPPS HGDPYAIVVE KGLFPATGHP VDDLLADIQK HLPVSMFAID GEVTGGFKKT   120
YAFFPTDNMP GVAELAAIPS MPPAVAENAE LFARYGLDKV QMISMDYKKR QVNLYFSELS   180
AQTLEAESVL ALVRELGLHV PNELGLKFCK RSFSVYPTLN WDTSKIDRLC FSVISTDPTL   240
VPSSDEGDIE KFHNYATKAP YAYVGEKRTL VYGLTLSPKE EYYKLGAVYH ITDVQRKLLK   300
AFDSLED                                                             307
```

| SEQ ID NO: 41 | moltype = DNA length = 924 |
|---|---|
| FEATURE | Location/Qualifiers |
| misc_feature | 1..924 |
| | note = Synthetic polynucleotide |
| source | 1..924 |
| | mol_type = other DNA |
| | organism = synthetic construct |

SEQUENCE: 41

```
atgtcggaag ctgccgatgt agaacgtgtc tacgccgcca tcgaagaagc cgcaggtttg    60
ttgggggtcg catgcgcacg cgataagatt tggcccttgc tgtcaacatt ccaggatacc   120
ttggttgagg gtgaagcgt  agttgttttt agcatggcct cggggcgtca ctcaacggag   180
ctggacttct caatttccgt cccgcctagt catggcgatc cgtacgcgat tgtggtggaa   240
aagggcttgt cccggcaac  tggacatcca gttgatgacc ttctggcgga cattcagaag   300
catcttcccg tatctatgtt tgcgattgac ggggaagtta ccgggggggtt caaaaaaact   360
tatgcgttct tcccgaccga taacatgccc ggtgtcgcgg aactggcggc catcccatcg   420
atgcctcctg cagtcgctga aaatgctgaa ctgttcgcgc gttatggcct ggacaaggta   480
caaatgacct cgatggatta taaaaaacgt caagtgaacc tgtatttctc cgaactgtcg   540
ccgcagacgc tggaggctga atcagtactt gctttagtgc gtgaactggg tcttcatgtc   600
ccaaacgagc tgggtctgaa attttgcaaa cgctccttct cagtataccc aacattaaac   660
tgggacacct cgaagattga ccgcctttgc ttctctgtaa tcagtacaga tccgacactt   720
gtacctagct cagacgaggg agacattgaa aaatttcaca attacgctac aaaggccccc   780
tatgcatatg ttggagaaaa gcgtacactt gtttacgggct tgactttatc tcccaaagag   840
gagtattata aattgggtgc cgtttaccac attactgacg tacaacgcaa acttttgaag   900
gcgttcgaca gccttgagga ttaa                                           924
```

| SEQ ID NO: 42 | moltype = AA length = 307 |
|---|---|
| FEATURE | Location/Qualifiers |
| REGION | 1..307 |
| | note = Synthetic polypeptide |
| source | 1..307 |
| | mol_type = protein |
| | organism = synthetic construct |

SEQUENCE: 42

```
MSEAADVERV YAAIEEAAGL LGVACARDKI WPLLSTFQDT LVEGGSVVVF SMASGRHSTE    60
LDFSISVPPS HGDPYAIVVE KGLFPATGHP VDDLLADIQK HLPVSMFAID GEVTGGFKKT   120
YAFFPTDNMP GVAELAAIPS MPPAVAENAE LFARYGLDKV QMTSMDYKKR QVNLYFSELS   180
PQTLEAESVL ALVRELGLHV PNELGLKFCK RSFSVYPTLN WDTSKIDRLC FSVISTDPTL   240
VPSSDEGDIE KFHNYATKAP YAYVGEKRTL VYGLTLSPKE EYYKLGAVYH ITDVQRKLLK   300
AFDSLED                                                             307
```

```
SEQ ID NO: 43              moltype = DNA   length = 924
FEATURE                    Location/Qualifiers
misc_feature               1..924
                           note = Synthetic polynucleotide
source                     1..924
                           mol_type = other DNA
                           organism = synthetic construct
SEQUENCE: 43
atgtcggaag ctgccgatgt agaacgtgtc tacgccgcca tcgaagaagc cgcaggtttg   60
ttgggggtcg catgcgcacg cgataagatt tggcccttgc tgtcaacatt ccaggatacc  120
ttggttgagg gtgaaagcgt agttgttttt agcatggcct cggggcgtca ctcaacggag  180
ctggacttct caatttccgt cccgcctagt catggcgatc cgtacgcgat gtggtggaa   240
aagggcttgt tcccggcaac tggacatcca gttgatgacc ttctggcgga cattcagaag  300
catcttcccg tatctatgtt tgcgattgac ggggaagtta ccgggggggtt caaaaaaact  360
tatgcgttct ccccgaccga taacatgccc ggtgtcgcgg aactggcggc catcccatcg  420
atgcctcctg cagtcgctga aaatgctgaa ctgttcgcgc gttatggcct ggacaaggta  480
caaatgacct cgatggatta taaaaaacgt caagtgaacc tgtatttctc cgaactgtcg  540
gctcagacgc tggaggctga atcagtactt gctttagtgc gtgaactggg tcttcatgtc  600
ccaaacgagc tgggtctgaa attttgcaaa cgctccttct cagtataccc aacattaaac  660
tgggacacct cgaagattga ccgcctttgc ttctctgtaa tcagtacaga tccgacactt  720
gtacctagct cagacgaggg agacattgaa aaatttcaca attcgctac aaaggccccc   780
tatgcatatg ttggagaaaa gcgtgtgctt gtttacggct tgactttatc tcccaaagag  840
gagtattata aattgggtgc cgtttaccac attactgacg tacaacgcaa acttttgaag  900
gcgttcgaca gccttgagga ttaa                                         924

SEQ ID NO: 44              moltype = AA   length = 307
FEATURE                    Location/Qualifiers
REGION                     1..307
                           note = Synthetic polypeptide
source                     1..307
                           mol_type = protein
                           organism = synthetic construct
SEQUENCE: 44
MSEAADVERV YAAIEEAAGL LGVACARDKI WPLLSTFQDT LVEGGSVVVF SMASGRHSTE   60
LDFSISVPPS HGDPYAIVVE KGLFPATGHP VDDLLADIQK HLPVSMFAID GEVTGGFKKT  120
YAFFPTDNMP GVAELAAIPS MPPAVAENAE LFARYGLDKV QMTSMDYKKR QVNLYFSELS  180
AQTLEAESVL ALVRELGLHV PNELGLKFCK RSFSVYPTLN WDTSKIDRLC FSVISTDPTL  240
VPSSDEGDIE KFHNYATKAP YAYVGEKRVL VYGLTLSPKE EYYKLGAVYH ITDVQRKLLK  300
AFDSLED                                                            307

SEQ ID NO: 45              moltype = DNA   length = 924
FEATURE                    Location/Qualifiers
misc_feature               1..924
                           note = Synthetic polynucleotide
source                     1..924
                           mol_type = other DNA
                           organism = synthetic construct
SEQUENCE: 45
atgtcggaag ctgccgatgt agaacgtgtc tacgccgcca tcgaagaagc cgcaggtttg   60
ttgggggtcg catgcgcacg cgataagatt tggcccttgc tgtcaacatt ccaggatacc  120
ttggttgagg gtgaaagcgt agttgttttt agcatggcct cggggcgtca ctcaacggag  180
ctggacttct caatttccgt cccgcctagt catggcgatc cgtacgcgat gtggtggaa   240
aagggcttgt tcccggcaac tggacatcca attgatgacc ttctggcgga cattcagaag  300
catcttcccg tatctatgtt tgcgattgac ggggaagtta ccgggggggtt caaaaaaact  360
tatgcgttct ccccgaccga taacatgccc ggtgtcgcgg aactggcggc catcccatcg  420
atgcctcctg cagtcgctga aaatgctgaa ctgttcgcgc gttatggcct ggacaaggta  480
caaatgattt cgatggatta taaaaaacgt caagtgaacc tgtatttctc cgaactgtcg  540
gctcagacgc tggaggctga atcagtactt gctttagtgc gtgaactggg tcttcatgtc  600
ccaaacgagc tgggtctgaa attttgcaaa cgctccttct cagtataccc aacattaaac  660
tgggacacct cgaagattga ccgcctttgc ttctctgtaa tcagtacaga tccgacactt  720
gtacctagct cagacgaggg agacattgaa aaatttcaca attcgctac aaaggccccc   780
tatgcatatg ttggagaaaa gcgtacactt gtttacggct tgactttatc tcccaaagag  840
gagtattata aattgggtgc cgtttaccac attactgacg tacaacgcaa acttttgaag  900
gcgttcgaca gccttgagga ttaa                                         924

SEQ ID NO: 46              moltype = AA   length = 307
FEATURE                    Location/Qualifiers
REGION                     1..307
                           note = Synthetic polypeptide
source                     1..307
                           mol_type = protein
                           organism = synthetic construct
SEQUENCE: 46
MSEAADVERV YAAIEEAAGL LGVACARDKI WPLLSTFQDT LVEGGSVVVF SMASGRHSTE   60
LDFSISVPPS HGDPYAIVVE KGLFPATGHP IDDLLADIQK HLPVSMFAID GEVTGGFKKT  120
YAFFPTDNMP GVAELAAIPS MPPAVAENAE LFARYGLDKV QMISMDYKKR QVNLYFSELS  180
AQTLEAESVL ALVRELGLHV PNELGLKFCK RSFSVYPTLN WDTSKIDRLC FSVISTDPTL  240
VPSSDEGDIE KFHNYATKAP YAYVGEKRTL VYGLTLSPKE EYYKLGAVYH ITDVQRKLLK  300
AFDSLED                                                            307
```

```
SEQ ID NO: 47            moltype = DNA   length = 924
FEATURE                  Location/Qualifiers
misc_feature             1..924
                         note = Synthetic polynucleotide
source                   1..924
                         mol_type = other DNA
                         organism = synthetic construct
SEQUENCE: 47
atgtcggaag ctgccgatgt agaacgtgtc tacgccgcca tcgaagaagc cgcaggtttg    60
ttgggggtcc cgtgcgcacg cgataagatt tggcccttgc tgtcaacatt ccaggatacc   120
ttggttgagg gtggaagcgt agttgttttt agcatggcct cggggcgtca ctcaacggag   180
ctggacttct caatttccgt cccgcctagt catggcgatc cgtacgcgat tgtggtggaa   240
aagggcttgt tcccggcaac tggacatcca attgatgacc ttctggcgga cattcagaag   300
catcttcccg tatctatgtt tgcgattgac ggggaagtta ccgggggggtt caaaaaaact   360
tatgcgttct cccgccggga taacatgccc ggtgtcgcgg aactggcggc catcccatcg   420
atgcctcctg cagtcgctga aaatgctgaa ctgttcgcgc gttatggcct ggacaaggta   480
caaatgattt cgatggatta taaaaaacgt caagtaacct gtatttctc cgaactgtcg   540
gctcagacgc tggaggctga atcagtactt gctttagtgc gtgaactggg tcttcatgtc   600
ccaaacgagc tgggtctgaa attttgcaaa cgctccttct cagtataccc aacattaaac   660
tgggacacct cgaagattga ccgcctttgc ttctctgtaa tcagtacaga tccgacactt   720
gtacctagct cagacgaggg agacattgaa aaatttcaca attcgctac aaaggccccc   780
tatgcatatg ttggagaaaa gcgtacactt gtttacggct tgactttatc tcccaaagag   840
gagtattata aattgggtgc cgtttaccac attactgacg tacaacgcaa acttttgaag   900
gcgttcgaca gccttgagga ttaa                                         924

SEQ ID NO: 48            moltype = AA   length = 307
FEATURE                  Location/Qualifiers
REGION                   1..307
                         note = Synthetic polypeptide
source                   1..307
                         mol_type = protein
                         organism = synthetic construct
SEQUENCE: 48
MSEAADVERV YAAIEEAAGL LGVPCARDKI WPLLSTFQDT LVEGGSVVVF SMASGRHSTE    60
LDFSISVPPS HGDPYAIVVE KGLFPATGHP IDDLLADIQK HLPVSMFAID GEVTGGFKKT   120
YAFFPPDNMP GVAELAAIPS MPPAVAENAE LFARYGLDKV QMISMDYKKR QVNLYFSELS   180
AQTLEAESVL ALVRELGLHV PNELGLKFCK RSFSVYPTLN WDTSKIDRLC FSVISTDPTL   240
VPSSDEGDIE KFHNYATKAP YAYVGEKRTL VYGLTLSPKE EYYKLGAVYH ITDVQRKLLK   300
AFDSLED                                                            307

SEQ ID NO: 49            moltype = DNA   length = 924
FEATURE                  Location/Qualifiers
misc_feature             1..924
                         note = Synthetic polynucleotide
source                   1..924
                         mol_type = other DNA
                         organism = synthetic construct
SEQUENCE: 49
atgtcggaag ctgccgatgt agaacgtgtc tacgccgcca tcgaagaagc cgcaggtttg    60
ttgggggtcc cgtgcgcacg cgataagatt tggcccttgc tgtcaacatt ccaggatacc   120
ttggttgagg gtggaagcgt agttgttttt agcatggcct cggggcgtca ctcaacggag   180
ctggacttct caatttccgt cccgcctagt catggcgatc cgtacgcgat tgtggtggaa   240
aagggcttgt tcccggcaac tggacatcca attgatgacc ttctggcgga cattcagaag   300
catcttcccg tatctatgtt tgcgattgac ggggaagtta ccgggggggtt caaaaaaact   360
tatgcgttct cccgccggga taacatgccc ggtgtcgcgg aactggcggc catcccatcg   420
atgcctcctg cagtcgctga aaatgctgaa ctgttcgcgc gttatggcct ggacaaggta   480
caaatgattt cgatggatta taaaaaacgt caagtgaacc tgtatttctc cgaactgtcg   540
gctcagacgc tggaggctga atcagtactt gctttagtgc gtgaactggg tcttcatgtc   600
ccaaacgagc tgggtctgaa attttgcaaa cgctccttct cagtataccc aacattaaac   660
tgggacacct cgaagattga ccgcctttgc ttctctgtaa tcagtacaga tccgacactt   720
gtacctagct cagacgaggg agacattgaa aaatttcaca attcgctac aaaggccccc   780
tatgcatatg ttggagaaaa gcgtgtgctt gtttacggct tgactttatc tcccaaagag   840
gagtattata aattgggtgc cgtttaccac attactgacg tacaacgcaa acttttgaag   900
gcgttcgaca gccttgagga ttaa                                         924

SEQ ID NO: 50            moltype = AA   length = 307
FEATURE                  Location/Qualifiers
REGION                   1..307
                         note = Synthetic polypeptide
source                   1..307
                         mol_type = protein
                         organism = synthetic construct
SEQUENCE: 50
MSEAADVERV YAAIEEAAGL LGVPCARDKI WPLLSTFQDT LVEGGSVVVF SMASGRHSTE    60
LDFSISVPPS HGDPYAIVVE KGLFPATGHP IDDLLADIQK HLPVSMFAID GEVTGGFKKT   120
YAFFPPDNMP GVAELAAIPS MPPAVAENAE LFARYGLDKV QMISMDYKKR QVNLYFSELS   180
AQTLEAESVL ALVRELGLHV PNELGLKFCK RSFSVYPTLN WDTSKIDRLC FSVISTDPTL   240
VPSSDEGDIE KFHNYATKAP YAYVGEKRVL VYGLTLSPKE EYYKLGAVYH ITDVQRKLLK   300
```

```
AFDSLED                                                                         307

SEQ ID NO: 51           moltype = DNA   length = 924
FEATURE                 Location/Qualifiers
misc_feature            1..924
                        note = Synthetic polynucleotide
source                  1..924
                        mol_type = other DNA
                        organism = synthetic construct
SEQUENCE: 51
atgtccgagg ccgcagatgt agaacgcgtt tacgcagcta tggaggaagc cgcagggctg   60
ctgggggtgg cgtgtgctcg cgacaaaatc tatcccttc tttcgacgtt tcaggacaca  120
ctggtagaag gaggctccgt tattgtgttt agcatggctt ccggtcgtca cagtacagag  180
cttgatttct caatttccgt acccacgtcg catgggacc cctatgccac tgttgtggaa  240
aaggggttgt ttccagcgac agggcaccct gtcgatgacc tgcttgctga tactcaaaaa  300
catttacccg tcagcatgtt tgctatcgat ggcgaagtca ccggcggctt caagaagaca  360
tatgcttttt tcccaacaga taatatgcct ggcgtagcag agttgtcggc tatcccgagt  420
atgccgcccg cagtggccga aacgctgag ctgttcgctc gttatggcct tgataaggtt  480
caaatgacaa gtatggatta caagaagcgt caggtaaacc tgtacttcag cgagctttca  540
gctcaaaccc tggaagccga gtccgtatta gcccttgtac gtgagttggg cttacacgta  600
ccaaacgagc ttggactgaa attctgtaaa cgctcgtta gtgtttaccc tacattaaat  660
tgggagactg gcaagattga tcgttatgc ttcagcgtga tctccaacga tccgactctg  720
gtgccgagct ctgatgaagg agatattgaa aaatttcata attatgctac aaaggccccg  780
tatgcatatg ttggcgaaaa gcgcactctt gtctatggcc tgactttaag tcccaaggag  840
gagtactata aactgggagc agtgtaccat atcaccgacg ttcaacgcgg acttttgaaa  900
gcgtttgact cattggagga ttaa                                         924

SEQ ID NO: 52           moltype = AA    length = 307
FEATURE                 Location/Qualifiers
REGION                  1..307
                        note = Synthetic polypeptide
source                  1..307
                        mol_type = protein
                        organism = synthetic construct
SEQUENCE: 52
MSEAADVERV YAAMEEAAGL LGVACARDKI YPLLSTFQDT LVEGGSVIVF SMASGRHSTE   60
LDFSISVPTS HGDPYATVVE KGLFPATGHP VDDLLADTQK HLPVSMFAID GEVTGGFKKT  120
YAFFPTDNMP GVAELSAIPS MPPAVAENAE LFARYGLDKV QMTSMDYKKR QVNLYFSELS  180
AQTLEAESVL ALVRELGLHV PNELGLKFCK RSFSVYPTLN WETGKIDRLC FSVISNDPTL  240
VPSSDEGDIE KFHNYATKAP YAYVGEKRTL VYGLTLSPKE EYYKLGAVYH ITDVQRGLLK  300
AFDSLED                                                            307

SEQ ID NO: 53           moltype = DNA   length = 924
FEATURE                 Location/Qualifiers
misc_feature            1..924
                        note = Synthetic polynucleotide
source                  1..924
                        mol_type = other DNA
                        organism = synthetic construct
SEQUENCE: 53
atgtccgagg ccgcagatgt agaacgcgtt tacgcagcta tggaggaagc cgcagggctg   60
ctgggggtgg cgtgtgctcg cgacaaaatc tatcccttc tttcgacgtt tcaggacaca  120
ctggtagaag gaggctccgt tgttgtgttt agcatggctt ccggtcgtca cagtacagag  180
cttgatttct caatttccgt acccacgtcg catgggacc cctatgccac tgttgtggaa  240
aaggggttgt ttccagcgac agggcaccct gtcgatgacc tgcttgctga tactcaaaaa  300
catttacccg tcagcatgtt tgctatcgat ggcgaagtca ccggcggctt caagaagaca  360
tatgcttttt tcccaacaga taatatgcct ggcgtagcag agttgtcggc tatcccgagt  420
atgccgccca gcgtggccga aacgctgag ctgttcgctc gttatggcct tgataaggtt  480
caaatgacaa gtatggatta caagaagcgt caggtaaacc tgtacttcag cgagctttca  540
gctcaaaccc tggaagccga gtccgtatta gcccttgtac gtgagttggg cttacacgta  600
ccaaacgagc ttggactgaa attctgtaaa cgctcgtta gtgtttaccc tacattaaat  660
tgggagactg gcaagattga tcgttatgc ttcagcgtga tctccaacga tccgactctg  720
gtgccgagct ctgatgaagg agatattgaa aaatttcata attatgctac aaaggccccg  780
tatgcatatg ttggcgaaaa gcgcactctt gtctatggcc tgactttaag tcccaaggag  840
gagtactata aactgggagc agtgtaccat atcaccgacg ttcaacgcgg acttttgaaa  900
gcgtttgact cattggagga ttaa                                         924

SEQ ID NO: 54           moltype = AA    length = 307
FEATURE                 Location/Qualifiers
REGION                  1..307
                        note = Synthetic polypeptide
source                  1..307
                        mol_type = protein
                        organism = synthetic construct
SEQUENCE: 54
MSEAADVERV YAAMEEAAGL LGVACARDKI YPLLSTFQDT LVEGGSVVVF SMASGRHSTE   60
LDFSISVPTS HGDPYATVVE KGLFPATGHP VDDLLADTQK HLPVSMFAID GEVTGGFKKT  120
YAFFPTDNMP GVAELSAIPS MPPSVAENAE LFARYGLDKV QMTSMDYKKR QVNLYFSELS  180
AQTLEAESVL ALVRELGLHV PNELGLKFCK RSFSVYPTLN WETGKIDRLC FSVISNDPTL  240
```

```
VPSSDEGDIE KFHNYATKAP YAYVGEKRTL VYGLTLSPKE EYYKLGAVYH ITDVQRGLLK    300
AFDSLED                                                              307

SEQ ID NO: 55           moltype = DNA  length = 924
FEATURE                 Location/Qualifiers
misc_feature            1..924
                        note = Synthetic polynucleotide
source                  1..924
                        mol_type = other DNA
                        organism = synthetic construct
SEQUENCE: 55
atgtccgagg ccgcagatgt agaacgcgtt tacgcagcta tggaggaagc cgcagggctg    60
ctgggggtgg cgtgtgctcg cgacaaaatc tatccccttc tttcgacgtt tcaggacaca    120
ctggtagaag gaggctccgt tgttgtgttt agcatggctt ccggtcgtca cagtacagag    180
cttgatttct caatttccgt acccacgtcg catggggacc cctatgccac tgttgtggag    240
aagggggttgt ttccagcgac agggcaccct gtcgatgacc tgcttgctga tactcaaaaa    300
catttacccg tcagcatgtt tgctatcgat ggcgaagtca ccggcggctt caagaagaca    360
tatgcttttt tcccaacaga taatatgcct ggcgtagcag agttgtcggc tatcccgagt    420
atgccgcccg cagtggccga gaacgctgag ctgttcgctc gttatggcct tgataaggtt    480
caaatgacaa gtatggatta caagaagcgt caggtaaacc tgtacttcag cgagctttca    540
gctcaaaccc tggaagccga gtccgtatta gcccttgtac gtgagttggg cttacacgaa    600
ccaaacgagc ttggactgaa attctgtaaa cgctcgtttα gtgtttaccc tacattaaat    660
tgggagactg gcaagattga tcgtttatgc ttcagcgtga tctccaacga tccgactctg    720
gtgccgagct ctgatgaagg agatattgaa aaatttcata atattgctac aaaggccccg    780
tatgcatatg ttggcgaaaa gcgcactctt gtctatggcc tgactttaag tcccaaggag    840
gagtactata aactgggagc agtgtaccat atcaccgacg tcaacgcgg acttttgaaa    900
gcgtttgact cattggagga ttaa                                           924

SEQ ID NO: 56           moltype = AA  length = 307
FEATURE                 Location/Qualifiers
REGION                  1..307
                        note = Synthetic polypeptide
source                  1..307
                        mol_type = protein
                        organism = synthetic construct
SEQUENCE: 56
MSEAADVERV YAAMEEAAGL LGVACARDKI YPLLSTFQDT LVEGGSVVVF SMASGRHSTE    60
LDFSISVPTS HGDPYATVVE KGLFPATGHP VDDLLADTQK HLPVSMFAID GEVTGGFKKT    120
YAFFPTDNMP GVAELSAIPS MPPAVAENAE LFARYGLDKV QMTSMDYKKR QVNLYFSELS    180
AQTLEAESVL ALVRELGLHE PNELGLKFCK RSFSVYPTLN WETGKIDRLC FSVISNDPTL    240
VPSSDEGDIE KFHNYATKAP YAYVGEKRTL VYGLTLSPKE EYYKLGAVYH ITDVQRGLLK    300
AFDSLED                                                              307

SEQ ID NO: 57           moltype = DNA  length = 924
FEATURE                 Location/Qualifiers
misc_feature            1..924
                        note = Synthetic polynucleotide
source                  1..924
                        mol_type = other DNA
                        organism = synthetic construct
SEQUENCE: 57
atgtccgagg ccgcagatgt agaacgcgtt tacgcagcta tggaggaagc cgcagggctg    60
ctgggggtgg cgtgtgctcg cgacaaaatc tatccccttc tttcgacgtt tcaggacaca    120
ctggtagaag gaggctccgt tgttgtgttt agcatggctt ccggtcgtca cagtacagag    180
cttgatttct caatttccgt acccacgtcg catggggacc cctatgccac tgttgtggag    240
aagggggttgt ttccagcgac agggcaccct gtcgatgacc tgcttgctga tactcaaaaa    300
catttacccg tcagcatgtt tgctatcgat ggcgaagtca ccggcggctt caagaagaca    360
tatgcttttt tcccaacaga taatatgcct ggcgtagcag agttgtcggc tatcccgagt    420
atgccgcccg cagtggccga gaacgctgag ctgttcgctc gttatggcct tgataaggtt    480
caaatgacaa gtatggatta caagaagcgt caggtaaacc tgtacttcag cgagctttca    540
gctcaaaccc tggaagccga gtccgtatta gcccttgtac gtgagttggg cttacacgta    600
ccaaacgagc ttggactgaa attctgtaaa cgctcgttta gtgtttaccc tacattaaat    660
tgggagactg gcaagattga tcgtttatgc ttcagcgtga tctccaacga tccgactctg    720
gtgccgagct ctgatgaagg agatattgaa aaatttcata atattgctac aaaggccccg    780
tatgcatatg ttggcgaaaa gcgcactctt gtctatggcc tggtgttaag tcccaaggag    840
gagtactata aactgggagc agtgtaccat atcaccgacg tcaacgcgg acttttgaaa    900
gcgtttgact cattggagga ttaa                                           924

SEQ ID NO: 58           moltype = AA  length = 307
FEATURE                 Location/Qualifiers
REGION                  1..307
                        note = Synthetic polypeptide
source                  1..307
                        mol_type = protein
                        organism = synthetic construct
SEQUENCE: 58
MSEAADVERV YAAMEEAAGL LGVACARDKI YPLLSTFQDT LVEGGSVVVF SMASGRHSTE    60
LDFSISVPTS HGDPYATVVE KGLFPATGHP VDDLLADTQK HLPVSMFAID GEVTGGFKKT    120
YAFFPTDNMP GVAELSAIPS MPPAVAENAE LFARYGLDKV QMTSMDYKKR QVNLYFSELS    180
```

```
AQTLEAESVL ALVRELGLHV PNELGLKFCK RSFSVYPTLN WETGKIDRLC FSVISNDPTL    240
VPSSDEGDIE KFHNYATKAP YAYVGEKRTL VYGLVLSPKE EYYKLGAVYH ITDVQRGLLK    300
AFDSLED                                                              307
```

What is claimed is:

1. A recombinant polypeptide having prenyltransferase activity and comprising an amino acid sequence of at least 85% identity to SEQ ID NO: 4, and at least one amino acid residue difference as compared to SEQ ID NO: 4 at one or more positions selected from 163, 91, 48, 120, 200, and 275 and/or at least one amino acid difference selected from A24P, A144S, and A181P.

2. The recombinant polypeptide of claim 1, wherein the at least one amino acid residue difference is selected from T163I, V91I, V48I, T120I, V200E, T269V, or T275V.

3. The recombinant polypeptide of claim 1, wherein the at least one amino acid residue difference includes T163I and V91I.

4. The recombinant polypeptide of claim 1, wherein the at least one amino acid residue difference includes T163I, V91I, A24P, and T126P.

5. The recombinant polypeptide of claim 1, wherein the recombinant polypeptide comprises:
   (i) a S amino acid residue at position 232, and a V amino acid residue at position 288;
   (ii) an amino acid residue difference as compared to SEQ ID NO: 4 at position 161;
   (iii) an amino acid residue difference as compared to SEQ ID NO: 4 at one or more positions selected from 14, 31, 33, 69, 77, 78, 80, 93, 98, 112, 114, 126, 129, 131, 136, 222, 224, 225, 230, 236, 277, and 297;
   (iv) at least one amino acid residue difference as compared to SEQ ID NO: 4 selected from M14I, Y31W, L33I, T69P, T77I, V78A, E80A, D93S, T98I, E112G, T114V, T126P, M129L, G131Q, S136A, E222D, G224S, K225Q, C230T, N236T, S277T, and G297K; or
   (v) a set of additional amino residue differences selected from:
      (a) M14I, Y31W, T69P, T77I, T98I, S136A, E222D, G224S, N236T, and G297K;
      (b) M14I, Y31W, T69P, T77I, E80A, D93S, T98I, T126P, M129L, G131Q, S136A, E222D, G224S, N236T, S277T, and G297K; or
      (c) M14I, Y31W, L33I, T69P, T77I, V78A, E80A, D93S, T98I, E112G, T114V, T126P, M129L, G131Q, S136A, E222D, G224S, K225Q, N236T, S277T, and G297K.

6. The recombinant polypeptide of claim 1, wherein the recombinant polypeptide comprises an amino acid residue difference Q161H.

7. The recombinant polypeptide of claim 1 in which the thermostability of the recombinant polypeptide as compared to a polypeptide consisting of SEQ ID NO: 4 is increased at least 1.2-fold.

8. The recombinant polypeptide of claim 1 in which the prenyltransferase activity of the recombinant polypeptide as compared to a polypeptide consisting of SEQ ID NO: 2 or 4 is increased at least 1.2-fold.

9. A polynucleotide encoding the recombinant polypeptide of claim 1.

10. The polynucleotide of claim 9 in which the polynucleotide comprises a sequence of at least 80% identity to a sequence selected from the group consisting of SEQ ID NO: 15, 9, 5, 7, 11, 13, 17, 19, 21, 23, 25, 27, 29, 31, 33, 35, 37, 39, 41, 43, 45, 47, 49, 51, 53, 55, and 57.

11. An expression vector comprising the polynucleotide of claim 9.

12. A host cell comprising the polynucleotide of claim 9.

13. A method for preparing a recombinant polypeptide having prenyltransferase activity comprising:
   (a) transforming a host cell with an expression vector comprising a polynucleotide encoding a recombinant polypeptide of claim 1;
   (b) culturing said transformed host cell under conditions whereby the recombinant polypeptide is produced by the host cell; and
   (c) recovering the recombinant polypeptide from the host cell, wherein recovering comprises heating a solution comprising the recombinant polypeptide to a temperature of at least 55° C. for at least 30 minutes.

14. The method of claim 13, wherein the expression vector comprises a secretion signal.

15. A composition comprising a recombinant polypeptide having prenyltransferase activity of claim 1 and one or more enzymes that produce a substrate for the recombinant polypeptide.

16. The composition of claim 15, wherein:
   (i) the one or more enzymes produce a substrate selected from: geranyl pyrophosphate (GPP), olivetolic acid (OA), divarinic acid (DA), sphaerophorolic acid (PA), and a combination thereof; or
   (ii) the one or more enzymes comprises a plurality of enzymes that convert isoprenol or prenol to geranylpyrophosphate (GPP).

17. The composition of claim 15, wherein the one or more enzymes comprise:
   (i) enzymes that convert malonate and acetyl-coenzyme A (CoA) to malonyl-CoA; or
   (ii) enzymes that convert adenosine diphosphate (ADP) or adenosine monophosphate (AMP) to adenosine triphosphate (ATP).

18. The composition of claim 17, wherein the enzymes that convert ADP or AMP to ATP also convert acetyl-phosphate to acetic acid.

19. The composition of claim 15, wherein the one or more enzymes comprise:
   (i) Acyl activating enzyme 3 (AAE3);
   (ii) Olivetol synthase (OLS); or
   (iii) Olivetolic acid cyclase (OAC).

20. The composition of claim 15, wherein the one or more enzymes comprise:
   (i) Acetyl-phosphate transferase (PTA);
   (ii) Malonate decarboxylase alpha subunit (mdcA);
   (iii) Acyl activating enzyme 3 (AAE3);
   (iv) Olivetol synthase (OLS);
   (v) Olivetolic acid cyclase (OAC);
   (vi) Hydroxyethylthiazole kinase (ThiM);
   (vii) Isopentenyl kinase (IPK);
   (viii) Isopentyl diphosphate isomerase (IDI);

(ix) Diphosphomevalonate decarboxylase alpha subunit (MDCa); or
(x) Geranyl-PP synthase (GPPS) or Farnesyl-PP synthase mutant S82F (FPPS S82F).

* * * * *